US012582562B2

(12) United States Patent
Willhaus et al.

(10) Patent No.: US 12,582,562 B2
(45) Date of Patent: Mar. 24, 2026

(54) ABSORBENT ARTICLES WITH FRANGIBLE PATHWAYS ADAPTED FOR TEAR PROPAGATION BETWEEN REGIONS OF LAMINATES HAVING DIFFERENT NUMBERS OF LAYERS OF SUBSTRATES

(71) Applicant: The Procter & Gamble Company, Cincinnati, OH (US)

(72) Inventors: Keith Richard Willhaus, Cincinnati, OH (US); Jeromy Thomas Raycheck, South Lebanon, OH (US); Jeffry Rosiak, Loveland, OH (US); Jason Edward Naylor, Loveland, OH (US); Michael Devin Long, Harrison Township, OH (US); Nicholas Alexander Taylor, Woodlawn, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 385 days.

(21) Appl. No.: 18/214,626

(22) Filed: Jun. 27, 2023

(65) Prior Publication Data

US 2024/0000626 A1 Jan. 4, 2024

Related U.S. Application Data

(60) Provisional application No. 63/432,410, filed on Dec. 14, 2022, provisional application No. 63/357,043, (Continued)

(51) Int. Cl.
*A61F 13/49* (2006.01)
*A61F 13/15* (2006.01)
(Continued)

(52) U.S. Cl.
CPC .. *A61F 13/49011* (2013.01); *A61F 13/15585* (2013.01); *A61F 13/15699* (2013.01);
(Continued)

(58) Field of Classification Search
CPC .......... A61F 13/15585; A61F 13/15699; A61F 13/15723; A61F 13/49011; A61F 13/4902;
(Continued)

(56) References Cited

U.S. PATENT DOCUMENTS 4,610,680 A 9/1986 Lafleur
4,872,871 A 10/1989 Proxmire et al.
(Continued)

FOREIGN PATENT DOCUMENTS

DE 19813334 A1 9/1999
DE 20220237 U1 3/2003
(Continued)

OTHER PUBLICATIONS

All Office Actions; U.S. Appl. No. 18/214,548, filed on Jun. 27, 2023.
(Continued)

*Primary Examiner* — Michele Kidwell
(74) *Attorney, Agent, or Firm* — Charles R. Matson

(57) ABSTRACT

The present disclosure relates to absorbent articles including a first belt and a second belt. The first belt and/or the second belt may comprise a first region and a second region, wherein the first region comprises a first number of layers of substrates and the second region comprises a second number of layers of substrates, wherein the first number of layers substrates is greater than second number of layers of substrates. In addition, the first belt and/or the second belt may comprise one or more frangible pathways comprising first lines of weakness positioned in the first region, second lines
(Continued)

of weakness positioned in the second region, and at least one transition line of weakness extending partially through the first region and the second region.

26 Claims, 39 Drawing Sheets

Related U.S. Application Data filed on Jun. 30, 2022, provisional application No. 63/432,400, filed on Dec. 14, 2022, provisional application No. 63/432,401, filed on Dec. 14, 2022, provisional application No. 63/432,402, filed on Dec. 14, 2022, provisional application No. 63/432,403, filed on Dec. 14, 2022, provisional application No. 63/432,404, filed on Dec. 14, 2022, provisional application No. 63/432,406, filed on Dec. 14, 2022, provisional application No. 63/432,413, filed on Dec. 14, 2022.

(51) Int. Cl.

| | |
|---|---|
| *A61F 13/493* | (2006.01) |
| *A61F 13/496* | (2006.01) |
| *A61F 13/512* | (2006.01) |
| *A61F 13/514* | (2006.01) |
| *A61F 13/551* | (2006.01) |
| *A61F 13/56* | (2006.01) |
| *A61F 13/62* | (2006.01) |
| *A61F 13/64* | (2006.01) |
| *A61F 13/68* | (2006.01) |
| *A61F 13/84* | (2006.01) |

(52) U.S. Cl.
CPC .. *A61F 13/15723* (2013.01); *A61F 13/15739* (2013.01); *A61F 13/15747* (2013.01); *A61F 13/15756* (2013.01); *A61F 13/4902* (2013.01); *A61F 13/493* (2013.01); *A61F 13/496* (2013.01); *A61F 13/5126* (2013.01); *A61F 13/51478* (2013.01); *A61F 13/5622* (2013.01); *A61F 13/5644* (2013.01); *A61F 13/565* (2013.01); *A61F 13/5655* (2013.01); *A61F 13/62* (2013.01); *A61F 13/622* (2013.01); *A61F 13/625* (2013.01); *A61F 13/64* (2013.01); *A61F 13/68* (2013.01); *A61F 13/84* (2013.01); *A61F 2013/15292* (2013.01); *A61F 2013/15406* (2013.01); *A61F 2013/15934* (2013.01); *A61F 2013/49025* (2013.01); *A61F 2013/49087* (2013.01); *A61F 13/5512* (2013.01); *A61F 2013/8497* (2013.01)

(58) Field of Classification Search
CPC .............. A61F 13/49061; A61F 13/493; A61F 13/496; A61F 13/5126; A61F 13/51478; A61F 13/5512; A61F 13/5622; A61F 13/5644; A61F 13/565; A61F 13/5655; A61F 13/62; A61F 13/622; A61F 13/625; A61F 13/64; A61F 13/68; A61F 13/84; A61F 2013/15406; A61F 2013/15934; A61F 2013/49025; A61F 2013/49087; A61F 2013/8497; A61F 2013/55125; A61F 13/56; A61F 13/49007; A61F 2013/49063; A61F 2013/8402; A61F 13/49001
See application file for complete search history.

(56) References Cited

U.S. PATENT DOCUMENTS

| | | | |
|---|---|---|---|
| 5,074,854 | A | 12/1991 | Davis |
| H1420 | H | 2/1995 | Richardson |
| 5,575,784 | A | 11/1996 | Ames-ooten et al. |
| 5,624,420 | A | 4/1997 | Bridges et al. |
| 5,766,389 | A | 6/1998 | Brandon et al. |
| 5,897,546 | A | 4/1999 | Kido et al. |
| 6,027,484 | A | 2/2000 | Romare |
| 6,113,717 | A | 9/2000 | Vogt et al. |
| 6,287,287 | B1 | 9/2001 | Elsberg |
| 6,497,695 | B1 | 12/2002 | Bruemmer-prestley et al. |
| 6,508,797 | B1 | 1/2003 | Pozniak et al. |
| 6,508,799 | B1 | 1/2003 | Freiburger et al. |
| 6,524,294 | B1 | 2/2003 | Hilston et al. |
| 6,575,949 | B1 | 6/2003 | Waksmundzki et al. |
| 6,579,275 | B1 | 6/2003 | Pozniak et al. |
| 6,585,855 | B2 | 7/2003 | Drew et al. |
| 6,712,922 | B2 | 3/2004 | Sorenson et al. |
| 6,743,321 | B2 | 6/2004 | Guralski |
| 6,752,796 | B2 | 6/2004 | Karami |
| 6,783,487 | B2 | 8/2004 | Duhm et al. |
| 6,838,040 | B2 | 1/2005 | Mlinar et al. |
| 6,976,978 | B2 | 12/2005 | Ruman et al. |
| 6,991,696 | B2 | 1/2006 | Wagner et al. |
| 7,077,834 | B2 | 7/2006 | Bishop et al. |
| 7,150,730 | B2 | 12/2006 | Hasler et al. |
| 7,156,833 | B2 | 1/2007 | Couture-dorschner |
| 7,250,549 | B2 | 7/2007 | Richlen et al. |
| 7,297,139 | B2 | 11/2007 | Price et al. |
| 7,393,429 | B2 | 7/2008 | Tachibana |
| 7,473,818 | B2 | 1/2009 | Datta et al. |
| 7,497,852 | B2 | 3/2009 | Kawakami |
| 7,527,617 | B2 | 5/2009 | Shimada et al. |
| 7,608,068 | B2 | 10/2009 | Fujioka |
| 7,637,898 | B2 | 12/2009 | Kuen et al. |
| 7,641,641 | B2 | 1/2010 | Ramshak |
| 7,686,795 | B2 | 3/2010 | Ichikawa et al. |
| 7,708,857 | B2 | 5/2010 | Ukegawa |
| 7,789,868 | B2 | 9/2010 | Tachibana |
| 8,002,761 | B2 | 8/2011 | Utsunomiya et al. |
| 8,007,622 | B2 | 8/2011 | Heller |
| 8,034,039 | B2 | 10/2011 | Nakaoka et al. |
| 8,043,274 | B2 | 10/2011 | Mlinar et al. |
| 8,066,684 | B2 | 11/2011 | Fujioka |
| 8,066,687 | B2 | 11/2011 | Ashton et al. |
| 8,118,799 | B2 | 2/2012 | Datta et al. |
| 8,162,912 | B2 | 4/2012 | Schlinz et al. |
| 8,192,417 | B2 | 6/2012 | Kusumi et al. |
| 8,216,200 | B2 | 7/2012 | Meetz et al. |
| 8,277,430 | B2 | 10/2012 | Tabor et al. |
| 8,361,048 | B2 | 1/2013 | Kuen |
| 8,388,595 | B2 | 3/2013 | Van et al. |
| 8,557,068 | B2 | 10/2013 | Ito et al. |
| 8,569,571 | B2 | 10/2013 | Kline et al. |
| 8,657,802 | B2 | 2/2014 | Roe et al. |
| 8,663,184 | B2 | 3/2014 | Liu et al. |
| 8,753,466 | B2 | 6/2014 | Thorson |
| 8,771,449 | B2 | 7/2014 | Takino et al. |
| 8,945,324 | B2 | 2/2015 | Hahn et al. |
| 9,011,406 | B2 | 4/2015 | Torigoshi et al. |
| 9,028,462 | B2 | 5/2015 | Poole et al. |
| 9,050,217 | B2 | 6/2015 | Gassner et al. |
| 9,060,905 | B2 | 6/2015 | Wang et al. |
| 9,066,832 | B2 | 6/2015 | Gassner et al. |
| 9,066,833 | B2 | 6/2015 | Gassner |
| 9,072,632 | B2 | 7/2015 | Lavon |
| 9,089,458 | B2 | 7/2015 | Faulks et al. |
| 9,138,361 | B2 | 9/2015 | Faulks et al. |
| 9,173,781 | B2 | 11/2015 | Otsubo et al. |
| 9,226,861 | B2 | 1/2016 | Lavon |
| 9,561,138 | B2 | 2/2017 | Mukai et al. |
| 9,668,925 | B2 | 6/2017 | Mukai et al. |
| 9,750,647 | B2 | 9/2017 | Umebayashi |
| 9,789,010 | B2 | 10/2017 | Long et al. |
| 9,820,536 | B2 | 11/2017 | Sakaguchi et al. |
| 10,034,801 | B2 | 7/2018 | Seitz et al. |

(56) References Cited

U.S. PATENT DOCUMENTS

| | | | |
|---|---|---|---|
| 10,123,914 B2 | 11/2018 | Kobayashi et al. | |
| 10,188,560 B2 | 1/2019 | Mueller et al. | |
| 10,292,874 B2 | 5/2019 | Wade et al. | |
| 10,687,988 B2 | 6/2020 | Morimoto et al. | |
| 10,736,795 B2 | 8/2020 | Bianchi et al. | |
| 10,799,398 B2 | 10/2020 | Eimann et al. | |
| 10,905,602 B2 | 2/2021 | Olsson | |
| 10,993,844 B2 | 5/2021 | Olsson et al. | |
| 11,246,767 B2 | 2/2022 | Roszkowiak et al. | |
| 11,304,859 B2 | 4/2022 | Jeon et al. | |
| 11,426,312 B2 | 8/2022 | Collins et al. | |
| 11,672,708 B2 | 6/2023 | Johnson et al. | |
| 11,752,045 B2 | 9/2023 | Johnson et al. | |
| 11,883,268 B2 | 1/2024 | Johnson et al. | |
| 12,310,827 B2 | 5/2025 | Johnson et al. | |
| 2002/0032427 A1 | 3/2002 | Schmitz et al. | |
| 2002/0065503 A1 | 5/2002 | Guidotti | |
| 2002/0148557 A1 | 10/2002 | Heller | |
| 2003/0055389 A1 | 3/2003 | Sanders et al. | |
| 2003/0088223 A1 | 5/2003 | Vogt et al. | |
| 2003/0130641 A1 | 7/2003 | Richlen et al. | |
| 2003/0135191 A1* | 7/2003 | Price | A61F 13/5644 604/391 |
| 2003/0220626 A1 | 11/2003 | Karami | |
| 2004/0182502 A1 | 9/2004 | Wagner et al. | |
| 2004/0186451 A1 | 9/2004 | Bishop et al. | |
| 2004/0193135 A1 | 9/2004 | Van | |
| 2005/0148974 A1 | 7/2005 | Datta et al. | |
| 2005/0177125 A1 | 8/2005 | Kondo | |
| 2005/0192553 A1 | 9/2005 | Hasler et al. | |
| 2006/0129119 A1 | 6/2006 | Kistler | |
| 2006/0135936 A1 | 6/2006 | Markovich et al. | |
| 2006/0293639 A1 | 12/2006 | Van | |
| 2008/0015534 A1 | 1/2008 | Kusumi et al. | |
| 2008/0103470 A1 | 5/2008 | Samuelsson et al. | |
| 2008/0114322 A1 | 5/2008 | Schmoker et al. | |
| 2008/0134487 A1 | 6/2008 | Hartono | |
| 2008/0154223 A1 | 6/2008 | Fujioka | |
| 2008/0249493 A1 | 10/2008 | Kobayashi et al. | |
| 2009/0149827 A1 | 6/2009 | Mlinar et al. | |
| 2009/0312734 A1 | 12/2009 | Lavon et al. | |
| 2011/0098668 A1 | 4/2011 | Thorson | |
| 2011/0155304 A1 | 6/2011 | Sakaguchi | |
| 2013/0012905 A1 | 1/2013 | Katsuragawa et al. | |
| 2013/0231625 A1 | 9/2013 | Ellefson et al. | |
| 2013/0306226 A1 | 11/2013 | Zink | |
| 2014/0110037 A1 | 4/2014 | Verboomen | |
| 2014/0113792 A1 | 4/2014 | Verboomen et al. | |
| 2014/0114272 A1 | 4/2014 | Schoon et al. | |
| 2014/0135730 A1 | 5/2014 | Mlinar et al. | |
| 2014/0155855 A1 | 6/2014 | Romzek et al. | |
| 2014/0187405 A1 | 7/2014 | Volp et al. | |
| 2016/0262952 A1* | 9/2016 | Wade | A61F 13/49061 |
| 2017/0105883 A1 | 4/2017 | Nishikawa et al. | |
| 2017/0266941 A1 | 9/2017 | Eimann | |
| 2019/0099304 A1 | 4/2019 | Berry | |
| 2019/0209392 A1 | 7/2019 | Johnson et al. | |
| 2020/0163810 A1 | 5/2020 | Johnson et al. | |
| 2021/0093485 A1 | 4/2021 | Ljungberg et al. | |
| 2021/0369510 A1 | 12/2021 | Ljungberg et al. | |
| 2023/0127980 A1 | 4/2023 | Umebayashi | |
| 2023/0146261 A1 | 5/2023 | Seitz et al. | |
| 2024/0173175 A1 | 5/2024 | Johnson et al. | |

FOREIGN PATENT DOCUMENTS

| | | | |
|---|---|---|---|
| EP | 0570980 B1 | 7/1997 | |
| EP | 0705088 B1 | 5/1999 | |
| EP | 1027874 A2 | 8/2000 | |
| EP | 0955976 B1 | 3/2002 | |
| EP | 1128790 B1 | 5/2003 | |
| EP | 1779827 A1 | 5/2007 | |
| EP | 2486905 B1 | 4/2017 | |
| EP | 3053562 B1 | 3/2022 | |
| JP | 3209377 B2 | 9/2001 | |
| JP | 2001258938 A | 9/2001 | |
| JP | 2002017778 A | 1/2002 | |
| JP | 3429383 B2 | 7/2003 | |
| JP | 2003290286 A | 10/2003 | |
| JP | 3578802 B2 | 7/2004 | |
| JP | 2004329590 A | 11/2004 | |
| JP | 3737709 B2 | 11/2005 | |
| JP | 2006034402 A | 2/2006 | |
| JP | 2006055343 A | 3/2006 | |
| JP | 2006068211 A | 3/2006 | |
| JP | 2006204385 A | 8/2006 | |
| JP | 4037216 B2 | 11/2007 | |
| JP | 4090913 B2 | 3/2008 | |
| JP | 4131683 B2 | 6/2008 | |
| JP | 2008142345 A | 6/2008 | |
| JP | 4163144 B2 | 8/2008 | |
| JP | 2008302138 A | 12/2008 | |
| JP | 4240464 B2 | 1/2009 | |
| JP | 4260711 B2 | 2/2009 | |
| JP | 4276556 B2 | 3/2009 | |
| JP | 4280187 B2 | 3/2009 | |
| JP | 4312084 B2 | 5/2009 | |
| JP | 4444078 B2 | 1/2010 | |
| JP | 4444079 B2 | 1/2010 | |
| JP | 4502882 B2 | 4/2010 | |
| JP | 4508892 B2 | 5/2010 | |
| JP | 4511284 B2 | 5/2010 | |
| JP | 2010136787 A | 6/2010 | |
| JP | 2010246901 A | 11/2010 | |
| JP | 4672651 B2 | 1/2011 | |
| JP | 4682085 B2 | 2/2011 | |
| JP | 4745119 B2 | 5/2011 | |
| JP | 4758821 B2 | 6/2011 | |
| JP | 4801498 B2 | 8/2011 | |
| JP | 4908255 B2 | 1/2012 | |
| JP | 4926742 B2 | 2/2012 | |
| JP | 5009040 B2 | 6/2012 | |
| JP | 5014452 B2 | 8/2012 | |
| JP | 5106253 B2 | 10/2012 | |
| JP | 5107447 B2 | 10/2012 | |
| JP | 2013052228 A | 3/2013 | |
| JP | 5241457 B2 | 4/2013 | |
| JP | 5244226 B2 | 4/2013 | |
| JP | 5352408 B2 | 8/2013 | |
| JP | 5438952 B2 | 12/2013 | |
| JP | 5568369 B2 | 6/2014 | |
| JP | 5572822 B2 | 7/2014 | |
| JP | 5632346 B2 | 10/2014 | |
| JP | 5632521 B2 | 10/2014 | |
| JP | 5638305 B2 | 10/2014 | |
| JP | 5728907 B2 | 4/2015 | |
| JP | 5868105 B2 | 1/2016 | |
| JP | 2016140420 A | 8/2016 | |
| JP | 6024486 B2 | 11/2016 | |
| JP | 6159109 B2 | 6/2017 | |
| JP | 6176958 B2 | 7/2017 | |
| JP | 6180025 B2 | 7/2017 | |
| JP | 6298274 B2 | 3/2018 | |
| JP | 2018139718 A | 9/2018 | |
| JP | 6429710 B2 | 11/2018 | |
| JP | 2018187217 A | 11/2018 | |
| JP | 6913131 B2 | 7/2021 | |
| JP | 6941026 B2 | 9/2021 | |
| JP | 7315360 B2 | 3/2023 | |
| JP | 2023042747 A | 3/2023 | |
| WO | 2009084643 A1 | 7/2009 | |
| WO | 2014080795 A1 | 5/2014 | |
| WO | 2014196215 A1 | 12/2014 | |
| WO | 2015046632 A1 | 4/2015 | |
| WO | 2016013662 A1 | 1/2016 | |
| WO | 2016104753 A1 | 6/2016 | |
| WO | 2016121236 A1 | 8/2016 | |
| WO | 2018207512 A1 | 11/2018 | |
| WO | 2020062132 A1 | 4/2020 | |
| WO | 2020195099 A1 | 10/2020 | |
| WO | 2021241553 A1 | 12/2021 | |
| WO | 2022004727 A1 | 1/2022 | |

(56)               References Cited

FOREIGN PATENT DOCUMENTS

OTHER PUBLICATIONS

All Office Actions; U.S. Appl. No. 18/214,564, filed on Jun. 27, 2023.
All Office Actions; U.S. Appl. No. 18/214,569, filed on Jun. 27, 2023.
All Office Actions; U.S. Appl. No. 18/214,573, filed on Jun. 27, 2023.
All Office Actions; U.S. Appl. No. 18/214,586, filed on Jun. 27, 2023.
All Office Actions; U.S. Appl. No. 18/214,603, filed on Jun. 27, 2023.
All Office Actions; U.S. Appl. No. 18/214,680, filed on Jun. 27, 2023.
All Office Actions; U.S. Appl. No. 18/214,691, filed on Jun. 27, 2023.
All Office Actions; U.S. Appl. No. 18/214,718, filed on Jun. 27, 2023.
All Office Actions; U.S. Appl. No. 18/214,750, filed on Jun. 27, 2023.
All Office Actions; U.S. Appl. No. 18/342,054, filed on Jun. 27, 2023.
All Office Actions; U.S. Appl. No. 18/342,058, filed on Jun. 27, 2023.
U.S. Appl. No. 18/214,548, filed on Jun. 27, 2023, to Jeromy Thomas Raycheck et al.
U.S. Appl. No. 18/214,564, filed on Jun. 27, 2023, to Uwe Schneider et al.
U.S. Appl. No. 18/214,569, filed on Jun. 27, 2023, to Keith Richard Willhaus et al.
U.S. Appl. No. 18/214,573, filed on Jun. 27, 2023, to Jeromy Thomas Raycheck et al.
U.S. Appl. No. 18/214,586, filed on Jun. 27, 2023, to Keith Richard Willhaus et al.
U.S. Appl. No. 18/214,603, filed on Jun. 27, 2023, to Keith Richard Willhaus et al.
U.S. Appl. No. 18/214,680, filed on Jun. 27, 2023, to Jeromy Thomas Raycheck et al.
U.S. Appl. No. 18/214,691, filed on Jun. 27, 2023, to Uwe Schneider et al.
U.S. Appl. No. 18/214,718, filed on Jun. 27, 2023, to Keith Richard Willhaus et al.
U.S. Appl. No. 18/214,750, filed on Jun. 27, 2023, to Jeffry Rosiak et al.
U.S. Appl. No. 18/342,054, filed on Jun. 27, 2023, to Nicholas Alexander Taylor et al.
U.S. Appl. No. 18/342,058, filed on Jun. 27, 2023, to Han Xu et al.
PCT Search Report and Written Opinion for PCT/US2023/069120 daled Sep. 21, 2023, 12 pages.
All Office Actions; U.S. Appl. No. 18/967,797, filed on Dec. 4, 2024; See Patent Center.
All Office Actions; U.S. Appl. No. 18/967,768, filed on Dec. 4, 2024; See Patent Center.
All Office Actions; U.S. Appl. No. 18/967,824, filed on Dec. 4, 2024; See Patent Center.
All Office Actions; U.S. Appl. No. 18/968,031, filed on Dec. 4, 2024; See Patent Center.
All Office Actions; U.S. Appl. No. 18/978,059, filed on Dec. 12, 2024; See Patent Center.
U.S. Appl. No. 18/967,797, filed on Dec. 4, 2024, Kaitlyn Nicole Taylor et al. See Patent Center.
U.S. Appl. No. 18/967,768, filed on Dec. 4, 2024, Keith Richard Willhaus et al. See Patent Center.
U.S. Appl. No. 18/967,824, filed on Dec. 4, 2024, Jeffry Rosiak et al. See Patent Center.
U.S. Appl. No. 18/968,031, filed on Dec. 4, 2024, Keith Richard Willhaus et al. See Patent Center.
U.S. Appl. No. 18/978,059, filed on Dec. 12, 2024, Jeromy Thomas Raycheck et al. See Patent Center.

* cited by examiner

Fig. 3A1

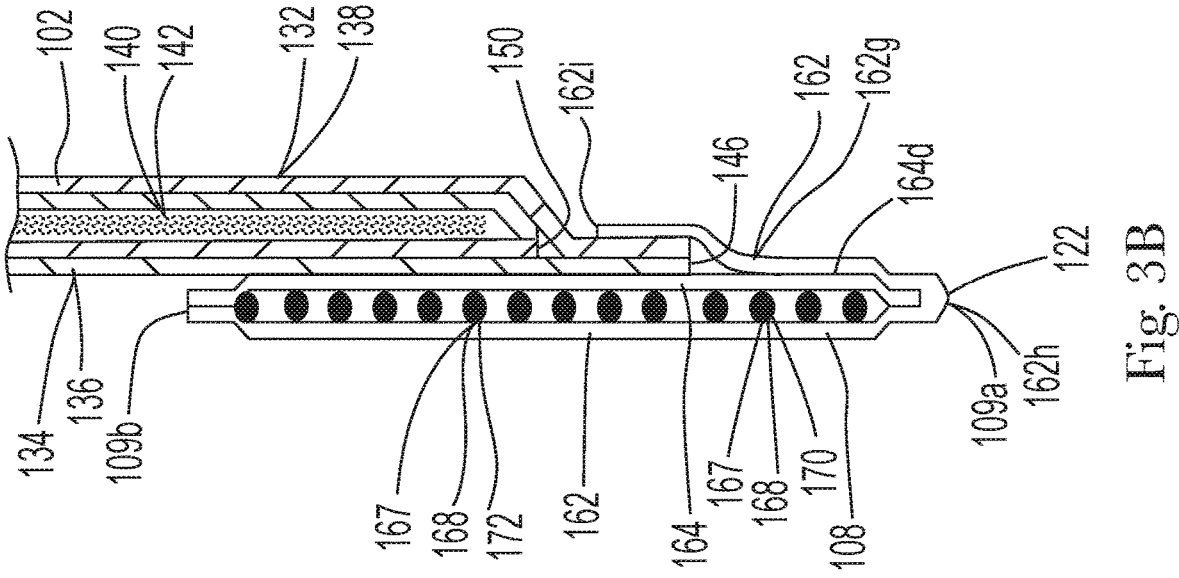
Fig. 3B
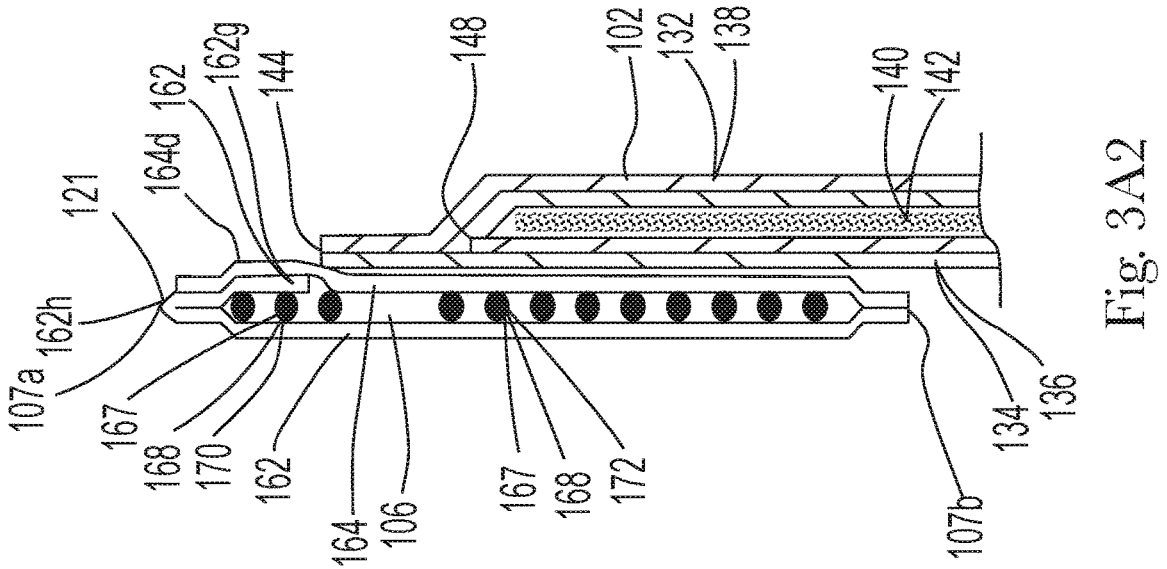
Fig. 3A2

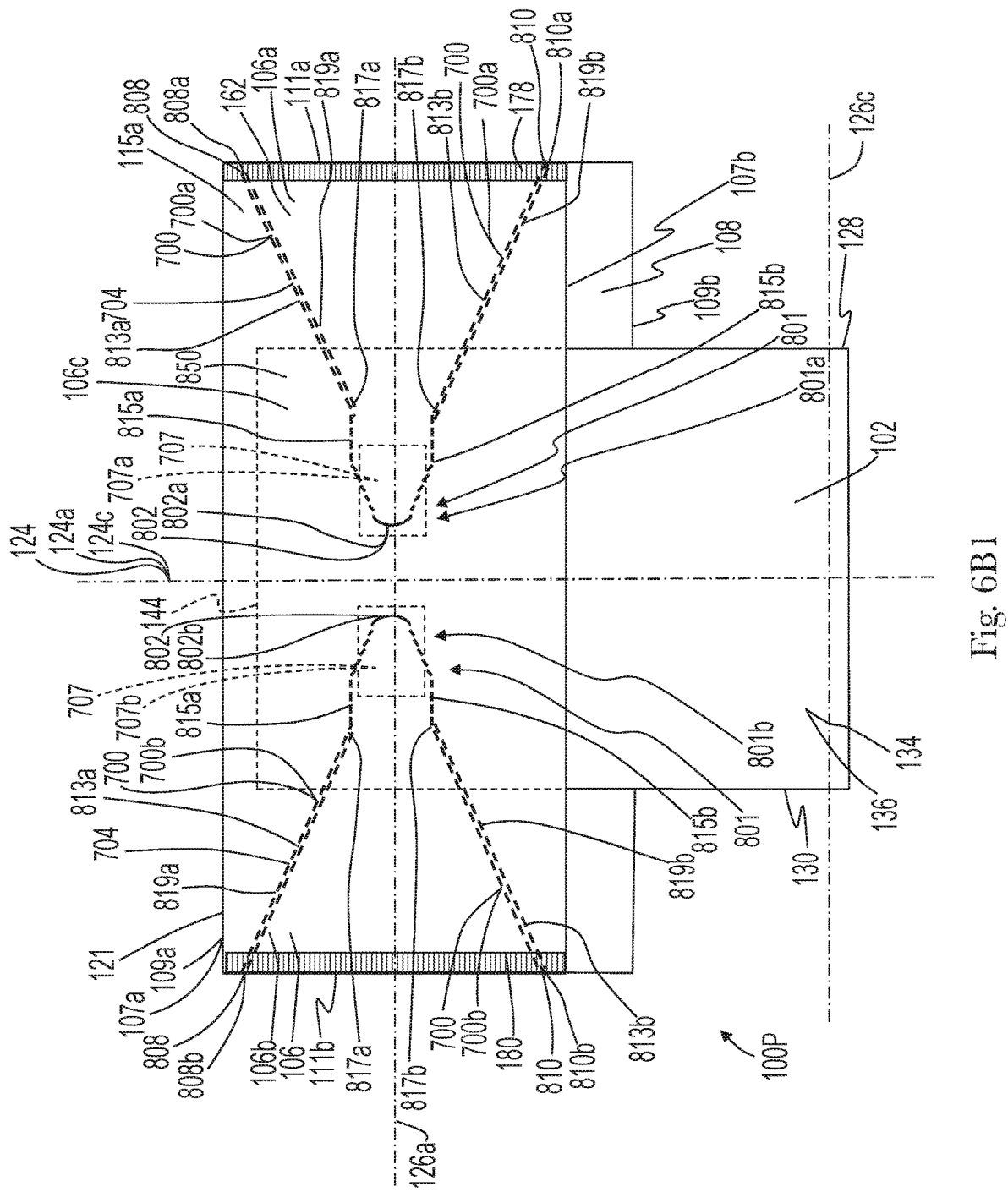
Fig. 6B1

ABSORBENT ARTICLES WITH FRANGIBLE PATHWAYS ADAPTED FOR TEAR PROPAGATION BETWEEN REGIONS OF LAMINATES HAVING DIFFERENT NUMBERS OF LAYERS OF SUBSTRATES

CROSS REFERENCE TO RELATED APPLICATION

This application claims the benefit, under 35 USC 119(e), of U.S. Provisional Patent Application No. 63/432,410 filed on Dec. 14, 2022; U.S. Provisional Patent Application No. 63/357,043, filed on Jun. 30, 2022; U.S. Provisional Patent Application No. 63/432,400, filed on Dec. 14, 2022; U.S. Provisional Patent Application No. 63/432,401, filed on Dec. 14, 2022; U.S. Provisional Patent Application No. 63/432,402, filed on Dec. 14, 2022; U.S. Provisional Patent Application No. 63/432,403, filed on Dec. 14, 2022; U.S. Provisional Patent Application No. 63/432,404, filed on Dec. 14, 2022; U.S. Provisional Patent Application No. 63/432,406, filed on Dec. 14, 2022; and U.S. Provisional Patent Application No. 63/432,413, filed on Dec. 14, 2022, each of which are herein incorporated by reference in their entirety.

FIELD OF THE INVENTION

The present disclosure relates to absorbent articles, and more particularly, to absorbent articles having front and/or back waist regions including one or more frangible pathways.

BACKGROUND OF THE INVENTION

Some absorbent articles have components that include elastomeric laminates. Such elastomeric laminates may include an elastic material bonded to one or more nonwovens. The elastic material may include an elastic film and/or elastic strands. In some laminates, a plurality of elastic strands are joined to a nonwoven while the plurality of strands are in a stretched condition so that when the elastic strands relax, the nonwoven gathers, and in turn, forms corrugations and rugosities. The resulting elastomeric laminate is stretchable to the extent that the corrugations allow the elastic strands to elongate.

Absorbent articles in the form of diaper pants may also be configured with an absorbent chassis connected with front and back elastic belts, wherein opposing end regions of the front and back belts are connected with each other at side seams. In some instances, the elasticity of the front and back belts is removed in regions where the chassis connects with the belts. Thus, in some converting configurations adapted to assemble such diaper pants, stretched elastic strands are glued between two continuous nonwoven webs to form an elastic laminate. Regions of the elastic strands may then be intermittently deactivated along the length of the elastic laminate by cutting the elastic strands in areas to be connected with the chassis, sometimes referred to as tummy elastic cutting.

Some caregivers of older incontinent babies or toddlers may prefer a closed, pant-style disposable absorbent article to enable application to, and removal from, a child while the child is in a standing position. One disadvantage of this product form is that the removal and disposal of feces-containing products may be unhygienic and inconvenient. For example, pulling the product down could cause feces to smear down the legs of a user. In other examples, a caregiver may tear open the bonded sides using force. In turn, the force used can lead to a rapid release of energy from the diaper, causing the caregiver to lose control of the product and allowing feces to spill out. In contrast, removal and disposal of traditional open or taped diaper forms with fasteners may be readily accomplished while the child is laying on their back. In this case, the fasteners are opened, the diaper is removed from under the child, rolled into a roughly cylindrical shape, and then the fasteners are secured around the rolled, soiled diaper, closing the leg openings for hygienic disposal.

In order to avoid having to remove soiled diaper pants from a wearer by sliding the soiled diaper pant down the wearer's legs or tearing bonded side seams, some diaper pants may be configured with tear lines in the front belt or back belt. Such tear lines may include perforations that allow a caregiver to more easily separate the belt along the perforation lines. Once the belt is separated, the diaper pant can be more easily removed from the wearer without having to slide the diaper pant down the wearer's legs, in a similar manner as a traditional open taped diaper form.

Some belts may be configured as laminates of substrate layers bonded together, and some regions of the belts may include greater numbers of substrate layers than other regions. In some configurations, a border between regions of relatively greater numbers of substrate layers and regions of relatively fewer numbers of substrate layers may be defined by an edge of a substrate layer. As such, tear lines in such belts may extend across an edge of a substrate between regions of relatively greater numbers of substrate layers and regions of relatively fewer numbers of substrate layers, which may cause difficulties for a caregiver to reliably tear the belt along the tear lines. For example, some perforations of a tear line may be arranged and/or configured such that a tear is intended to propagate from a region of relatively fewer numbers of substrate layers, across an edge of a substrate layer, and into a region of relatively greater numbers of substrate layers. In turn, due to relatively larger forces required to tear the belt across a substrate edge and through a region of relatively greater numbers of substrate layers, a tear may not continue to track the perforations at the transition between the two regions, but rather may propagate in undesired directions along the belt that require relatively less forces to continue the tear.

Consequently, it would be beneficial to create pant-style articles that provide the caregiver the ability to remove and dispose soiled products in a similar manner to traditional open diaper forms. In addition, it would be beneficial to provide diaper pants with frangible pathways configured such that the tearing operation can be completed by having a tear reliably propagate in intended directions from a region of relatively fewer numbers of substrate layers, across an edge of a substrate layer, and into a region of relatively greater numbers of substrate layers.

SUMMARY OF THE INVENTION

In one form, an absorbent article comprises: a first belt comprising an inner wearer facing surface and an outer garment facing surface, the first belt further comprising a laterally extending inner edge and a laterally extending outer edge, the outer edge positioned longitudinally outward of the inner edge, the first belt further comprising a first region and a second region, wherein the first region comprises a first number of layers of substrates and the second region comprises a second number of layers of substrates, wherein the first number of layers substrates is greater than second number of layers of substrates; a second belt, wherein laterally opposing end portions of the second belt are connected with laterally opposing end portions of the first belt at a first side seam and a second side seam to form a waist opening; a chassis comprising a topsheet, a backsheet, and an absorbent core positioned between the topsheet and the backsheet, and wherein longitudinally opposing end regions of the chassis are connected with the first belt and the second belt; and a frangible pathway in the first belt comprising first lines of weakness positioned in the first region, second lines of weakness positioned in the second region, and at least one transition line of weakness extending partially through the first region and the second region.

In another form, a method for assembling absorbent articles comprises steps of: advancing a first substrate in a machine direction, first substrate comprising a first surface and an opposing second surface, the first substrate further comprising a first edge and a second edge separated from the first edge in a cross direction; applying adhesive to the second surface of the first substrate to define a zone of adhesive extending in the machine direction; folding the first substrate along a fold line such that a first portion of the first substrate is placed in a facing relationship with a second portion of the first substrate, and wherein the first edge of the first substrate extends in the machine direction through the zone of adhesive to define a first adhesion zone and a second adhesion zone, wherein the first edge of the first substate and the first portion of the first substrate are bonded with the second portion of the first substate, and wherein the second adhesion zone extends in the cross direction from the first edge of the first substrate toward the second edge of the first substrate; providing a second substrate comprising a first surface and an opposing second surface, the second substrate further comprising a first edge and a second edge separated from the first edge in a cross direction; positioning stretched elastic strands between the first substrate and the second substrate; forming an elastic laminate by bonding the first substrate together with the second substrate, wherein first portion of the first substrate is positioned between the second surface of the first substrate and the first surface of the second substrate, and wherein the second adhesion zone bonds the second surface of the first substrate with the first surface of the second substrate, wherein the elastic laminate comprises a first region comprising a first number of layers of substrates and a second region comprising a second number of layers of substrates, wherein the first edge of the first substrate defines a border between the first region and the second region; forming a frangible pathway in the elastic laminate, the frangible pathway comprising first lines of weakness in the first region, second lines of weakness in the second region, and at least one transition line of weakness, wherein the at least one transition line of weakness extends across the first edge of the first substrate into both the first region and the second region; providing a chassis that comprises a body facing surface and a garment facing surface, and an absorbent core positioned between the body facing surface and the garment facing surface; and bonding the chassis with the elastic laminate.

In yet another form, an absorbent article comprises: a first belt comprising an inner wearer facing surface and an outer garment facing surface, the first belt further comprising a laterally extending inner edge and a laterally extending outer edge, the outer edge positioned longitudinally outward of the inner edge, the first belt further comprising a first region and a second region, wherein the first region comprises a first number of layers of substrates and the second region comprises a second number of layers of substrates, wherein the first number of layers substrates is greater than second number of layers of substrates; wherein the first substrate comprises a laterally extending first edge, a laterally extending second edge, a first surface and an opposing second surface, wherein the second substrate comprises a laterally extending first edge, a laterally extending second edge, a first surface and an opposing second surface, wherein the second surface of the first substrate is in a facing relationship with the first surface of the second substrate, wherein the first substrate is folded along a fold line such that a first portion of the first substrate is in a facing relationship with a second portion of the first substrate, and wherein the first portion extends longitudinally between the fold line and the first edge of the first substrate, and wherein the second portion extends longitudinally between the fold line and the second edge of the first substrate; wherein the first edge of the first substrate extends laterally through a zone of adhesive to define a first adhesion zone and a second adhesion zone, the first adhesion zone extending longitudinally from the first edge of the first substrate toward the fold line and the second adhesion zone extending longitudinally from the first edge of the first substrate away from the fold line; a second belt, wherein laterally opposing end portions of the second belt are connected with laterally opposing end portions of the first belt at a first side seam and a second side seam to form a waist opening; a chassis comprising a topsheet, a backsheet, and an absorbent core positioned between the topsheet and the backsheet, and wherein longitudinally opposing end regions of the chassis are connected with the first belt and the second belt; and a frangible pathway in the first belt comprising lines of weakness positioned in the first region and the second region.

BRIEF DESCRIPTION OF THE DRAWINGS

FIG. 3A1 is a cross-sectional detailed view of another example configuration wherein the first belt is provided with panel layers wherein one panel layer is folded over another panel layer.

FIG. 3A2 is a cross-sectional detailed view of another example configuration wherein the first belt is provided with panel layers wherein one panel layer is folded over another panel layer.

FIG. 3B is a cross-sectional detailed view of a second belt provided with panel layers wherein one panel layer is folded over another panel layer.

FIG. 6B1 is a front plan view of another configuration of a diaper pant with frangible pathways having a distal terminus and a proximal terminus positioned on a side seams.

FIG. 8AA1 is a cross-sectional view of the fastener component of FIG. 8A taken along line 8AA-8AA.

FIG. 8AA2 is a cross-sectional view of the fastener component of FIG. 8A taken along line 8AA-8AA, wherein the fastener component is integrally formed from belt components.

DETAILED DESCRIPTION OF THE INVENTION

Definitions

Figure 1:
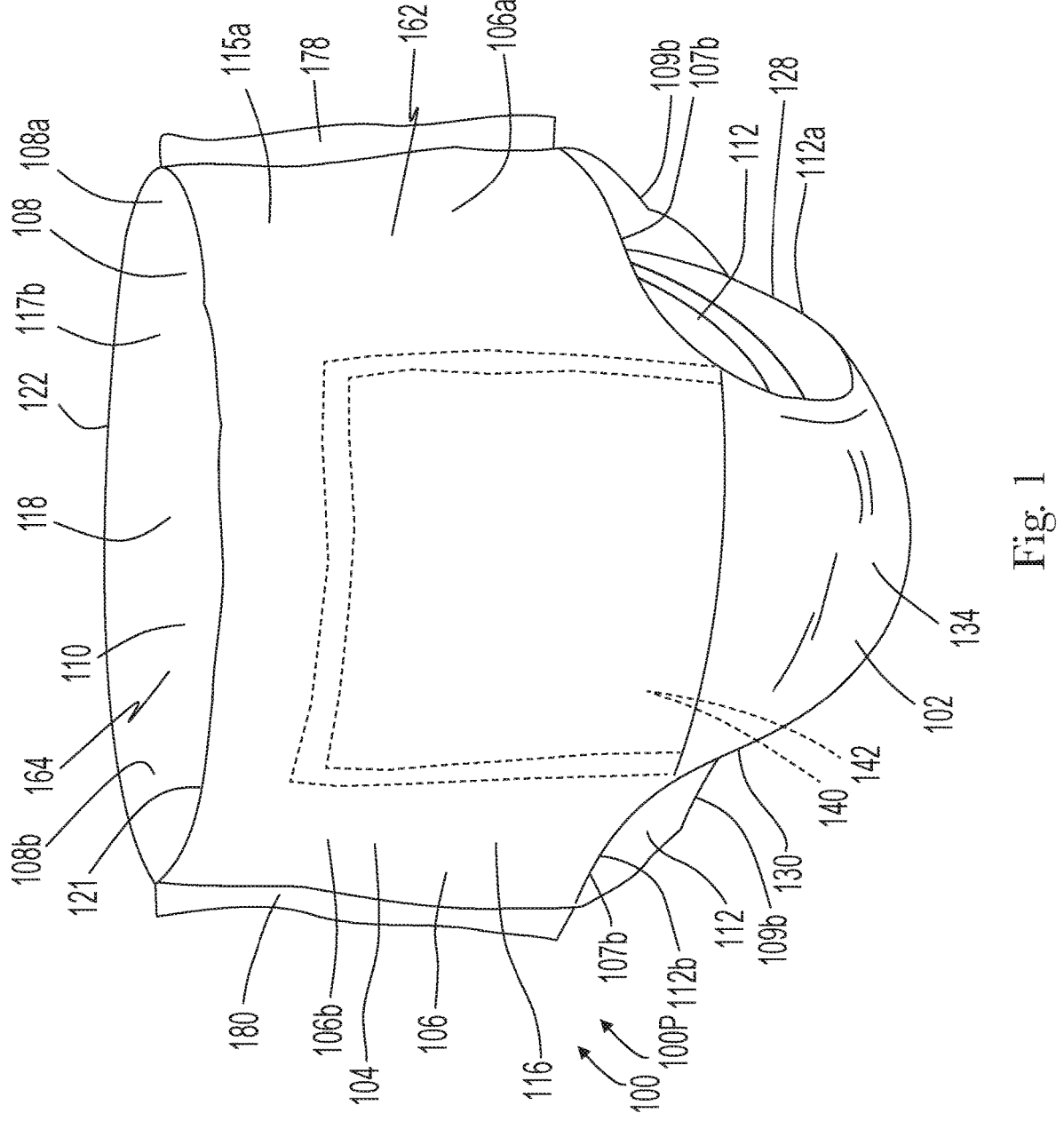
FIG. 1 shows a perspective view of a diaper pant in a pre-fastened configuration.

The following term explanations may be useful in understanding the present disclosure:

"Absorbent article" refers to devices, which absorb and contain body exudates and, more specifically, refers to devices, which are placed against or in proximity to the body of the wearer to absorb and contain the various exudates discharged from the body. Exemplary absorbent articles include diapers, training pants, pull-on pant-type diapers (i.e., a diaper having a preformed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, menstrual pads and the like.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

The terms "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. Elastomeric materials may include elastomeric films, scrims, nonwovens, ribbons, strands and other sheet-like structures.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "distal" is used to describe a position situated away from a center of a body or from a point of attachment, and the term "proximal" is used to describe a position situated nearer to a center of a body or a point of attachment.

The term "substrate" is used herein to describe a material which is primarily two-dimensional (i.e., in an XY plane) and whose thickness (in a Z direction) is relatively small (i.e., $\frac{1}{10}$ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

"Pre-strain" refers to the strain imposed on an elastic or elastomeric material prior to combining it with another element of the elastomeric laminate or the absorbent article. Pre-strain is determined by the following equation Pre-strain=((extended length of the elastic-relaxed length of the elastic)/relaxed length of the elastic)*100.

"Decitex" also known as Dtex is a measurement used in the textile industry used for measuring yarns or filaments. 1 Decitex=1 gram per 10,000 meters. In other words, if 10,000 linear meters of a yarn or filament weights 500 grams that yarn or filament would have a decitex of 500.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674, 216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, back waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

"Closed-form" means opposing waist regions are joined, as packaged, either permanently or refastenably to form a continuous waist opening and leg openings.

"Open-form" means opposing waist regions are not initially joined to form a continuous waist opening and leg openings but comprise a closure means such as a fastening system to join the waist regions to form the waist and leg openings before or during application to a wearer of the article.

The present disclosure relates to absorbent articles including elastic laminates, and more particularly, to absorbent articles having elastic laminates in front and/or back waist regions with frangible pathways. In some configurations, an absorbent article may comprise: a first belt and a second belt, each belt comprising a first end region and a second end region laterally separated from the first end region by a central region. The first end region of the first belt is connected with the first end region of the second belt and the second end region of the first belt is connected with the second end region of the second belt to form a waist opening. The absorbent article may further comprise a chassis comprising a topsheet, a backsheet, and an absorbent core positioned between the topsheet and the backsheet. The chassis may further comprise a first end region and a second end region longitudinally separated from the first end region by a crotch region. The first end region of the chassis may be connected with the central region of the first belt and the second end region of the chassis may be connected with the central region of the second belt. The first belt may further comprise a laterally extending inner edge and a laterally extending outer edge, the outer edge positioned longitudinally outward of the inner edge.

As discussed in more detail below, the first belt and/or the second belt may comprise a first region and a second region, wherein the first region comprises a first number of layers of substrates and the second region comprises a second number of layers of substrates, wherein the first number of layers substrates is greater than second number of layers of substrates. In addition, the first belt and/or the second belt may comprise one or more frangible pathways comprising first lines of weakness positioned in the first region, second lines of weakness positioned in the second region, and at least one transition line of weakness extending partially through the first region and the second region.

In some configurations, the first and/or second belt may comprise a first substrate and a second substrate. The first substrate may comprise a laterally extending first edge, a laterally extending second edge, a first surface and an opposing second surface. And the second substrate may comprise a laterally extending first edge, a laterally extending second edge, a first surface and an opposing second surface. The second surface of the first substrate may be in a facing relationship with the first surface of the second substrate. The first substrate is folded along a fold line such that a first portion of the first substrate is in a facing relationship with a second portion of the first substrate. The first portion extends longitudinally between the fold line and the first edge of the first substrate, and the second portion extends longitudinally between the fold line and the second edge of the first substrate. The first edge of the first substrate may extend laterally through a zone of adhesive. In turn, the at least one transition line of weakness extends across the zone of adhesive and severs the first edge of the first substrate. As discussed in more detail below, having the first edge of the first substrate reliably severed by a line of weakness and reliably adhered to another substrate layer helps to ensure that a tear will propagate along the lines of weakness without unintentionally propagating in undesired directions along the belt.

Figure 2A:
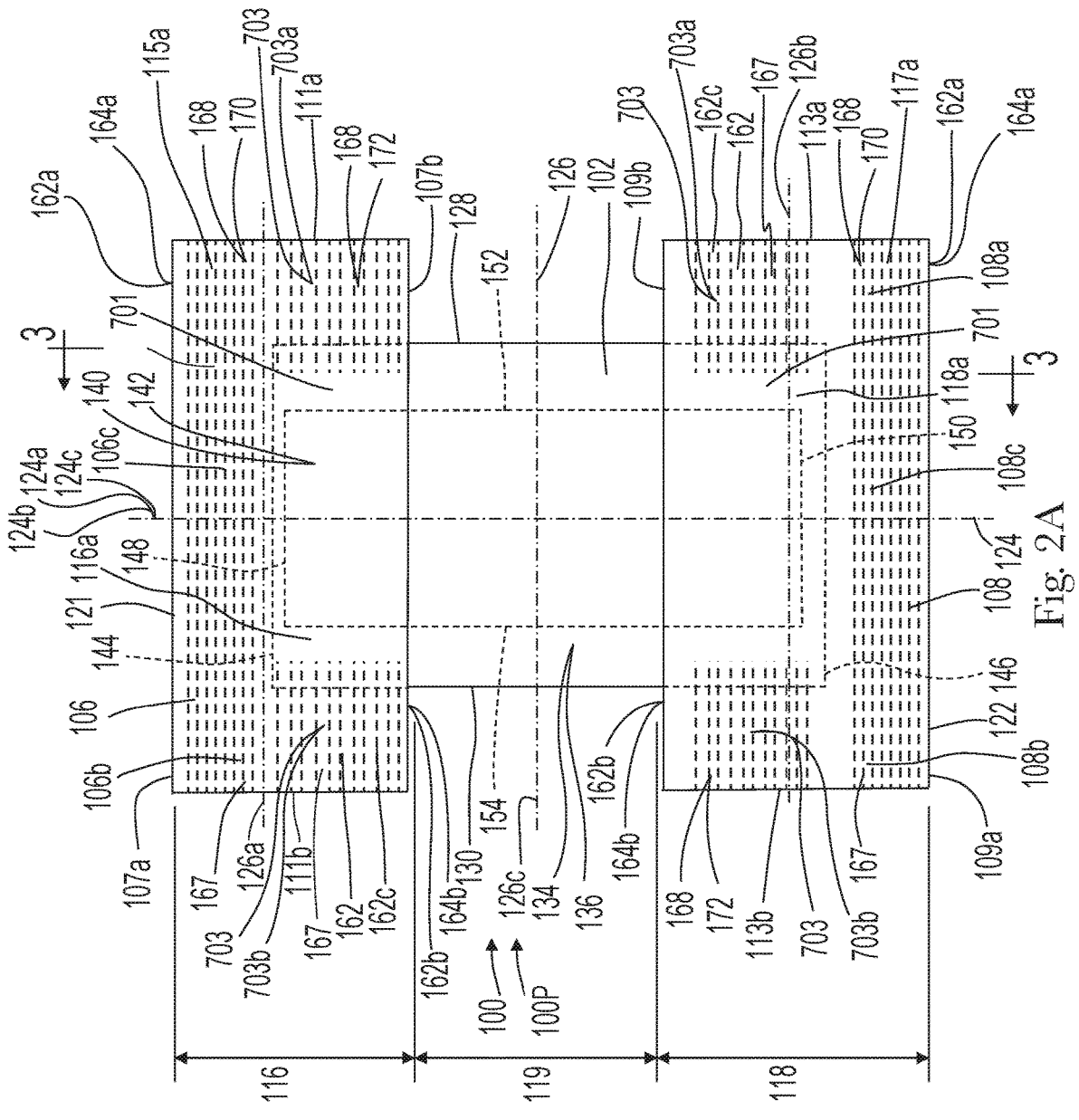
FIG. 2A shows a plan view of a diaper pant with the portion of the diaper that faces away from a wearer oriented toward the viewer.
Figure 2B:
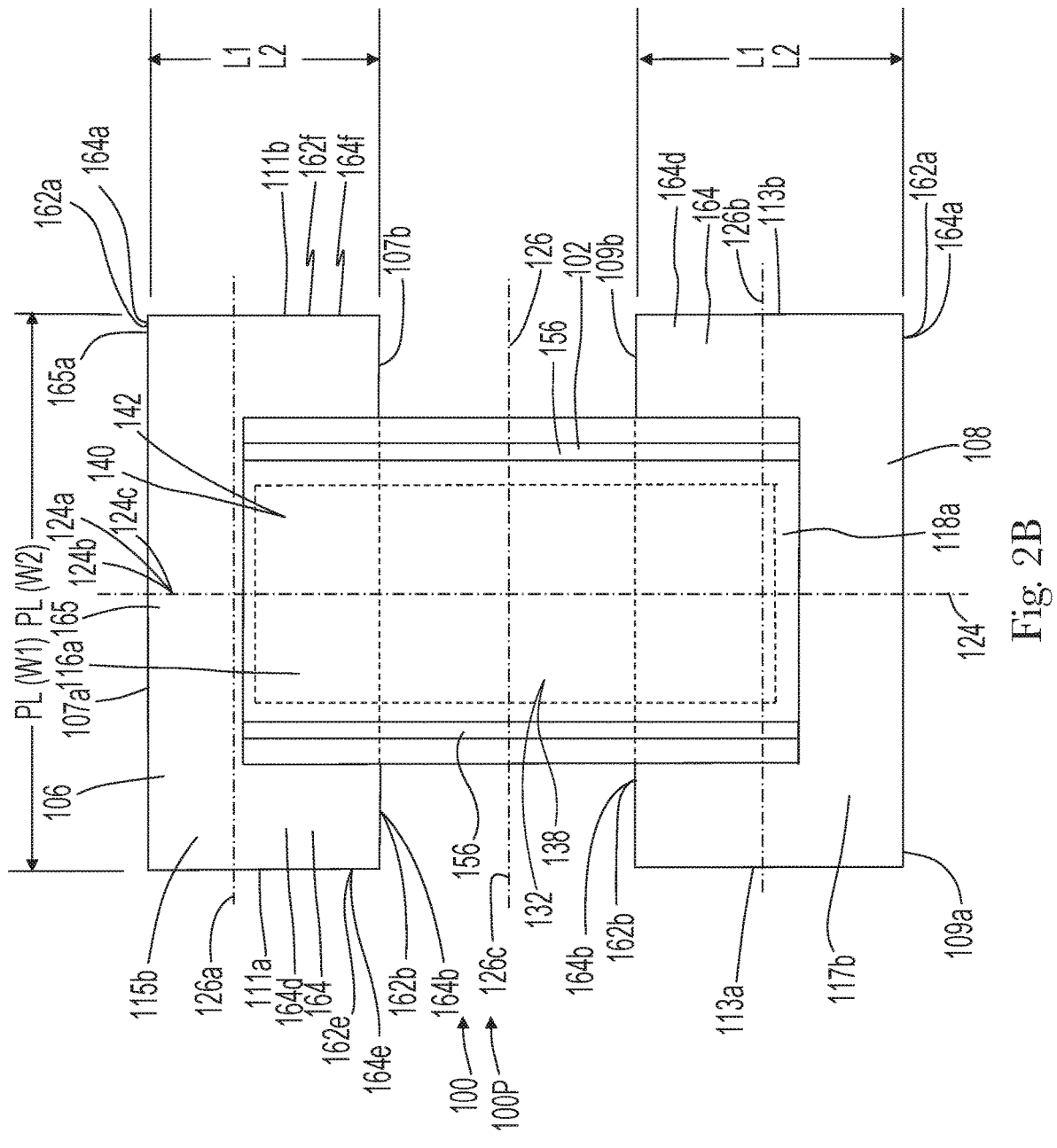
FIG. 2B shows a plan view of a diaper pant with the portion of the diaper that faces toward a wearer oriented toward the viewer.

FIGS. 1-2B show an example of an absorbent article 100 in the form of a diaper pant 100P that may include components constructed in accordance with the configurations disclosed herein. In particular, FIG. 1 shows a perspective views of a diaper pant 100P in a pre-fastened configuration. FIG. 2A shows a plan view of the diaper pant 100P with the portion of the diaper that faces away from a wearer oriented toward the viewer, and FIG. 2B shows a plan view of the diaper pant 100P with the portion of the diaper that faces toward a wearer oriented toward the viewer. The diaper pant 100P includes a chassis 102 and a ring-like elastic belt 104. As discussed below in more detail, a first elastic belt 106 and a second elastic belt 108 are bonded together to form the ring-like elastic belt 104.

With continued reference to FIGS. 1-2B, the diaper pant 100P and the chassis 102 each include a first waist region 116, a second waist region 118, and a crotch region 119 disposed intermediate the first and second waist regions. It may also be described that the chassis 102 includes a first end region 116a, a second end region 118a, and a crotch region 119 disposed intermediate the first and second end regions 116a, 118a. The first waist region 116 may be configured as a front waist region, and the second waist region 118 may be configured as back waist region. The diaper 100P may also include a laterally extending front waist edge 121 in the front waist region 116 and a longitudinally opposing and laterally extending back waist edge 122 in the back waist region 118. To provide a frame of reference for the present discussion, the diaper 100P and chassis 102 of FIGS. 2A and 2B are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a second longitudinal or left side edge 130 of the chassis 102. As previously mentioned, the longitudinal axis 124 extends perpendicularly through the front waist edge 121 and the back waist edge 122, and the lateral axis 126 extends perpendicularly to the longitudinal axis 124. When the diaper pant 100P is worn, the longitudinal direction may extend from the wearer's front waist, through the crotch, to the wearer's back waist. To provide a further frame of reference for the present discussion, the diapers 100P of FIGS. 2A, 2B, and 18B are shown wherein: the first elastic belt 106 comprises a longitudinal centerline 124a and lateral centerline 126a; the second elastic belt 108 comprises a longitudinal centerline 124b and lateral centerline 126b; and the chassis 102 comprises a longitudinal centerline 124c and lateral centerline 126c. The longitudinal centerlines 124a, 124b, 124c are perpendicular to the lateral center lines 126a, 126b, 126c.

As shown in FIGS. 1-2B, the diaper pant 100P may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100P may also include other features, such as leg elastics and/or leg cuffs to enhance the fit around the legs of the wearer.

As shown in FIG. 2A, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 may be located longitudinally inward from the laterally extending front waist edge 121 in the front waist region 116 and the laterally extending back waist edge 122 in the back waist region 118. In some configurations, the laterally extending end edges 144 and 146 may be coterminous with or located longitudinally outward from the laterally extending front waist edge 121 in the front waist region 116 and the laterally extending back waist edge 122 in the back waist region 118. When the diaper pant 100P is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

As previously mentioned, the diaper pant 100P may include a backsheet 136. The backsheet 136 may also define the outer, garment facing surface 134 of the chassis 102. The backsheet 136 may also comprise a woven or nonwoven material, polymeric films such as thermoplastic films of polyethylene or polypropylene, and/or a multi-layer or composite materials comprising a film and a nonwoven material. The backsheet may also comprise an elastomeric film. An example backsheet 136 may be a polyethylene film having a thickness of from about 0.012 mm (0.5 mils) to about 0.051 mm (2.0 mils). Further, the backsheet 136 may permit vapors to escape from the absorbent core (i.e., the backsheet is breathable) while still preventing exudates from passing through the backsheet 136.

Also described above, the diaper pant 100P may include a topsheet 138. The topsheet 138 may also define all or part of the inner, wearer facing surface 132 of the chassis 102. The topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art. Topsheets 138 may be selected from high loft nonwoven topsheets, apertured film topsheets and apertured nonwoven topsheets. Exemplary apertured films may include those described in U.S. Pat. Nos. 5,628,097; 5,916,661; 6,545, 197; and 6,107,539, all of which are incorporated by reference herein.

As mentioned above, the diaper pant 100P may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834, 735, all of which are incorporated by reference herein.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 A1 and 2004/ 0097895 A1, all of which are incorporated by reference herein.

As previously mentioned, the diaper 100P may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695, 278; 4,795,454; 4,704,115; 4,909,803; and U.S. Patent Publication No. 2009/0312730 A1, all of which are incorporated by reference herein.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening

110 and continuous perimeter leg openings 112 such as shown in FIG. 1. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIGS. 2A and 2B, the first elastic belt 106 extends between a first longitudinal side edge 111a and a second longitudinal side edge 111b and defines first and second opposing end regions 106a, 106b and a central region 106c. And the second elastic 108 belt extends between a first longitudinal side edge 113a and a second longitudinal side edge 113b and defines first and second opposing end regions 108a, 108b and a central region 108c. As measured in an extended state, the distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 or first end region 116a of the chassis 102, and the central region 108c of the second elastic belt 108 is connected with the second waist region 118 or second end region 118a of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112. It is to be appreciated that the first belt 106 and the second belt 108 may be permanently or refastenably connected with each other at the first side seam 178 and the second side seam 180. The side seams 178, 180 may comprise a permanent bond, such as a thermal, pressure, or adhesive bond, or may be a releasable bond, such as a mechanical or cohesive fastener.

As shown in FIGS. 2A and 2B, the first elastic belt 106 also defines an outer laterally extending edge 107a and an inner laterally extending edge 107b, and the second elastic belt 108 defines an outer laterally extending edge 109a and an inner laterally extending edge 109b. The outer edge 107a of the first belt 106 is positioned longitudinally outward of the inner edge 107b, and the outer edge 109a of the second belt 108 is positioned longitudinally outward of the inner edge 109b. As such, as shown in FIG. 1, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b, the inner laterally extending edge 109b, and the second longitudinal or left side edge 130 of the chassis 102. The outer laterally extending edges 107a, 109a may also define the front waist edge 121 and the laterally extending back waist edge 122 of the diaper pant 100P.

It is to be appreciated that the first elastic belt 106 and the second elastic belt 108 may define different sizes and shapes. In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168 that extend along non-linear or curved paths that may correspond with the curved contours of the inner lateral edges 107*b*, 109*b*.

Figure 2C:
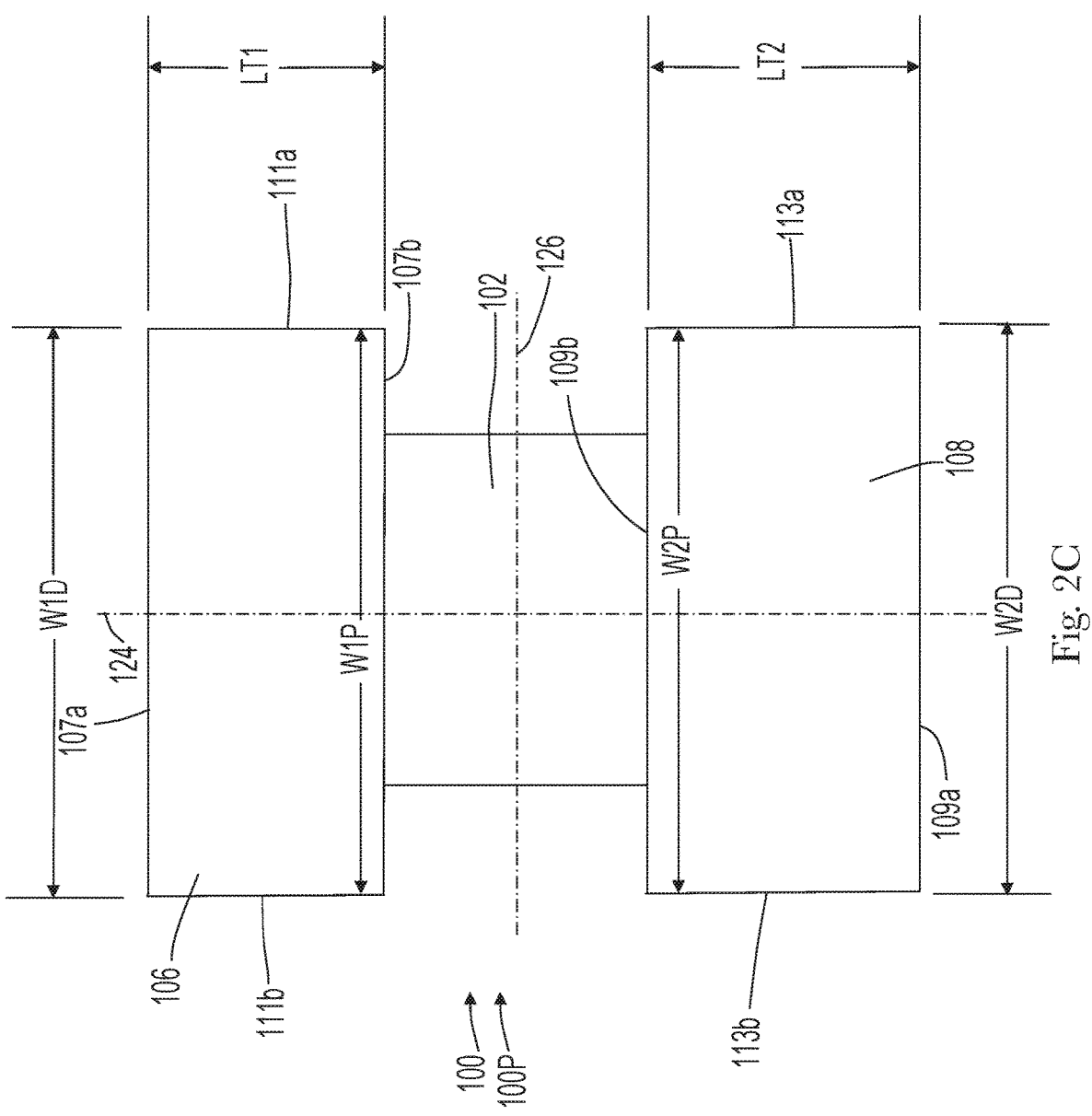
FIG. 2C shows a plan view of a diaper pant with the portion of the diaper that faces away from a wearer oriented toward the viewer, illustrating first and second belt size and shape features.

FIG. 2C shows a configuration wherein the first elastic belt 106 and the second elastic belt 108 both define generally rectangular shapes. For example, as shown in FIG. 2C, the outer laterally extending edge 107*a* of the first elastic belt 106 may comprise a lateral width of W1D and the inner laterally extending edge 107*b* may comprise a lateral width of W1P, wherein W1D and W1P are equal or substantially equal. In addition, the outer laterally extending edge 109*a* of the second elastic belt 108 may comprise a lateral width of W2D and the inner laterally extending edge 109*b* may comprise a lateral width of W2P, wherein W2D and W2P are equal or substantially equal.

Figure 2D:
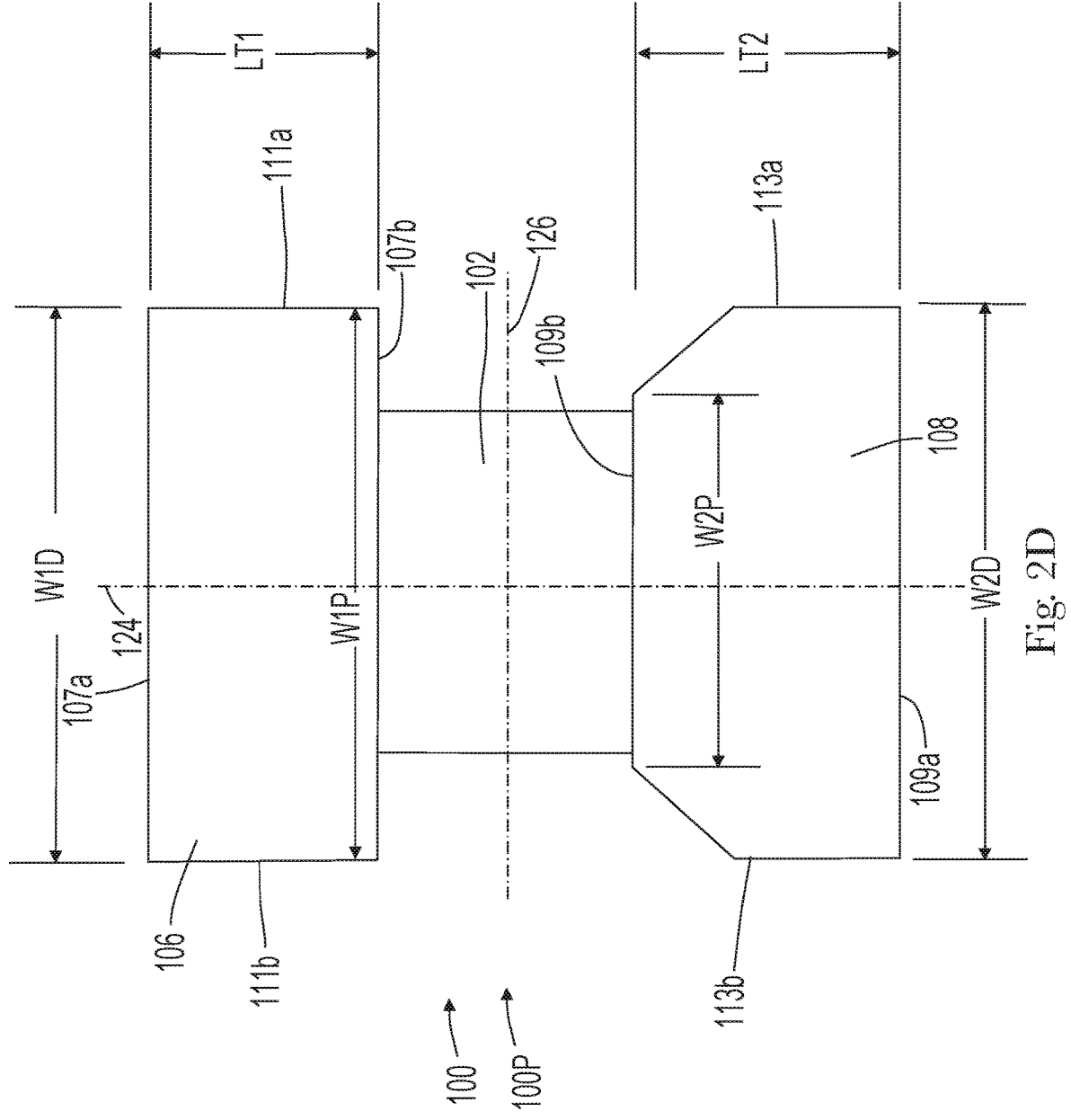
FIG. 2D shows a plan view of a diaper pant with the portion of the diaper that faces away from a wearer oriented toward the viewer, illustrating first and second belt size and shape features.

In some configurations, at least one of the first elastic belt 106 and the second elastic belt 108 may comprise lateral edges having different lengths. For example, FIG. 2D shows a configuration wherein the first elastic belt 106 defines a generally rectangular shape, such as described with reference to FIG. 2C, and wherein the outer laterally extending edge 109*a* of the second elastic belt 108 and the inner laterally extending edge 109*b* have different lengths. As shown in FIG. 2D, the outer laterally extending edge 109*a* of the second elastic belt 108 may comprise a lateral width of W2D and the inner laterally extending edge 109*b* may comprise a lateral width of W2P, wherein W2D is greater than W2P.

Figure 2E:
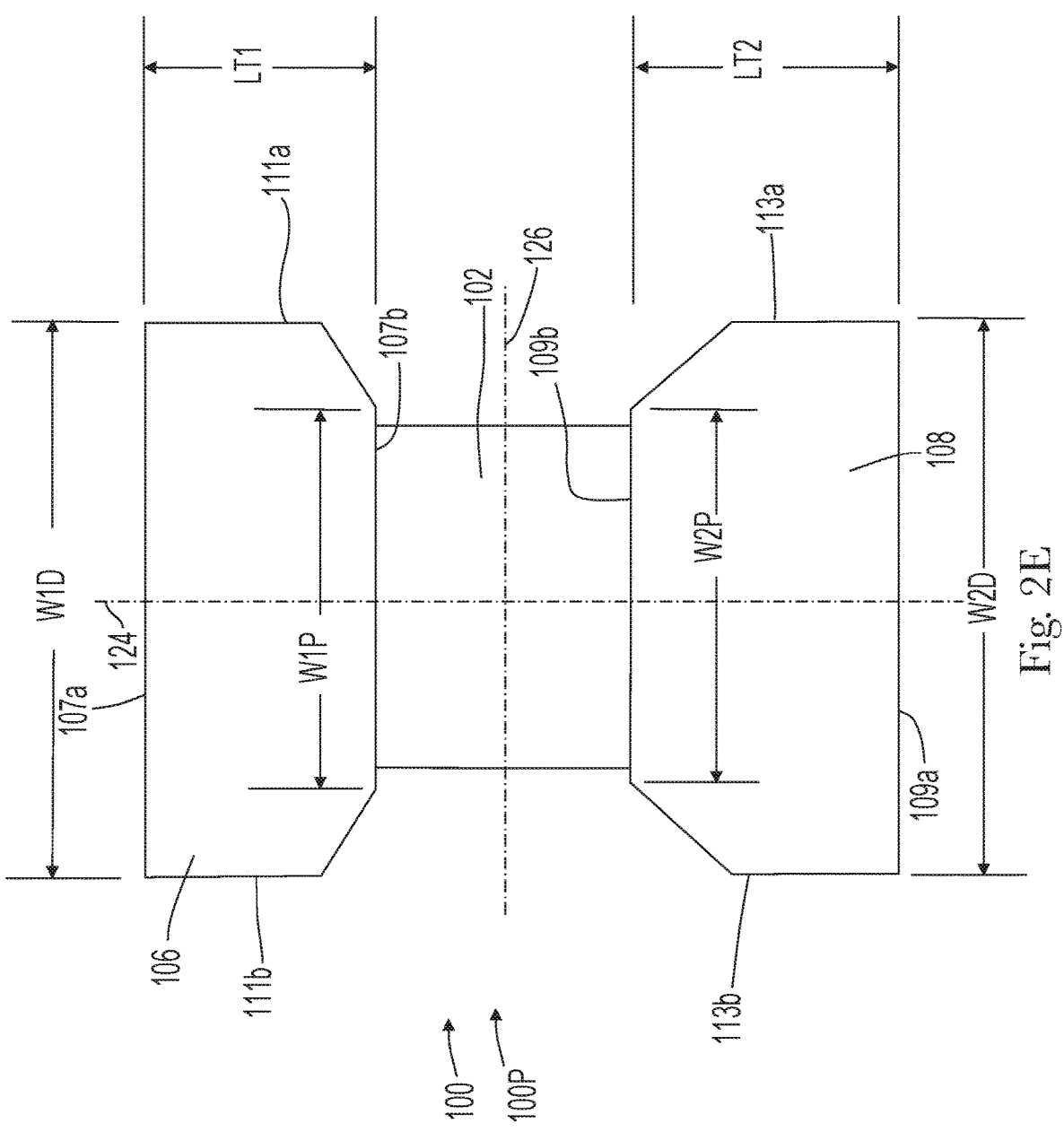
FIG. 2E shows a plan view of a diaper pant with the portion of the diaper that faces away from a wearer oriented toward the viewer, illustrating first and second belt size and shape features.

In some configurations, both the first elastic belt 106 and the second elastic belt 108 may comprise lateral edges having different lengths. For example, FIG. 2E shows a configuration wherein the outer laterally extending edge 107*a* of the first elastic belt 106 and the inner laterally extending edge 107*b* have different lengths, and wherein the outer laterally extending edge 109*a* of the second elastic belt 108 and the inner laterally extending edge 109*b* have different lengths. As shown in FIG. 2E, the outer laterally extending edge 107*a* of the first elastic belt 107 may comprise a lateral width of W1D and the inner laterally extending edge 107*b* may comprise a lateral width of W1P, wherein W1D is greater than W1P, and wherein the outer laterally extending edge 109*a* of the second elastic belt 108 may comprise a lateral width of W2D and the inner laterally extending edge 109*b* may comprise a lateral width of W2P, wherein W2D is greater than W2P.

With reference to FIGS. 2C-2E, the first elastic belt 106 may define a longitudinal length LT1 extending between outer laterally extending edge 107*a* and the inner laterally extending edge 107*b*, and the second elastic belt 108 may define a longitudinal length LT2 extending between outer laterally extending edge 109*a* and the inner laterally extending edge 109*b*. In some configurations, LT1 may be equal to LT2. In some configurations, LT1 may be less or greater than LT2. With continued reference to FIGS. 2C-2E, in some configurations, W1D may be equal to W1P, or W1D may be different than W1P. In some configurations, W2D may be equal to W2P, or W2D may be different than W2P. In some configurations, W1D and/or W1P may be equal to or different W2D and/or W2P.

Figure 3:
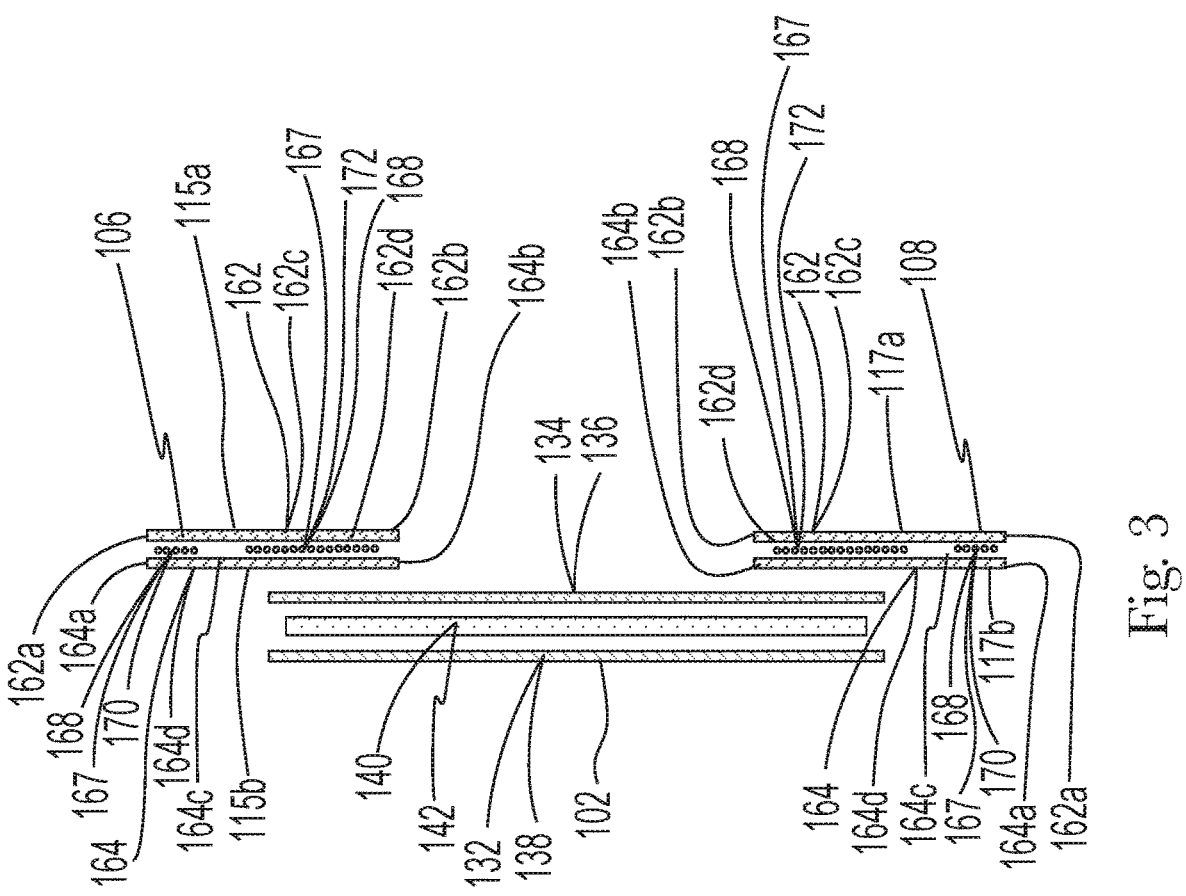
FIG. 3 is a cross-sectional view of the diaper pant of FIG. 2A taken along line 3-3 showing first and second elastic belts provided with panel layers.

With reference to FIGS. 2A, 2B, and 3, the first elastic belt 106 and the second elastic belt 108 may also each include a first substrate 162 and a second substrate 164. The first substrates 162 may be oriented to define at least a portion of a garment facing surface 115*a* of the first elastic belt 106 and a garment facing surface 117*a* the second elastic belt 108, and the second substrates 164 may be oriented to define at least a portion of a wearer facing surface 115*b* of the first elastic belt 106 and a wearer facing surface 117*b* of the second elastic belt 108. The first substrate 162 may extend from a proximal edge 162*b* to a distal edge 162*a* for a maximum length L1, and the second substrate 164 may extend from a proximal edge 164*b* to a distal edge 164*a* for a maximum length L2. It is to be appreciated that the distal edge 162*a* and/or the proximal edge 162*b* of the first substrate 162 may be straight and/or curved and/or may be parallel or unparallel to each other. It is also to be appreciated that the distal edge 164*a* and/or the proximal edge 164*b* of the second substrate 164 may be straight and/or curved and/or may be parallel or unparallel to each other. As such, the maximum length L1 refers to the longest distance extending longitudinally between the distal edge 162*a* and the proximal edge 162*b* of the first substrate 162, and the maximum length L2 refers to the longest distance extending longitudinally between the distal edge 164*a* and the proximal edge 164*b* of the second substrate 164. In some configurations, L1 may be equal to, less than, or greater than L2. In some configurations, L1 may be equal to or less than LT1, and L2 may be equal to or less than LT2. In some configurations, the distal edge 162*a* of the first substrate 162 may define at least a portion of the front waist edge 121 and/or at least a portion of back waist edge 122, and/or the distal edge 164*a* of the second substrate 164 may define at least a portion of the front waist edge 121 and/or at least a portion of back waist edge 122. As such, in some configurations, the distal edge 162*a* of the first substrate 162 and/or the distal edge 164*a* of the second substrate 164 may define at least a portion of the waist opening 110.

Figure 1A:
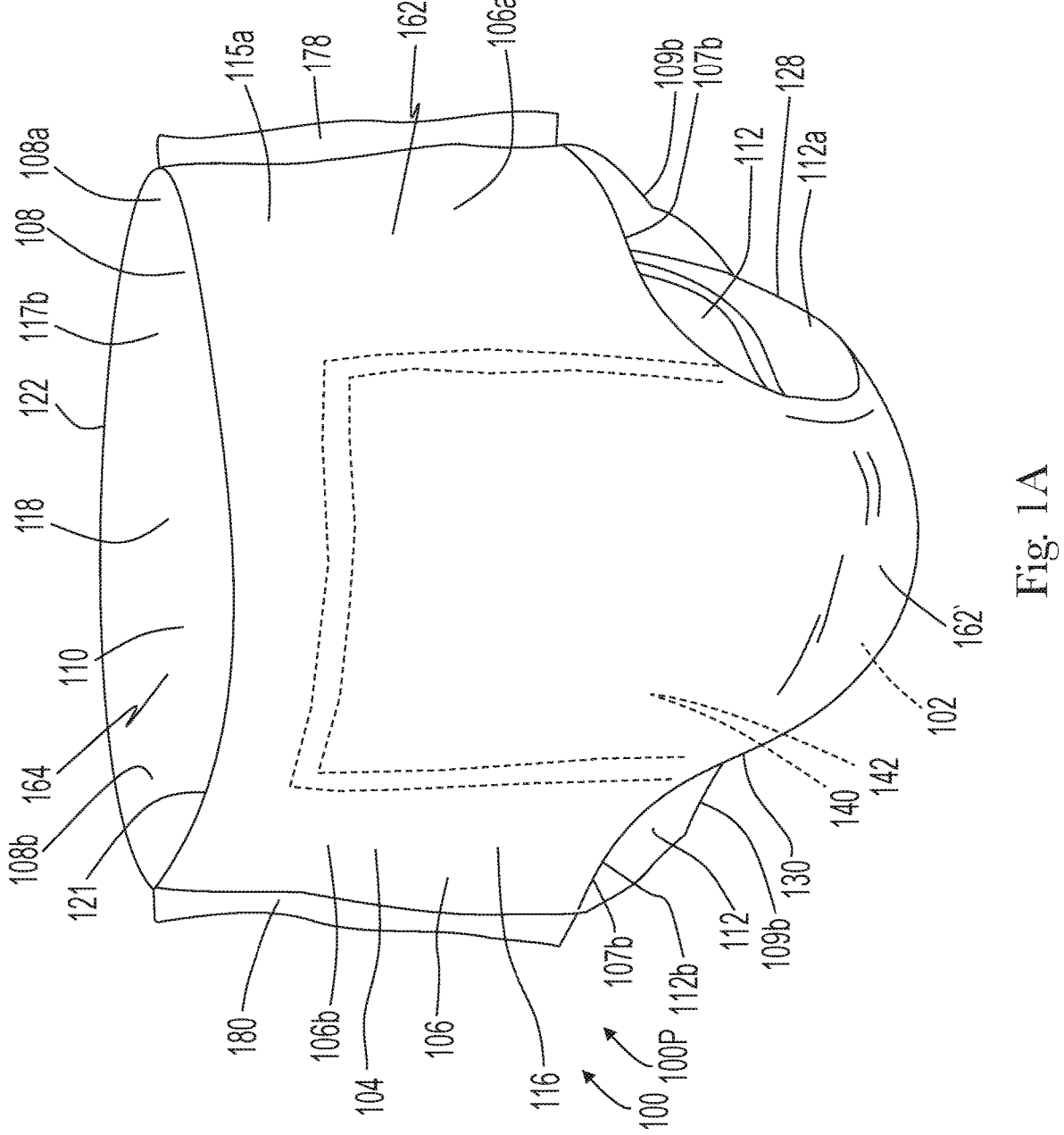
FIG. 1A shows a perspective view of a diaper pant with a continuous outer cover in a pre-fastened configuration.
Figure 2F:
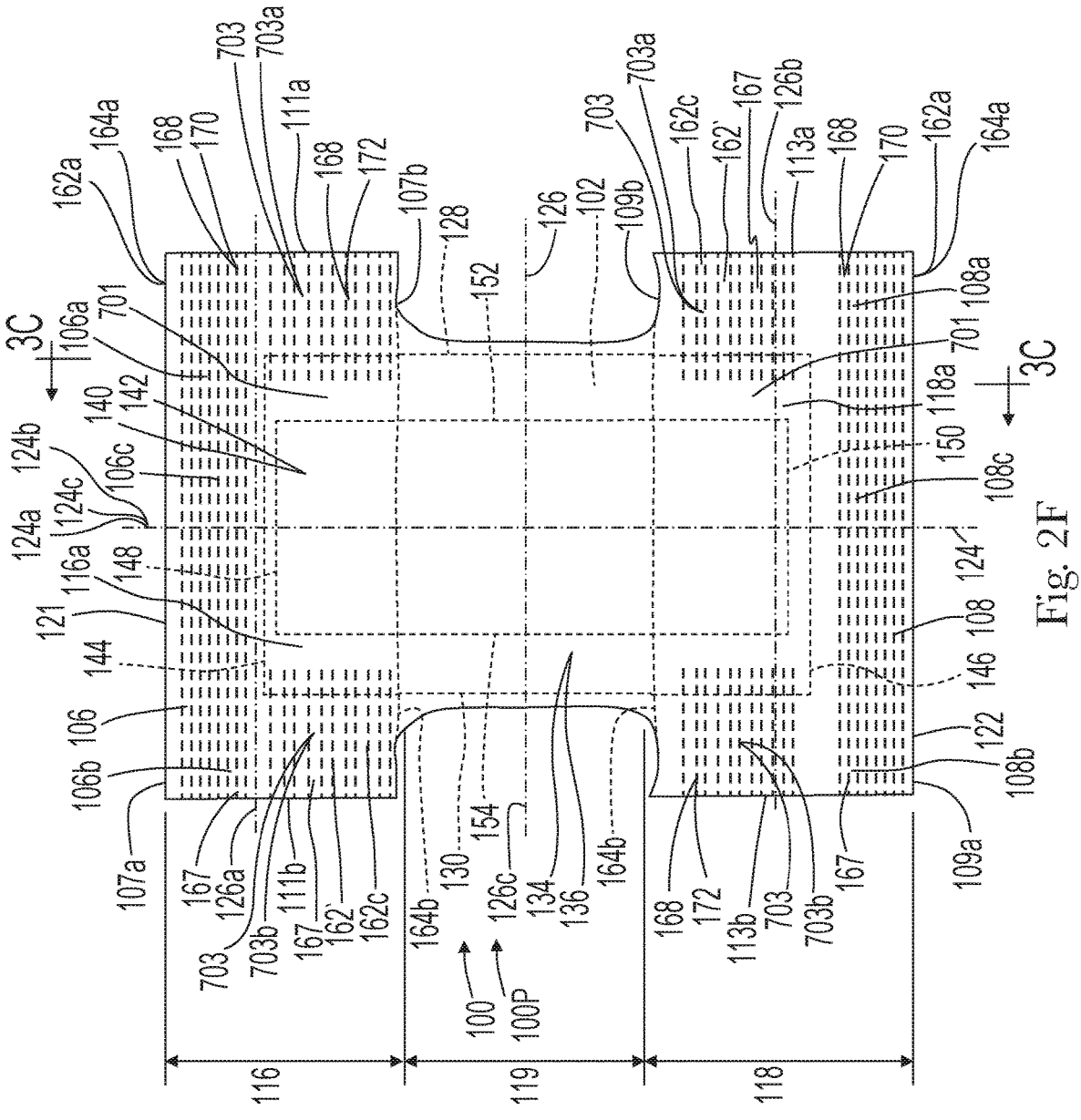
FIG. 2F shows a plan view of a diaper pant with a continuous outer cover with the portion of the diaper that faces away from a wearer oriented toward the viewer.

It is also to be appreciated that the first substrate 162 and/or the second substrate 164 may extend continuously from the first belt 106 to the second belt 108. For example, the first substrate 162 may be configured to define a continuous outer cover 162' that extends contiguously from the first waist edge 121 to the second waist edge 122, such as shown in FIGS. 1A, 2F, and 3C. It is also to be appreciated that diaper pants 100P with continuous outer covers, such as shown in FIGS. 1A, 2F, and 3C may also be configured to include various aspects of the frangible pathways and fastener components discussed herein.

It is to be appreciated that the first substrate 162 and the second substrate 164 may define various lateral widths that may or may not be equal. For example, as shown in FIG. 2B, the first substrate 162 may extend laterally between a first longitudinal edge 162*e* and a second longitudinal edge 162*f* to define a first lateral width W1, and the second substrate 164 may extend laterally between a first longitudinal edge 164*e* and a second longitudinal edge 164*f* to define a second lateral width W2.

In some configurations, the proximal edge 162*b* of the first substrate 162 and/or the proximal edge 164*b* of the second substrate 164 may extend laterally across the backsheet 136. As shown in FIGS. 2A-3, the first substrate 162 includes a garment facing surface 162*c* and an opposing wearer facing surface 162*d*, and the second substrate 164 includes a garment facing surface 164*c* and an opposing wearer facing surface 164*d*.

In some configurations, the first elastic belt 106 and/or the second elastic belt 108 may include a folded portion of at least the first substrate 162 and/or the second substrate 164.

Figure 3A:
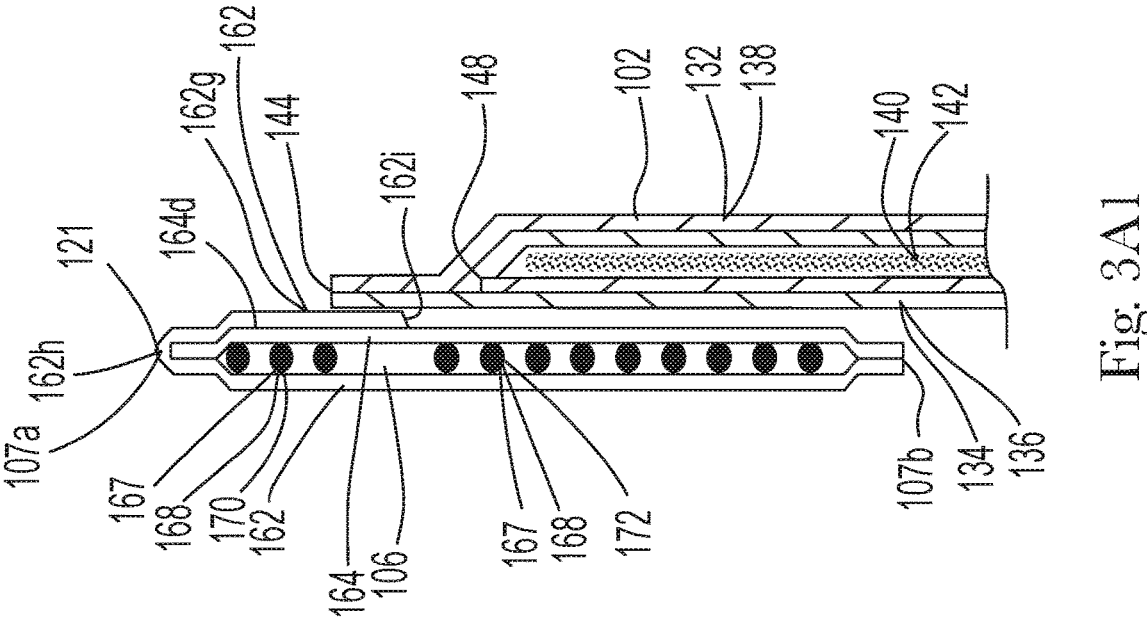
FIG. 3A is a cross-sectional detailed view of a first belt provided with panel layers wherein one panel layer is folded over another panel layer.
Figure 3A:
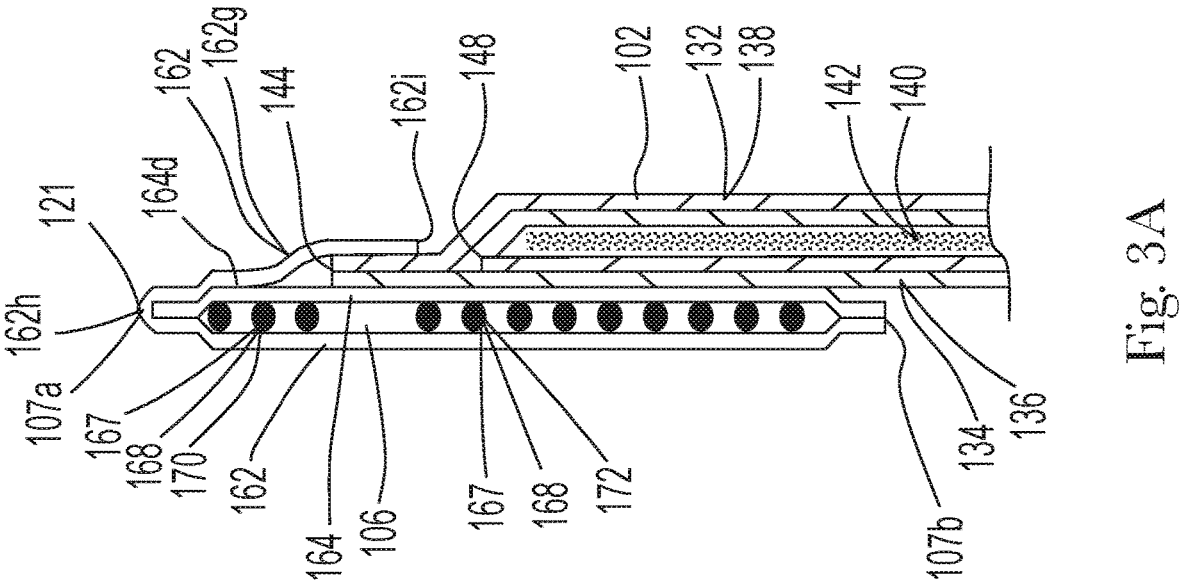
Figure 3C:
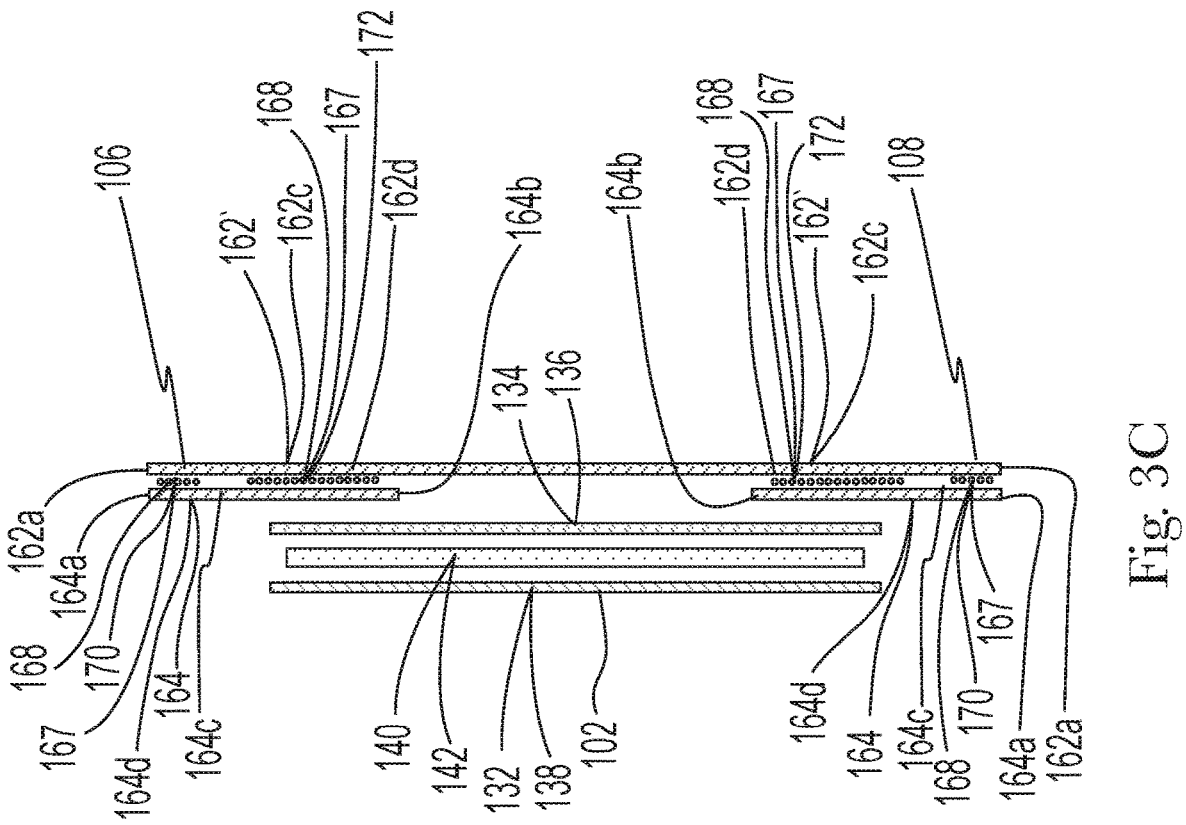
FIG. 3C is a cross-sectional view of the diaper pant of FIG. 2F taken along line 3C-3C showing first and second elastic belts provided with panel layers and a continuous outer cover.

For example, as shown in FIGS. 3A and 3B, the first elastic belt 106 and/or the second elastic belt 108 may include a folded portion 162g of the first substrate 162 extending longitudinally between a fold line 162h in the first substrate 162 and a lateral edge 162i. As such, the folded portion 162g of the first substrate 162 may be connected with the wearer facing surface 164d of the second substrate 164. In some configurations, the folded portion 162g of the first substrate 162 may also be connected with and/or overlap the chassis 102. In some configurations, the folded portion 162g of the first substrate 162 may also be connected with the wearer facing surface 162d of the first substrate 162. In some configurations, a portion of the folded portion 162g of the first substrate 162 may be left unbonded to the chassis 102 and/or the second substrate 164, forming a pocket having an opening oriented toward the lateral centerline 162c of the chassis 102. In another example, the first elastic belt 106 and/or the second elastic belt 108 may include a folded portion of the second substrate 164 extending longitudinally between a fold line in the second substrate 164 and a lateral edge. As such, the folded portion of the second substrate 164 may be connected with the garment facing surface 162c of the first substrate 162. As such, in some configurations, a fold line of the first substrate 162 and/or a fold line of the second substrate 164 may define at least a portion of the waist opening 110. It is to be appreciated that various waist configurations may be utilized. For example, as shown in FIG. 3A1, the folded portion 162g may be sandwiched between the second substrate 164 and the backsheet 136. In another example shown in FIG. 3A2, the second substrate 164 may be sandwiched between the folded portion 162g and the backsheet 136. Although FIGS. 3A1 and 3A2 show configurations of the first belt 106, it is to be appreciated that such configurations may be applied with the second belt 108.

It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that components of the first elastic belt 106 and the second elastic belt 108, such as the first substrate 162, and/or second substrate 164 may be constructed from various materials. For example, the first and/or second belts may include a first substrate 162, and/or second substrate 164 that may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some configurations, the first and/or second belts may include a first substrate 162, and/or second substrate 164 comprising a nonwoven web of synthetic fibers, and may include a stretchable nonwoven. In some configurations, the first and second elastic belts may include an inner hydrophobic, non-stretchable nonwoven material and an outer hydrophobic, non-stretchable nonwoven material. It is to be appreciated that the belts may configured in various ways, such as disclosed for example, in U.S. Patent Publication No. 2022/0142828 A1 and Chinese Patent Application No. CN2021/077843, which are both incorporated by reference.

Elastic material 167 may be positioned between the wearer facing surface 162d of the first substrate 162 and the garment facing surface 164c of the second substrate 164. It is to be appreciated that the elastic material 167 may include one or more elastic elements such as strands, ribbons, elastic films, or panels extending along the lengths of the elastic belts. As shown in FIGS. 2A and 3, the elastic material 167 may include a plurality of elastic strands 168. In some configurations, the elastic material 167 may be an elastic film used to form a zero-strain elastic laminate comprising an elastic film bonded to one or more nonwoven layers and subsequently subjected to mechanical deformation or activation sufficient to weaken the nonwoven layer(s) and enable the laminate to stretch and recover elastically.

It is also to be appreciated that the first substrate 162, second substrate 164, and/or elastic material 167 of the first elastic belt 106 and/or second elastic belt 108 may be bonded together and/or with other components, such as the chassis 102, with adhesive and/or mechanical bonds. It is to be appreciated that adhesive and mechanical bonding methods may be utilized alone or in combination with each other.

In some configurations, adhesive may be applied to at least one of the first substrate 162, second substrate 164, and/or elastic material 167 when being combined to form the first elastic belt 106 and/or second elastic belt 108. In some configurations, mechanical bonding devices may apply mechanical bonds to the to at least one of the first substrate 162, second substrate 164, and/or elastic material 167 when being combined to form the first elastic belt 106 and/or second elastic belt 108. Such mechanical bonds may be applied with heat, pressure, and/or ultrasonic devices. In some configurations, mechanical bonding devices may apply bonds that bond the first substrate 162, second substrate 164, and/or elastic material 167 together and/or may act to trap or immobilize discrete lengths of the contracted elastic strands in the first elastic belt 106 and/or second elastic belt 108.

It is also to be appreciated that the first substrate 162, second substrate 164, and/or elastic material 167 may be bonded together with various methods and apparatuses to create various elastomeric laminates, such as described in U.S. Patent Publication Nos. 2018/0168878 A1; 2018/0168877 A1; 2018/0168880 A1; 20180/170027 A1; 2018/0169964 A1; 2018/0168879 A1; 2018/0170026 A1; 2018/0168889 A1; 2018/0168874 A1; 2018/0168875 A1; 2018/0168890 A1; 2018/0168887 A1; 2018/0168892 A1; 2018/0168876 A1; 2018/0168891 A1; 2019/0070042 A1; 2019/0070041 A1; 2021/0282797 A1; and 2021/0275362 A1, and combinations thereof, all of which are incorporated herein by reference.

It is to be appreciated that components of the first elastic belt 106 and/or the second elastic belt 108 may be assembled in various ways and various combinations to create various desirable features that may differ along the lateral width and/or longitudinal length of the first elastic belt 106 and/or the second elastic belt 108. Such features may include, for example, Dtex values, bond patterns, aperture arrangements, elastic positioning, Average Dtex values, Average Pre-Strain values, rugosity frequencies, rugosity wavelengths, height values, and/or contact area. It is to be appreciated that differing features may be imparted to various components, such as for example, the first substrate 162, second substrate 164, and elastic material 167 before and/or during stages of assembly of the first elastic belt 106 and/or the second elastic belt 108.

It is to be appreciated that the first elastic belt 106 and/or the second elastic belt 108 may include various configurations of belt elastic materials 167 arranged in relation to each other and to the first substrate 162, and the second substrate 164. As discussed above, the elastic material 167 may include configurations of one or more elastic elements such as strands, ribbons, films, or panels positioned in various arrangements. In some configurations, the elastic material 167 may comprise various elastics, elastic features and arrangements, and processes for assembly, such as described in 2018/0168889 A1; 2018/0168874 A1; 2018/0168875 A1; 2018/0168890 A1; 2018/0168887 A1; 2018/0168892 A1; 2018/0168876 A1; 2018/0168891 A1; 2019/0298586 A1; 2019/0070042 A1; 2018/0168878 A1; 2018/0168877 A1; 2018/0168880 A1; 2018/0170027 A1; 2018/0169964 A1; 2018/0168879 A1; 2018/0170026 A1; 2019/0070041 A1; 2021/0282797 A1; and 2021/0275362 A1, which are all incorporated by reference. It is also to be appreciated the elastic materials 167 herein may be configured with identical or different colors in various different locations on the first elastic belt 106 and/or the second elastic belt 108.

In some configurations, the elastic material 167 may be configured as elastic strands 168 disposed at a constant interval in the longitudinal direction. In other embodiments, the elastic strands 168 may be disposed at different intervals in the longitudinal direction. In some configurations, the Dtex values of the elastic strands 168 may be constant or varied along the longitudinal direction. In some configurations, the elastic material 167 in a stretched condition may be interposed and joined between uncontracted substrate layers. When the elastic material 167 is relaxed, the elastic material 167 returns to an unstretched condition and contracts the substrate layers. The elastic material 167 may provide a desired variation of contraction force in the area of the ring-like elastic belt. It is to be appreciated that the chassis 102 and elastic belts 106, 108 may be configured in different ways other than as depicted in attached Figures. It is also to be appreciated that the elastic material 167 material may be joined to the substrates continuously or intermittently along the interface between the elastic material 167 material and the substrates. In some configurations, the elastic strands 168 may be in the form of extruded elastic strands, which may also be bonded with the first substrate 162 and/or second substrate 164 in a pre-corrugated configuration, such as disclosed for example in U.S. Pat. No. 5,681,302, which is incorporated by reference herein.

As discussed above for example with reference to FIGS. 2A and 3, the elastic material 167 discussed herein may be in the form of elastic strands 168. In some configurations, the elastic strands 168 may be parallel with each other and/or with the lateral axis 126. It is to be appreciated that the first elastic belt 106 and/or second elastic belt 108 may be configured to include various quantities of elastic strands 168. In some configurations, elastic strands 168 may be grouped in pairs. In some configurations, the first elastic belt 106 and/or second elastic belt 108 may comprise from about 10 to about 1500 elastic strands 168. It is also to be appreciated that elastic strands 168 herein may comprise various Dtex values, strand spacing values, and pre-strain values and such elastic strands 168 may utilized with other elastic strands to create first and second elastic belts 106, 108 comprising elastic strands 168 in various combinations of Dtex values, strand spacing values, and pre-strain values. For example, in some configurations, the Average-Dtex of one or more elastic strands 168 may be greater than 500. In some configurations, the Average-Dtex of one or more elastic strands 168 may be from about 10 to about 1500, specifically reciting all 1 Dtex increments within the above-recited range and all ranges formed therein or thereby. In some configurations, a plurality of elastic strands 168 may comprise an Average-Strand-Spacing of less than or equal to 4 mm. In some configurations, a plurality of elastic strands 168 may comprise an Average-Strand-Spacing from about 0.25 mm to about 4 mm, specifically reciting all 0.01 mm increments within the above-recited range and all ranges formed therein or thereby. In some configurations, a plurality of elastic strands 168 may comprise an Average-Strand-Spacing of greater than 4 mm. In some configurations, the Average-Pre-Strain of each of a plurality of elastic strands may be from about 50% to about 400%, specifically reciting all 1% increments within the above-recited range and all ranges formed therein or thereby. In some configurations, the elastic strands 168 comprise an Average-Strand-Spacing from about 0.25 mm to about 4 mm and an Average-Dtex from about 10 to about 500. In some configurations, the elastic strands 168 may comprise an Average-Pre-Strain from about 75% to about 300%.

In some configurations, a first plurality of elastic strands may comprise a first Average-Pre-Strain from about 75% to about 300%, and a second plurality of elastic strands may comprise a second Average-Pre-Strain that is greater than first Average-Pre-Strain. In some configurations, a first plurality of elastic strands comprises an Average-Strand-Spacing from about 0.25 mm to about 4 mm and an Average-Dtex from about 10 to about 500; and a second plurality of elastic strands may comprise an Average-Strand-Spacing greater than about 4 mm and an Average-Dtex greater than about 450.

In some configurations, such as shown in FIG. 2A, the elastic strands 168 may be referred to herein as outer waist elastics 170 and inner waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. Some elastic strands 168, such as the inner waist elastics 172, may be configured with discontinuities in areas, such as for example, where the first and second elastic belts 106, 108 overlap portions of the chassis 102, such as the absorbent assembly 140.

As shown in FIG. 2A, the first elastic belt 106 and/or second elastic belt 108 may be configured with low-stretch zones 701 and high-stretch zones 703. The first elastic belt 106 and/or the second elastic belt 108 may include a first high-stretch zone 703a and a second high-stretch zone 703b separated laterally by a low-stretch zone 701. Portions of the chassis 102, such as the backsheet 136 and absorbent assembly 140, may be connected with the first elastic belt 106 and/or the second elastic belt 108 in the low-stretch zones 701 in the first waist region 116 and/or the second waist region 118. The high-stretch zones 703 are elasticated by the elastic material 167, such as the elastic strands 168, 172; and the low-stretch zones 701 may comprise cut lines separating the elastic material 167, such as the elastic strands 168, 172. In some configurations, the elastic material 167 may be cut in an unbonded region where the elastic material is not bonded with first substrate 162 and the second substrate 164. Thus, the elastic material 167 retracts from the unbonded region and form low-stretch zone 701. In some configurations, the elastic material 167 may be cut into several discrete pieces. In turn, the low-stretch zones 701 define regions of the first elastic belt 106 and/or the second elastic belt 108 that have relatively less elasticity than the high-stretch zones 703. The discrete elastic material 167 that has been cut and which are elastically contracted do not add any substantial amount of elastication to the low-stretch zone 701. As such, upon application of a force, the high-stretch zones 703 will elongate more than the low-stretch zones 701. As provided above, the terms "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force. In some configurations, the first elastic belt 106 and/or the second elastic belt 108 may be configured with high-stretch zones 703 that are elastic and may be configured with low-stretch zones 701 that are not elastic or "inelastic."

Figures 4A, 4B:
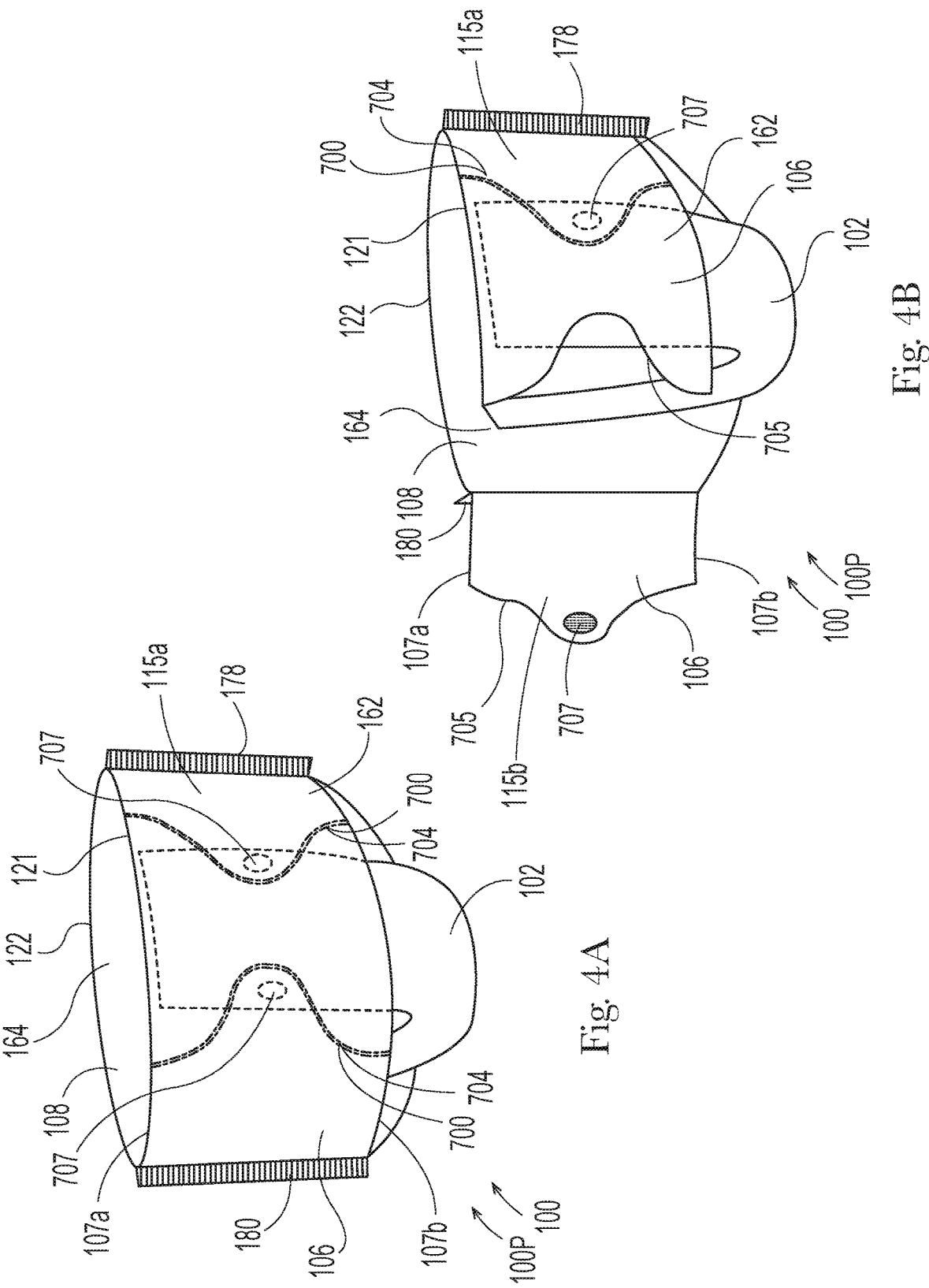
FIG. 4A is perspective view of a diaper pant including frangible pathways in a front belt and adjacent an absorbent chassis.
FIG. 4B is a perspective view of the diaper pant of FIG. 4A showing the front belt having been torn along one of the frangible pathways.
Figure 4C:
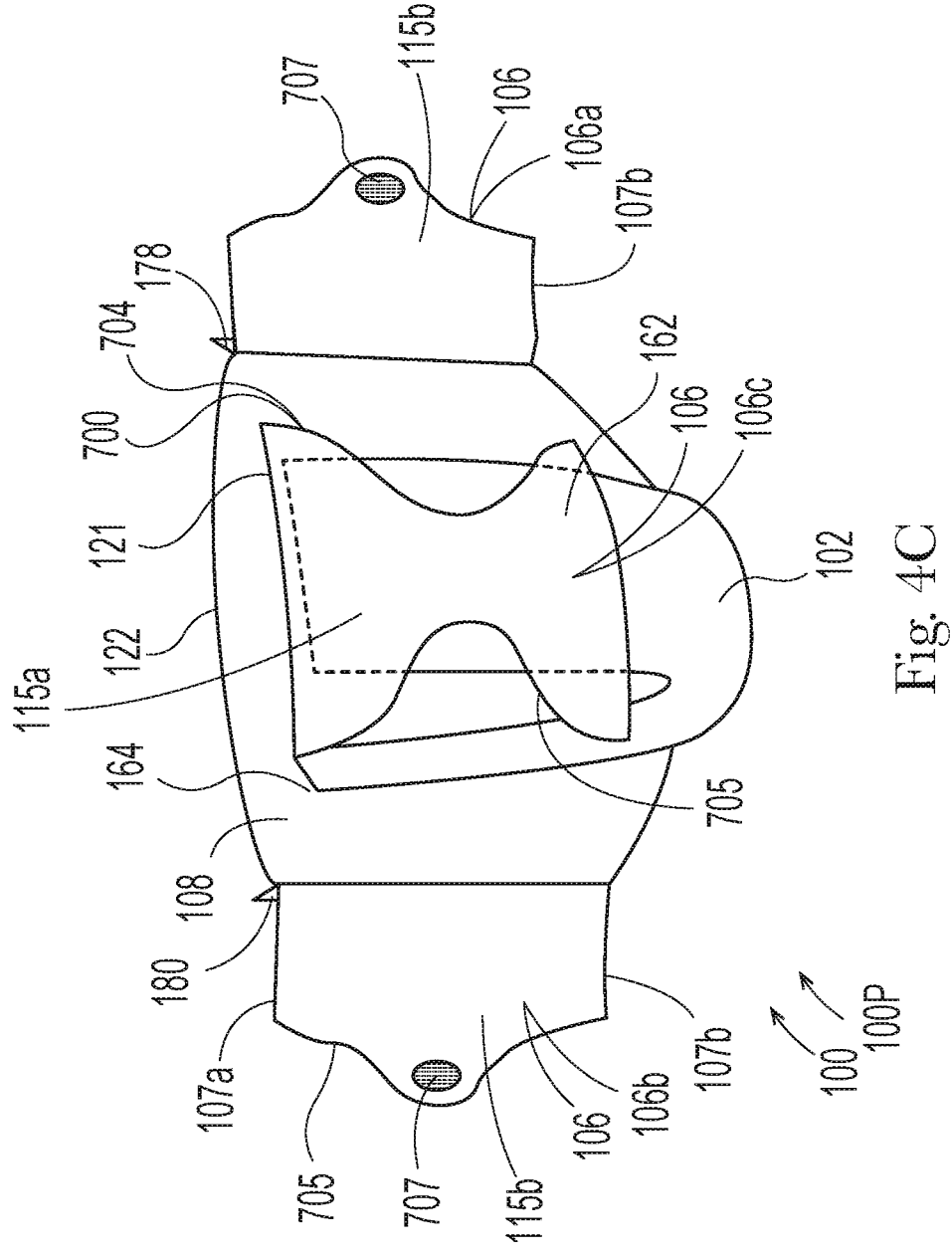
FIG. 4C is a perspective view of the diaper pant of FIG. 4A showing the front belt having been torn along two frangible pathways.

As discussed above, the diaper pants 100P described with reference to FIGS. 1-3C may include one or more frangible pathways in the first belt 106 and/or the second belt 108. For example, FIGS. 4A-4C show an example diaper pant 100P with a first belt 106 that includes frangible pathways 700. The frangible pathways 700 may be configured to allow the first elastic belt 106 to be relatively easily torn along the frangible pathway 700, such as when removing the diaper pant 100P from a wearer. FIG. 4B shows a view of the diaper pant 100P from FIG. 4A, illustrating the first belt 106 after having been torn along the frangible pathway 700 through both the outer longitudinal outer laterally extending edge 107a and the inner laterally extending edge 107b of the first belt 106. As such, the first elastic belt 106 shown in FIG. 4B is separated by opposing tear lines 705. It is to be appreciated the first elastic belt 106 may be torn along both frangible pathways 700 in FIG. 4B. For example, FIG. 4C shows the diaper pant of FIG. 4A showing the front belt having been torn along two frangible pathways 700. As shown in FIG. 4C, the central region 106c of the first elastic belt 106 may remain bonded with the chassis 102 after separating the first and second opposing end regions 106a, 106b from the central region 106c by tearing the elastic belt 106 along the frangible pathways 700.

As discussed in more detail below, the frangible pathways 700 comprise a plurality of lines of weakness 704 configured such that all elastic strands 168 in the first elastic belt 106 are severed at least once in the frangible pathway 700. Severing the elastic strands 168 in the frangible pathway 700 helps make it relatively easier to tear the first elastic belt 106 along the frangible pathway 700. For example, when the elastic strands 168 are severed, the first substrate 162 and second substrate 164 of the first elastic belt 106 need only need to be torn without having to also tear uncut elastic strands 168. It is to be appreciated that the diaper pant 100P may include various quantities of frangible pathways 700 that may be: positioned in various locations; define various shapes; and extend for various lengths. For example, the first elastic belt 106 may comprise a first belt length defined by a longitudinal distance between the proximal edge 107b and the distal edge 107a, and the frangible pathway 700 may extend for a total length from an outermost edge of a line of weakness 704 nearest the proximal edge 107b of the first belt 106 to an outermost edge of a line of weakness 704 nearest the distal edge 107a of the first belt 106. In some configurations, the frangible pathway 700 may extend for a total length that is greater than, equal to, or less than the first belt length. In some configurations, the lines of weakness 704 may extend for a length from a first end to a second end, and a sum of the all the lengths of lines of weakness 704 in the frangible pathway 700 may be greater than the frangible pathway total length.

In some configurations, diaper pants 100P may be configured such that one or both of the first elastic belt 106 and the second elastic belt 108 include one or more frangible pathways 700. The frangible pathways 700 may be positioned in various locations on the first and second elastic belts 106, 108. For example, such as shown in FIGS. 4A-4C, frangible pathways 700 may extend to overlap with the chassis 102. In some configurations, the frangible pathways 700 may extend in straight lines and/or may be curved and/or have curved portions. In some configurations, the frangible pathways 700 may extend longitudinally for the entire length or less than the entire length of the first belt 106 and/or second belt 108. In some configurations, frangible pathways 700 may be positioned partially or entirely laterally between the first and second side seams 178, 180 and the chassis 102.

Figures 5A, 5B:
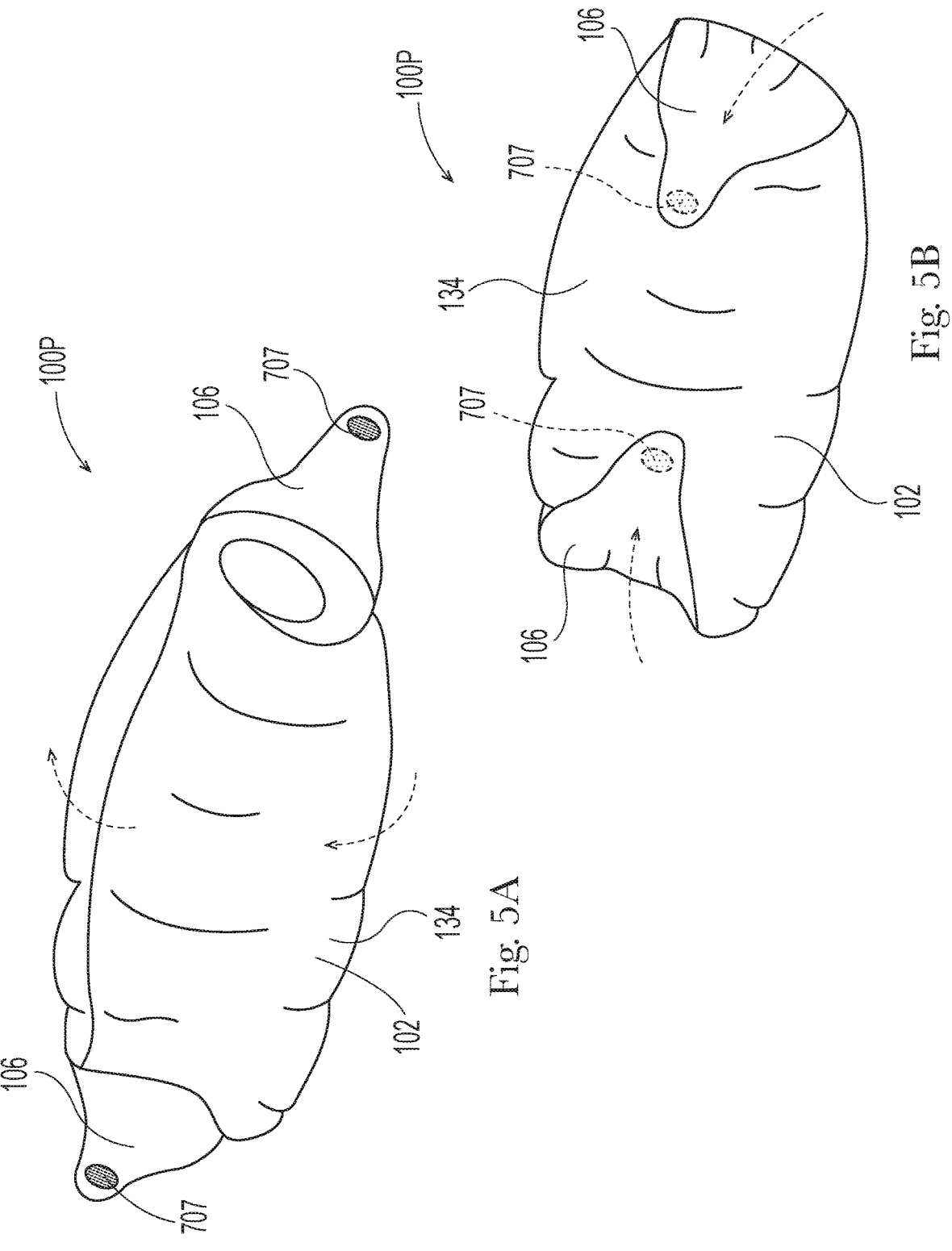
FIG. 5A shows the diaper pant of FIG. 4C being rolled up onto itself in a longitudinal direction.
FIG. 5B shows the diaper pant of FIG. 5A with fastener components connected with the backsheet of the chassis to maintain the diaper pant in a disposal configuration.

In some configurations, the frangible pathways 700 may be configured and/or positioned to provide access to and/or function with other features, such as disposal features. For example, the diaper pant 100P shown in FIGS. 4A-4C includes fastener components 707 positioned on the wearing facing surface 115b of the first elastic belt 106. In some configurations, the fastener components 707 may be positioned between the first elastic belt 106 and the chassis 102. The fastener component 707 may be configured to refastenably connect with other portions of the diaper pant 100P, such as for example, the garment facing surfaces of the first elastic belt 106, the second elastic belt 108, or the chassis 102. As such, once the first elastic belt 106 is torn along the frangible pathways 700, the diaper pant 100P may be removed from a wearer and rolled or folded up for disposal, and the fastener component 707 may be connected with another portion of the diaper pant 100P to help maintain the diaper pant 100P in a disposal configuration. For example, FIG. 4C shows a diaper pant 100P after tearing the first elastic belt 106 along two frangible pathways. FIG. 5A shows the diaper pant 100P of FIG. 4C with the chassis 102 being rolled up onto itself in a longitudinal direction. And FIG. 5B shows the diaper pant 100P of FIG. 5A with fastener components 707 refastenably connected with the backsheet 136 of the chassis 102 to maintain the diaper pant 100P in a disposal configuration. In some configurations, when tearing the elastic belt along the frangible pathway 700, the tearing process may begin by tearing from the outer edge 107a or the inner edge 107b of the elastic belt 106. As discussed in more detail below, in some configurations, the first elastic belt 106 may also include an opening, such as a slit located adjacent to or in the proximity of the fastener component 707 and the weakened region 700 to help facilitate starting to tear the frangible pathway 700 in a region of the elastic belt 106 longitudinally between the outer edge 107a and the inner edge 107b.

It is also to be appreciated that the fastener component 707 may be configured in various ways, such as hooks, loops, and/or adhesive. For example, the fastener component 707 may comprise hook elements or adhesive adapted to refastenably connect with another surface of the diaper pant 100P. In some configurations, the fastener component 707 may comprise loop elements adapted to refastenably connect with hook surface on the diaper pant 100P. The fastener component 707 may be a separate element connected with the elastic belt 106 in various ways, such as mechanical bonding, adhesive bonding, or both. In some configurations, the fastener component 707 may be integrally formed from materials of the elastic belt 106, 108. In some configurations, the fastener component 707 may be printed and/or comprise materials of various different colors such that the fastener component 707 may be visible from outside the diaper pant 100P.

As previously mentioned, the fastener component 707 may comprise a hook material that can refastenably engage with substrates, such as nonwovens for example, on an exterior surface of the diaper pant 100P. For example, the fastener component 707 may comprise a substrate comprising hooks, with the substrate bonded to the elastic belt 106, 108, such as the second substrate 164, which may be in the form of a nonwoven. It is to be appreciated that the substrate may be bonded to the elastic belt 106, 108 in various ways, such as for example, with mechanical bonds, thermal bonds, ultrasonic bonds, and/or adhesive bonds or combinations thereof. In some configurations, hooks may be integrally formed from the second substrate 164, which may be in the form of a nonwoven. The fastener component 707 may comprise one material or a combination of two or more materials arranged in at least partially overlapping configuration. In some configurations, the fastener component 707 may comprise other fastener types as known in the art.

It is to be appreciated that the fastener component 707 may comprise any of a wide variety of shapes, including rectangles or other polygons, circles, ovals, shapes having exterior convexities or concavities or combinations thereof, or one or a plurality of lines or geometric shapes forming an array. It is to be appreciated that the fastener component 707 may comprise various sizes. For example, in some configurations, the fastener component 707 may have a lateral width of between about 5 mm and about 100 mm, specifically reciting all 0.1 mm increments within the above-recited range and all ranges formed therein or thereby. In some configurations, the fastener component 707 may have a longitudinal length of between about 10 mm and about 100 mm, specifically reciting all 0.1 mm increments within the above-recited range and all ranges formed therein or thereby. The fastener component 707 may be aligned parallel the lateral centerline 126*a*, 126*b* of the elastic belt 106, 108 or may be oriented at an angle relative the longitudinal centerline 126*a*, 126 of the elastic belt 106, 108 of between 0 and 90 degrees. The fastener component 707 may comprise an array of two or more spaced-apart fastening elements. The fastener component 707 may have a color that is visible through any layers of the elastic belt 106, 108 on which the fastener component 707 is located. The elastic belt 106, 108 and/or chassis 102 may include printing or other indicia highlighting to a caregiver the location, function, and/or usage of the fastener component 707. The bond, or bond pattern, attaching the fastener component 707 to the elastic belt 106, 108 may be visually or tactilely distinct from the surrounding belt material in order to provide the caregiver a signal or a mechanical grip advantage.

It is also to be appreciated that the frangible pathways 700 may comprise lines of weakness 704 that are: configured in various ways; positioned in various locations and orientations relative to each other; defined by various shapes; and extend for various lengths. For example, in some configurations, the lines of weakness 704 comprise discrete cut lines that penetrate through some or all the layers of the elastic belt 106. In some configurations, the lines of weakness 704 comprise discrete bonds wherein materials of the first substrate and the second substrate are fused together. In some configurations, the lines of weakness 704 may be linear, curvilinear, or have a regular or irregular geometry and may comprise one or more of a perforation, a bond, an aperture, or a mechanically thinned region of a material such as a nonwoven, or a combination thereof. It is also to be appreciated that the lines of weakness 704 can be formed with different lengths and spacings to achieve different separation forces.

As discussed above, absorbent articles 100, such as diaper pants 100P, may be configured with frangible pathways 700 comprising lines of weakness 704 arranged in various ways to help improve a caregiver's ability to remove a soiled diaper pant 100P from a wearer without having to remove a soiled diaper pant from a wearer by sliding the soiled diaper pant down the wearer's legs. As discussed above, the frangible pathways 700 may be configured to allow the first elastic belt 106 and/or the second elastic belt 108 to be relatively easily torn along the frangible pathway 700, such as when removing the diaper pant 100P from a wearer. In addition, the frangible pathways 700 may also be configured to provide access to fastener components 707 that may be used to help hold a soiled product in a disposal configuration. The following provides a discussion of example implementations of frangible pathways 700 on diaper pants 100P in the context of the above description of various details of absorbent articles 100, fastener components 707, frangible pathways 700, and lines weakness 704. It is to be appreciated that discussions of frangible pathways 700 in the first elastic belt 106 herein may also apply to frangible pathways 700 in the second elastic belt 108.

Figure 6A:
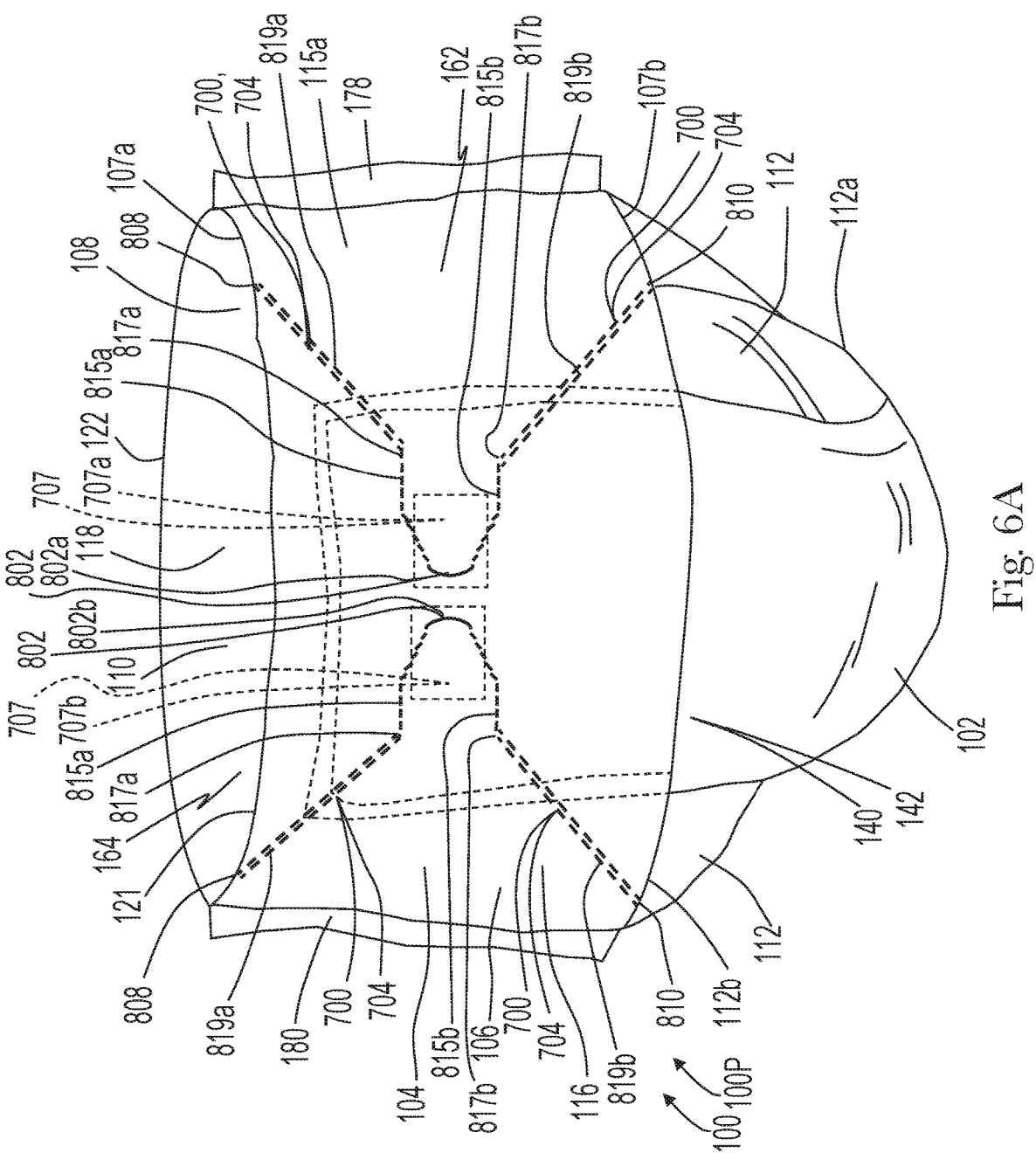
FIG. 6A is a perspective view of a diaper pant with frangible pathways.
Figure 6B:
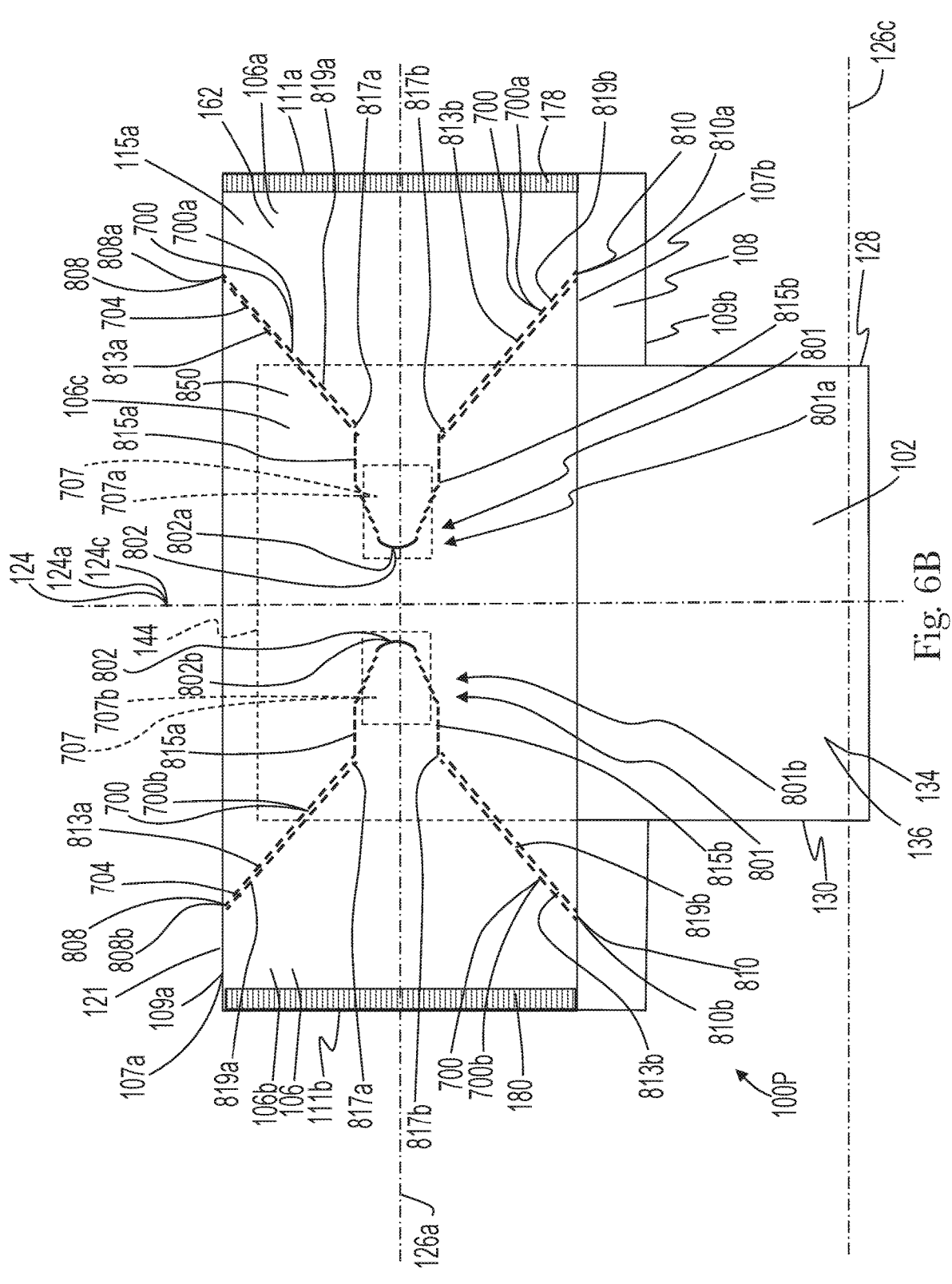
FIG. 6B is a front plan view of the diaper pant of FIG. 6A.

It is to be appreciated that frangible pathways 700 may be positioned in various locations and/or orientations relative to other components of the absorbent article 100 and/or may be configured to function in various ways to help facilitate removal of diaper pant from a wearer. For example, the diaper pant 100P shown in FIGS. 6A and 6B may include one or more frangible pathways 700 extending between a distal terminus 808 on the outer edge 107*a* of the first belt 106 and a distal terminus 810 on the inner edge 107*b* of the first belt 106. As illustrated in FIGS. 6A and 6B, the diaper pant 100P includes a first frangible pathway 700*a* and a second frangible pathway 700*b* in the first belt 106. The first frangible pathway 700*a* may extend between a first distal terminus 808*a* on the outer edge 107*a* of the first belt 106 and a first proximal terminus 810*a* on the inner edge 107*b* of the first belt 106. And the second frangible pathway 700*b* may extend between a second distal terminus 808*b* on the outer edge 107*a* of the first belt 106 and a second proximal terminus 810*b* on the inner edge 107*b* of the first belt 106. It is to be appreciated that the first and second frangible pathways 700*a*, 700*b* may comprise lines of weakness 704 as described above.

It is to be appreciated that the first distal terminus 808*a* and the second distal terminus 808*b* may be located in various lateral positions on the outer edge 107*a* of the first belt 106. For example, in some configurations, the first distal terminus 808*a* and/or the second distal terminus 808*b* may be positioned in the central region 106*c* of the first belt 106. In some configurations, the first distal terminus 808*a* and/or the second distal terminus 808*b* may be positioned laterally between the first longitudinal edge 128 and the second longitudinal edge 130 of the chassis 102. In some configurations, the first distal terminus 808*a* and/or the second distal terminus 808*b* may be positioned in the first end region 106*a* and/or the second end region 106*b* of the first belt 106. In some configurations, the first distal terminus 808*a* and/or the second distal terminus 808*b* may be positioned laterally outboard of the first longitudinal edge 128 and the second longitudinal edge 130 of the chassis 102. In some configurations, the first distal terminus 808*a* and/or the second distal terminus 808*b* may be positioned laterally between the first longitudinal edge 128 of the chassis 102 and the first side seam 178 and/or may be positioned laterally between the second longitudinal edge 130 of the chassis 102 and the second side seam 180. In some configurations, the first distal terminus 808*a* may be laterally aligned with the first longitudinal edge 128 of the chassis 102 or the first longitudinal side edge 111*a* of the first belt 106. In some configurations, the first distal terminus 808*a* may be positioned laterally between the first longitudinal edge 128 of the chassis 102 and the first longitudinal side edge 111a of the first belt 106. In some configurations, the second distal terminus 808b may be laterally aligned with the second longitudinal edge 130 of the chassis 102 or the second longitudinal side edge 111b of the first belt 106. In some configurations, the second distal terminus 808b may be positioned laterally between the second longitudinal edge 130 of the chassis 102 and the second longitudinal side edge 111b of the first belt 106.

It is also to be appreciated that the first proximal terminus 810a and the second proximal terminus 810b may be located in various lateral positions on the inner edge 107b of the first belt 106. For example, in some configurations, the first proximal terminus 810a and/or the second proximal terminus 810b may be positioned in the central region 106c of the first belt 106. In some configurations, the first proximal terminus 810a and/or the second distal terminus 810b may be positioned laterally between the first longitudinal edge 128 and the second longitudinal edge 130 of the chassis 102. In some configurations, the first proximal terminus 810a and/or the second proximal terminus 810b may be positioned in the first end region 106a and/or the second end region 106b of the first belt 106. In some configurations, the first proximal terminus 810a and/or the second proximal terminus 810b may be positioned laterally outboard of the first longitudinal edge 128 and the second longitudinal edge 130 of the chassis 102. In some configurations, the first proximal terminus 810a and/or the second proximal terminus 810b may be positioned laterally between the first longitudinal edge 128 of the chassis 102 and the first side seam 178 and/or may be positioned laterally between the second longitudinal edge 130 of the chassis 102 and the second side seam 180. In some configurations, the first proximal terminus 810a may be laterally aligned with the first longitudinal edge 128 of the chassis 102 or the first longitudinal side edge 111a of the first belt 106. In some configurations, the first proximal terminus 810a may be positioned laterally between the first longitudinal edge 128 of the chassis 102 and the first longitudinal side edge 111a of the first belt 106. In some configurations, the second proximal terminus 810b may be laterally aligned with the second longitudinal edge 130 of the chassis 102 or the second longitudinal side edge 111b of the first belt 106. In some configurations, the second proximal terminus 810b may be positioned laterally between the second longitudinal edge 130 of the chassis 102 and the second longitudinal side edge 111b of the first belt 106.

It is to be appreciated that the first distal terminus 808a and the second distal terminus 808b may be located in various longitudinal positions between the outer edge 107a and the inner edge 107b of the first belt 106. And the first proximal terminus 810a and the second proximal terminus 810b may be located in various longitudinal positions between the outer edge 107a and the inner edge 107b of the first belt 106. For example, in some configurations, such as shown in FIG. 6B1 for example, the first distal terminus 808a and/or the first proximal terminus 810a may be located on the first side seam 178 at positions longitudinally inboard of the outer edge 107a and longitudinally outboard of the inner edge 107b of the first belt 106. Also, as shown in FIG. 6B1, the second distal terminus 808b and/or the second proximal terminus 810b may be located on the second side seam 180 at positions longitudinally inboard of the outer edge 107a and longitudinally outboard of the inner edge 107b of the first belt 106. As such, completing the tearing process of the first belt 106 may also require tearing portions of the first and/or second side seams 178, 180.

With continued reference to FIG. 6B, the first belt 106 may also comprise grip regions 801 providing a place where a user may grasp a portion of the first belt 106 and begin the process of tearing the first belt along the frangible pathway 700. The grip region 801 may comprise an accessibility opening 802 in the first belt 106 and may also comprise a fastener component 707 positioned adjacent the accessibility opening 802. The accessibility opening 802 may comprise slits and/or openings in the first belt 106 and may penetrate through some or all layers of the first belt 106. It is to be appreciated that such slits or openings may be curved and/or straight. The accessibility opening 802 may also be considered part of the frangible pathway 700.

As shown in FIG. 6B, the diaper pant 100P may include a first grip region 801a including a first accessibility opening 802a and second grip region 801b including a second accessibility opening 802b in the first belt 106. The first and second accessibility openings 802a, 802b may be positioned between the outer edge 107a and the inner edge 107b of the first belt 106. The first and second accessibility openings 802a, 802b may also be positioned in the central region 106c of the first belt 106 and may be positioned between the first longitudinal edge 128, the second longitudinal edge 130 of the chassis 102, and the first lateral edge 144 of the chassis 102. In addition, a first fastener component 707a may be positioned adjacent the first accessibility opening 802a, and a second fastener component 707a may be positioned adjacent the second accessibility opening 802a. The first frangible pathway 700a may comprise a first tear zone 813a extending from the first accessibility opening 802a to the first distal terminus 808a and a second tear zone 813b extending from the first accessibility opening 802a to the first proximal terminus 810a. The second frangible pathway 700b may comprise a first tear zone 813a extending from the second accessibility opening 802b to the second distal terminus 808b and a second tear zone 813b extending from the second accessibility opening 802b to the second proximal terminus 810b.

It is to be appreciated that the frangible pathways 700 may comprise one or more functional zones. In turn, the frangible pathways may comprise transition zones that may operatively connect such zones to help facilitate propagation of a tear along the frangible pathway 700 from one zone to another zone. The lines of weakness in the transition zones may be of particular lengths and/or angles relative to lateral centerlines and row spacing to help provide desired propagation of material failure when, for example, removing a product from a wearer. It is to be appreciated that the lengths, angles, and spacings in transition zones may be different from those in adjacent lines of weakness.

As shown in FIG. 6B for example, the first tear zone 813a of the first frangible pathway 700a may comprise a first initial tear zone 815a extending from the first accessibility opening 802a to a first transition zone 817a. In addition, the first tear zone 813a of the first frangible pathway 700a may comprise a secondary tear zone 819a extending from the first transition zone 817a to the first distal terminus 808a. The first tear zone 813a of the first frangible pathway 700a may also comprise a second initial tear zone 815b extending from the first accessibility opening 802a to a second transition zone 817b. Further, the first tear zone 813a of the first frangible pathway 700a may comprise a second secondary tear zone 819b extending from the second transition zone 817b to the first proximal terminus 810a. The first transition zone 817a may operatively connect the first initial tear zone 815a with the first secondary tear zone 819a to help facilitate the propagation of the tear along the first frangible pathway 700*a* from first initial tear zone 815*a* to the first secondary tear zone 819*a*. With continued reference to FIG. 6B, the first tear zone 813*a* of the second frangible pathway 700*b* may comprise a first initial tear zone 815*a* extending from the second accessibility opening 802*b* to a first transition zone 817*a*. In addition, the first tear zone 813*a* of the second frangible pathway 700*b* may comprise a secondary tear zone 819*a* extending from the first transition zone 817*a* to the second distal terminus 808*b*. The first tear zone 813*a* of the second frangible pathway 700*b* may also comprise a second initial tear zone 815*b* extending from the second accessibility opening 802*b* to a second transition zone 817*b*. Further, the first tear zone 813*a* of the second frangible pathway 700*b* may comprise a second secondary tear zone 819*b* extending from the second transition zone 817*b* to the second proximal terminus 810*b*. The second transition zone 817*b* may operatively connect the second initial tear zone 815*b* with the second secondary tear zone 819*b* to help facilitate the propagation of the tear along the second frangible pathway 700*b* from second initial tear zone 815*b* to the second secondary tear zone 819*b*.

As discussed in more detail below, the accessibility opening 802 may help provide a caregiver or wearer access to and/or to grasp the fastener component 707 in the grip region 801 with a finger or thumb. The caregiver or user may then pull on grip region 801 to begin tearing the first belt 106 on the frangible pathway 700. In some configurations, tear lines may simultaneously propagate along the first tear zone 813*a* and the second tear zone 813*b* laterally outward from the central region 106*c* of the first belt 106 toward the distal terminus 808 and the proximal terminus 810. It is to be appreciated that the diaper pant 100P may also be configured such that a tear line propagating along the first tear zone 813*a* and a tear line propagating along the second tear zone 813*b* may reach the distal terminus 808 and the proximal terminus 810, respectively, simultaneously or approximately simultaneously. It is also to be appreciated that some diaper pants 100P herein may be configured to include a frangible pathway 700 that extends through or around the fastener component 707 without an accessibility opening. In turn, a user may pinch and/or pull the belt where the frangible pathway 700 is located at or adjacent the fastener component 707 to initiate the tearing process along the frangible pathway 700.

As shown in FIG. 6B, the frangible pathways 700 may be configured to extend laterally inward from the from the distal terminus 808 and/or the proximal terminus 810. In turn, portions of the frangible pathway 700 may extend to define an angle that is less than 90 degrees with respect to the outer edge 107*a* and/or the inner edge 107*b* of the first belt 106. Thus, the frangible pathway may define an overall length that is greater than a longitudinal length LT1 of the first belt 106 and/or the longitudinal length LT2 of the second belt 108 discussed above with reference to FIGS. 2C-2E.

As discussed above, the first elastic belt 106 and/or the second belt 108 may be relatively easily torn along the frangible pathway 700, such as when removing the diaper pant 100P from a wearer. As discussed below with reference to FIGS. 6A-6F, the frangible pathway 700 may be configured to allow a caregiver or wearer to initiate and/or completely tear the first belt 106 and/or the second belt 108 with one hand when removing a diaper pant 100P from a wearer. In addition, the first belt 106 may be separable along the first frangible pathway 700*a* and the second frangible pathway 700*b* to define a first belt zone 831, a second belt zone 832, and a third belt zone 833 positioned laterally between the first and second belt zones 831, 832.

Referring now to FIGS. 6A and 6B, when removing a diaper pant 100P from a wearer, a user may grab the first belt 106 in the grip region 801 by inserting one or more fingers and/or a thumb through the accessibility opening 802 to grasp a portion of the first 106 and fastener component 707. For example, with reference to FIGS. 6B and 6C, a caregiver may insert a finger or thumb through the first accessibility opening 802*a* and grasp the first belt 106 and the first fastener component 707*a* with a first hand. The caregiver's opposing second hand may be used to help stabilize the wearer. For example, the caregiver's opposing second hand may apply a holding or stabilizing force to the wearer at the central region 106*c* of the first belt 106. The user's first hand may then exert a pulling force Fp on the first grip region 801*a* of the first belt 106 outward away from the wearer to initiate a tearing of the first belt 106 along the first frangible pathway 700*a*, such as shown in FIG. 6C.

Figure 6C:
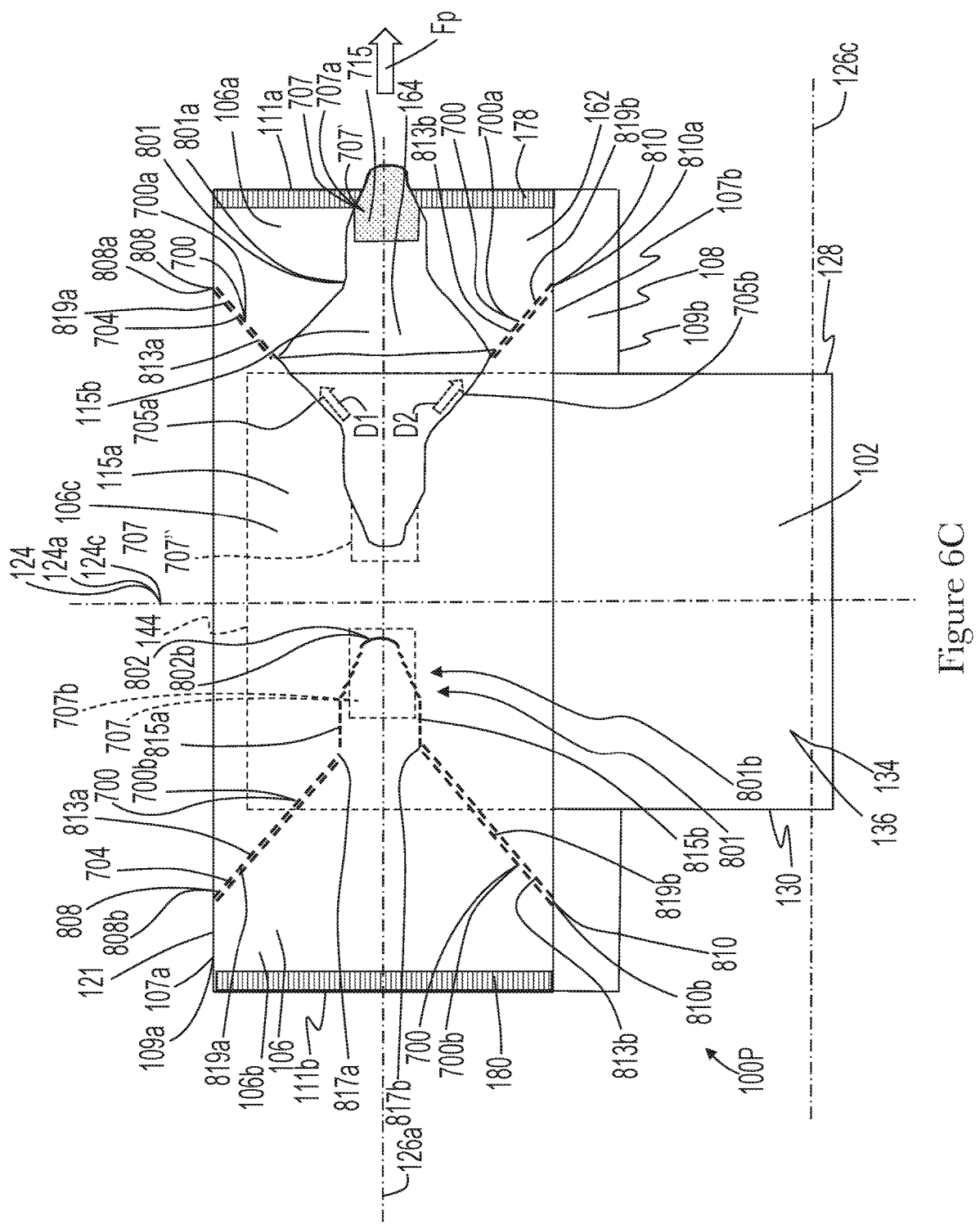
FIG. 6C shows a front plan view of the diaper pant of FIG. 6B as a first frangible pathway is being torn.

With continued reference to FIG. 6C, a pulling force Fp (generally represented by an arrow) may be applied to the first grip region 801*a* in a direction generally toward the first end region 106*a* of the first belt 106 and/or outward away from the first belt 106 and the wearer. As the force Fp is applied, a first tear line 705*a* and a second tear line 705*b* may simultaneously propagate along the first tear zone 813*a* and the second tear zone 813*b*, respectively. The first tear line 705*a* may propagate from the first accessibility opening 802*a* along the first tear zone 813*a* of the first frangible pathway 700*a* in longitudinal and lateral directions partially through and adjacent to the first fastener component 707*a* and then in a direction D1 that is generally laterally and longitudinally outward from the central region 106*c* of the first belt 106 and toward the first distal terminus 808*a* in the first end region 106*a* of the first belt 106. Simultaneously, the second tear line 705*b* may propagate from the first accessibility opening 802*a* in longitudinal and lateral directions partially through and adjacent to the first fastener component 707*a* along the second tear zone 813*b* of the first frangible pathway 700*a* in a direction D2 that is generally laterally outward and longitudinally inward from the central region 106*c* of the first belt 106 and toward the first proximal terminus 810*a* in the first end region 106*a* of the first belt 106.

In some configurations, the first tear line 705*a* may propagate from the first accessibility opening 802*a* along the first initial tear zone 815*a* of the first frangible pathway 700*a* to the first transition zone 817*a*. From the first transition zone 817*a*, the first tear line 705*a* may then propagate along the first secondary tear zone 819*a* to the first distal terminus 808*a*. In addition, the second tear line 705*b* may propagate from the first accessibility opening 802*a* along the second initial tear zone 815*b* of the first frangible pathway 700*a* to the second transition zone 817*b*. From the second transition zone 817*b*, the second tear line 705*b* may then propagate along the second secondary tear zone 819*b* to the first proximal terminus 810*a*. It is to be appreciated that the first frangible pathway 700*a* may be configured such that the first tear line 705*a* and the second tear line 705*b* may reach first distal terminus 808*a* and the first proximal terminus 810*a*, respectively, at the same time or about the same time.

Figure 6D:
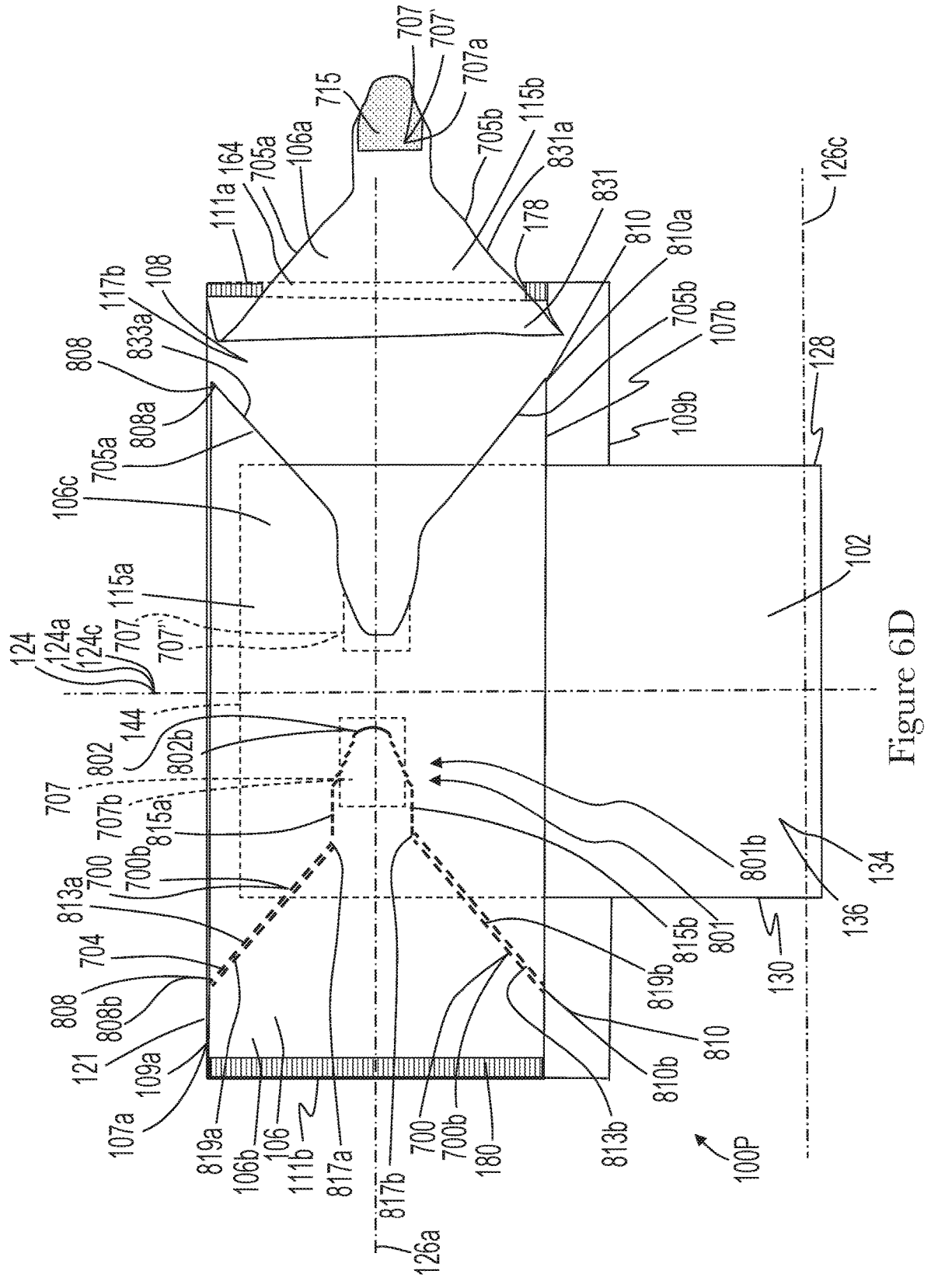
FIG. 6D shows a front plan view of the diaper pant of FIG. 6C after the first frangible pathway has been completely torn.

As shown in FIG. 6D, the first belt 106 may be separable along the first frangible pathway 700*a* to define a first belt zone 831. For example, the first belt zone 831 may be formed once the first tear line 705*a* propagates through the first distal terminus 808*a* and the second tear line 705*b* propagates through to the first proximal terminus 810*a*, the first belt zone 831 may be formed. As shown in FIG. 6D, a first edge 831*a* of the first belt zone 831 is formed by tearing the first frangible pathway 700*a*. In addition, a first edge 833*a* of the third belt zone 833 discussed in more detail below is also formed by tearing the first frangible pathway 700*a*. The first belt zone 831 may extend from the first edge 831*a* of the first and second tear lines 705*a*, 705*b* to the first side seam 178 or the first longitudinal side edge 111*a* of the first belt 106. In addition, the first belt zone 831 may include the first fastener component 707*a*. As discussed below, the first belt zone 831 may include the entirety of or a portion of first fastener component 707*a*.

Figure 6E:
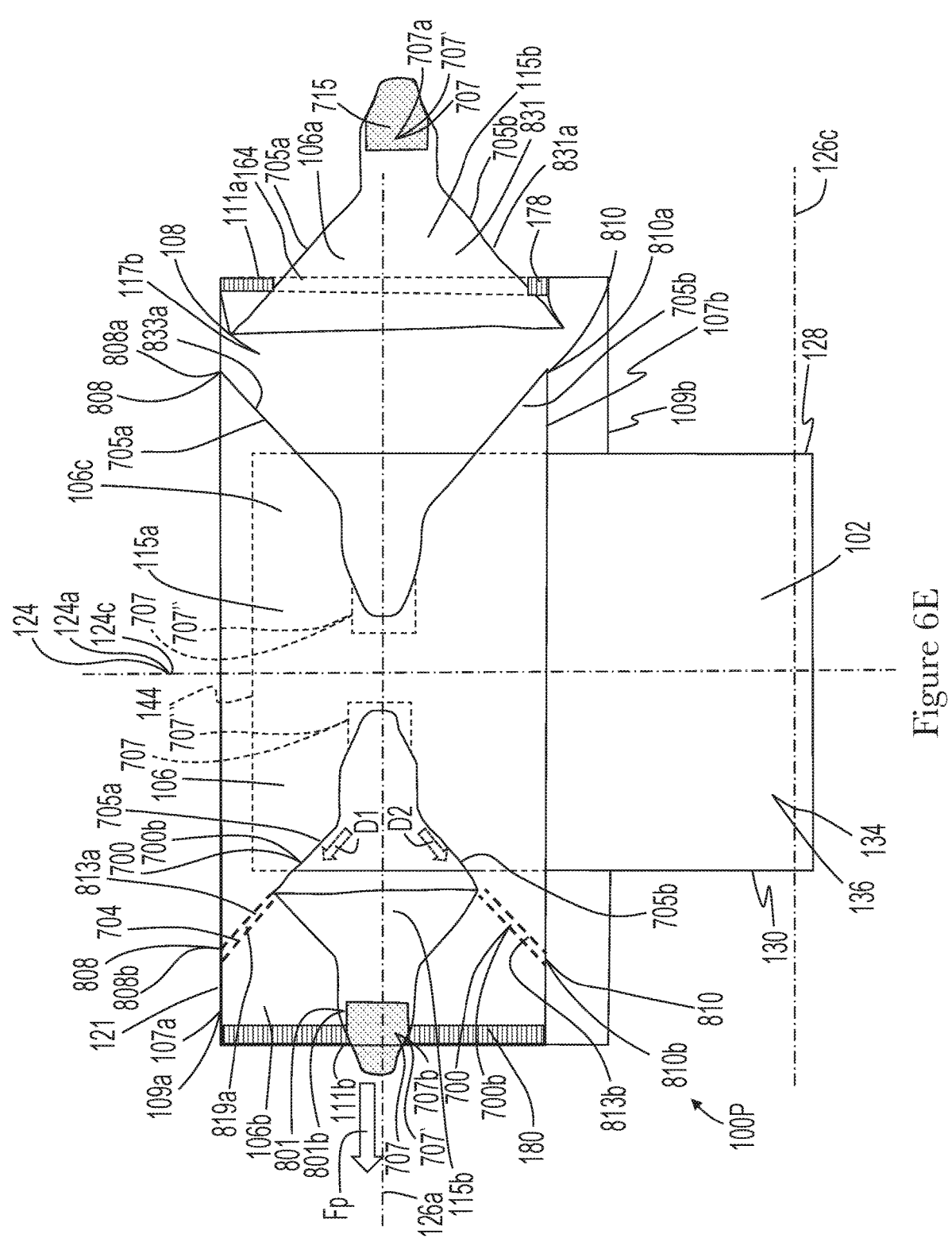
FIG. 6E shows a front plan view of the diaper pant of FIG. 6D as a second frangible pathway is being torn.

With the first belt zone 831 being defined by tearing the first belt 106 along the first frangible pathway 700*a*, a user may proceed to define the second belt zone 832 by tearing the first belt 106 along the second frangible pathway 700*b*. Referring now to FIGS. 6D and 6E, a caregiver may insert a finger or thumb through the second accessibility opening 802*b* and grasp the first belt 106 and the second fastener component 707*b* with a first hand. The caregiver's opposing second hand may be used to help stabilize the wearer. For example, the caregiver's opposing second hand may apply a holding or stabilizing force to the wearer at the central region 106*c* of the first belt 106. The user's first hand may then exert a pulling force Fp on the second grip region 801*b* of the first belt 106 outward away from the wearer to initiate a tearing of the first belt 106 along the second frangible pathway 700*b*, such as shown in FIG. 6E.

With continued reference to FIG. 6E, a pulling force Fp (generally represented by an arrow) is applied to the second grip region 801*b* in a direction generally toward the second end region 106*b* of the first belt 106 and/or outward away from the first belt 106. As the pulling force Fp is applied, a first tear line 705*a* and a second tear line 705*b* may simultaneously propagate along the first tear zone 813*a* and the second tear zone 813*b*, respectively. The first tear line 705*a* may propagate from the second accessibility opening 802*b* along the first tear zone 813*a* of the second frangible pathway 700*b* in longitudinal and lateral directions partially through and adjacent to the second fastener component 707*b* and then in a direction D1 that is generally laterally and longitudinally outward from the central region 106*c* of the first belt 106 and toward the second distal terminus 808*b* in the second end region 106*b* of the first belt 106.

Simultaneously, the second tear line 705*b* may propagate from the second accessibility opening 802*b* in longitudinal and lateral directions partially through and adjacent to the second fastener component 707*b* along the second tear zone 813*b* of the second frangible pathway 700*b* in a direction D2 that is generally laterally outward and longitudinally inward from the central region 106*c* of the first belt 106 and toward the second proximal terminus 810*b* in the second end region 106*b* of the first belt 106.

In some configurations, the first tear line 705*a* may propagate from the second accessibility opening 802*b* along the first initial tear zone 815*a* of the second frangible pathway 700*b* to the first transition zone 817*a*. From the first transition zone 817*a*, the first tear line 705*a* may then propagate along the first secondary tear zone 819*a* to the second distal terminus 808*b*. In addition, the second tear line 705*b* may propagate from the second accessibility opening 802*b* along the second initial tear zone 815*b* of the second frangible pathway 700*b* to the second transition zone 817*b*. From the second transition zone 817*b*, the second tear line 705*b* may then propagate along the second secondary tear zone 819*b* to the second proximal terminus 810*b*. It is to be appreciated that the second frangible pathway 700*b* may be configured such that the first tear line 705*a* and the second tear line 705*b* may reach second distal terminus 808*b* and the second proximal terminus 810*b*, respectively, at the same time or about the same time.

Figure 6F:
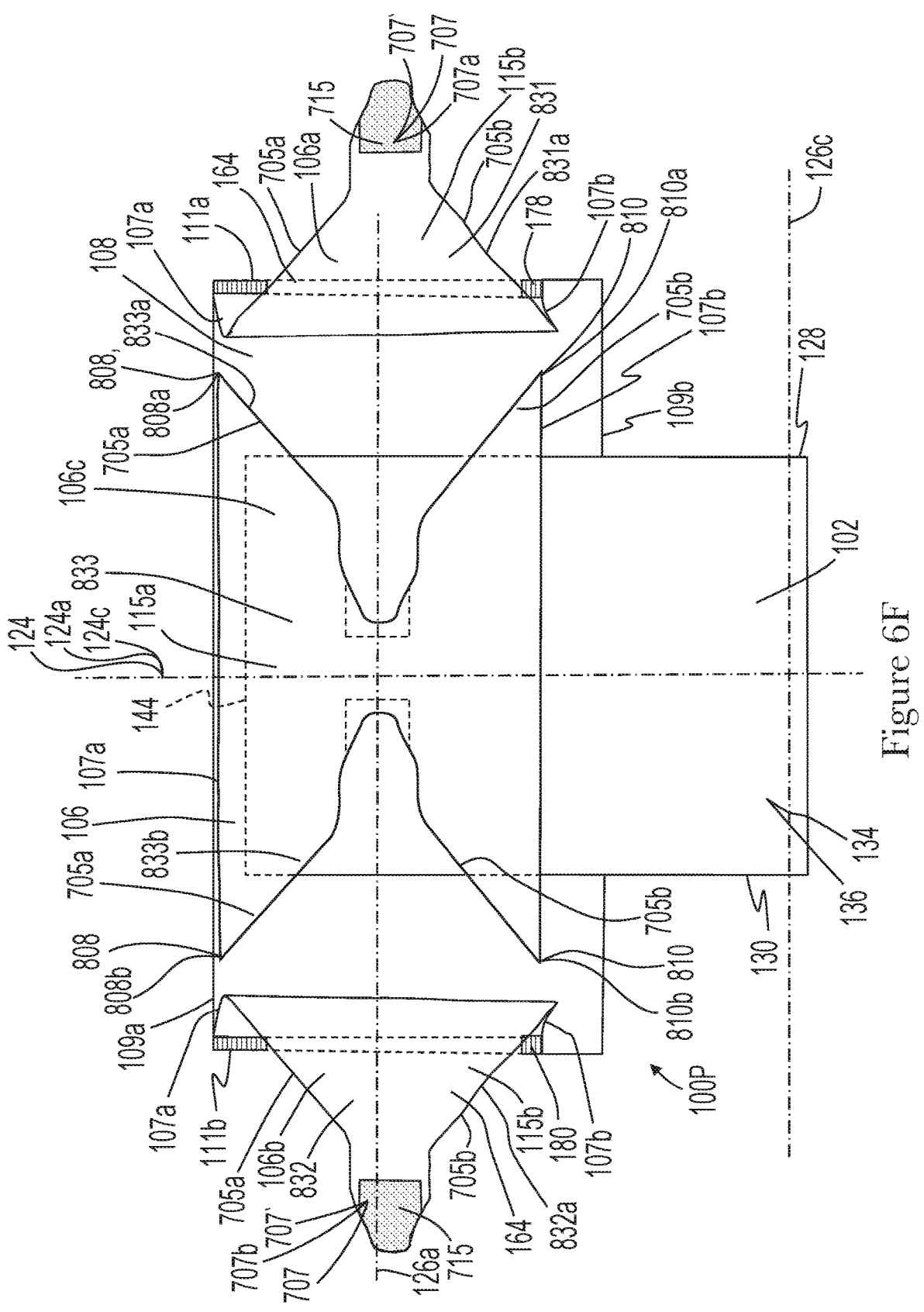
FIG. 6F shows a front plan view of the diaper pant of FIG. 6E after the second frangible pathway has been completely torn.

As shown in FIG. 6F, the first belt 106 may be separable along the second frangible pathway 700*b* to define a second belt zone 832 and a third belt zone 833. For example, the second belt zone 832 may be formed once the first tear line 705*a* propagates through the second distal terminus 808*b* and the second tear line 705*b* propagates through to the second proximal terminus 810*b*, the second belt zone 832 may be formed. As shown in FIG. 6F, a first edge 832*a* of the second belt zone 832 is formed by tearing the second frangible pathway 700*b*. In addition, a second edge 833*b* of the third belt zone 833 is also formed by tearing the second frangible pathway 700*b*. The second belt zone 832 may extend from the first edge 832*a* of the first and second tear lines 705*a*, 705*b* to the second side seam 180 or the second longitudinal side edge 111*b* of the first belt 106. In addition, the second belt zone 832 may include the second fastener component 707*b*. The third belt zone 833 may extend laterally between the first edge 833*a* and the second edge 833*b* and may remain connected with the chassis 102.

Although the tearing process is described above with reference to FIGS. 6A-6F as tearing the first belt 106 along the first frangible pathway 700*a* before tearing the first belt along the second frangible pathway 700*b*, it is to be appreciated that the tearing of first belt 106 along the frangible pathways 700 may occur in various different orders and in different manners. For example, the first belt 106 may be torn along second frangible pathway 700*b* to define the second belt zone 832 before tearing the first belt 106 along the first frangible pathway 700*a* to define the first belt zone 831. In another example, the first belt 106 may be torn simultaneously along the first frangible pathway 700*a* and the second frangible pathway 700*b* to define the first belt zone 831, the second belt zone 832, and the third belt zone 833.

Once the first belt 106 is torn along the frangible pathways 700 to define the first belt zone 831, the second belt zone 832, and the third belt zone 833, the diaper pant 100P may be removed from a wearer in a manner similar to that of a conventional taped diaper. After being removed from a wearer, the diaper pant 100P may be placed in a disposal configuration, such as discussed above with reference to FIGS. 5A and 5B, by rolling and/or folding the chassis 102 onto itself in a longitudinal direction. The first belt zone 831 and the second belt zone 832 may be used to further wrap the diaper pant 100P onto itself. And the fastener components 707 on the first belt zone 831 and the second belt zone 832 may be connected with another portion of the diaper pant 100P to help maintain the diaper pant 100P in the disposal configuration.

As described above, frangible pathways 700 may be configured such that the first tear line 705*a* and the second tear line 705*b* may propagate to reach the distal terminus 808 and the proximal terminus 810, respectively, simultaneously or approximately simultaneously. Such simultaneous tear propagation and tear termination may help provide a caregiver with a convenient and confident diaper pant removal experience. On occasions when one of the first tear line 705*a* or the second tear line propagates through the distal terminus 808 or the proximal terminus 810, respectively, significantly in advance of the other tear line, the pulling force needed to complete the tearing may be reduced. In turn, the reduction of force may cause the caregiver to believe the tearing is completed and to stop the tearing process before completion.

As such, the caregiver may need to initiate a second tearing motion to complete the tearing process.

Figure 7A:
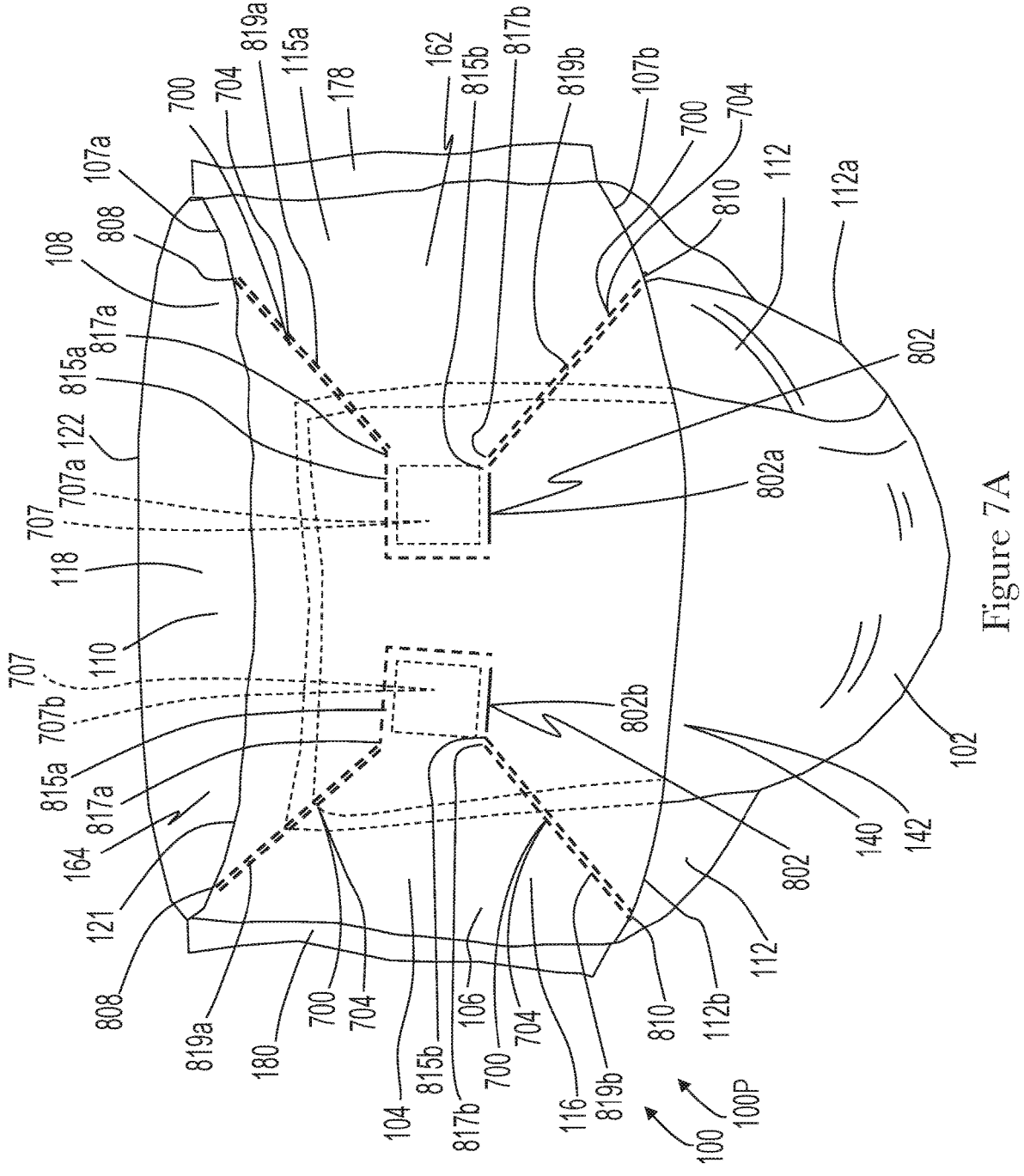
FIG. 7A is a perspective view of a diaper pant with another configuration of frangible pathways.
Figure 7B:
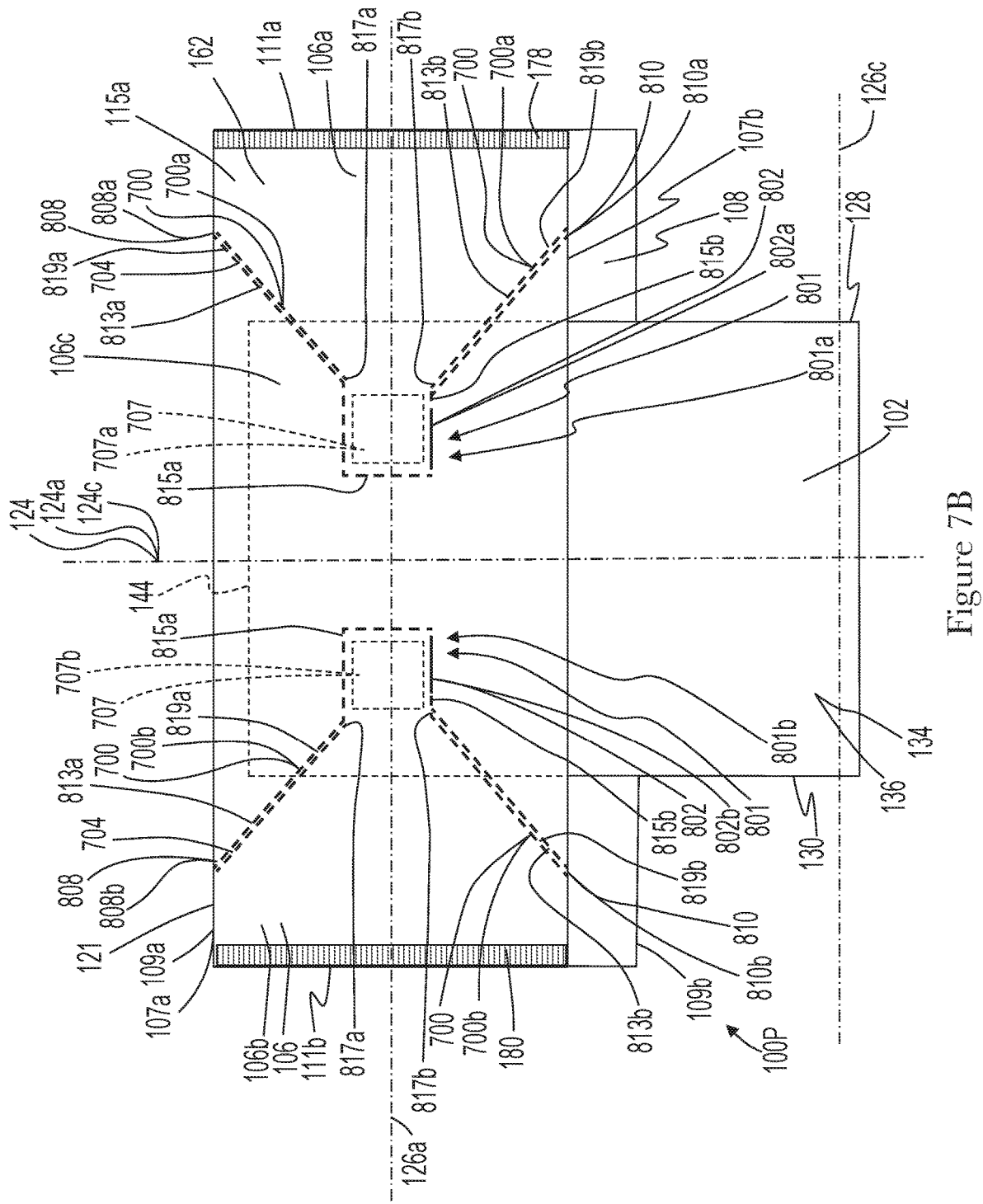
FIG. 7B is a front plan view of the diaper pant of FIG. 7A.
Figure 7C:
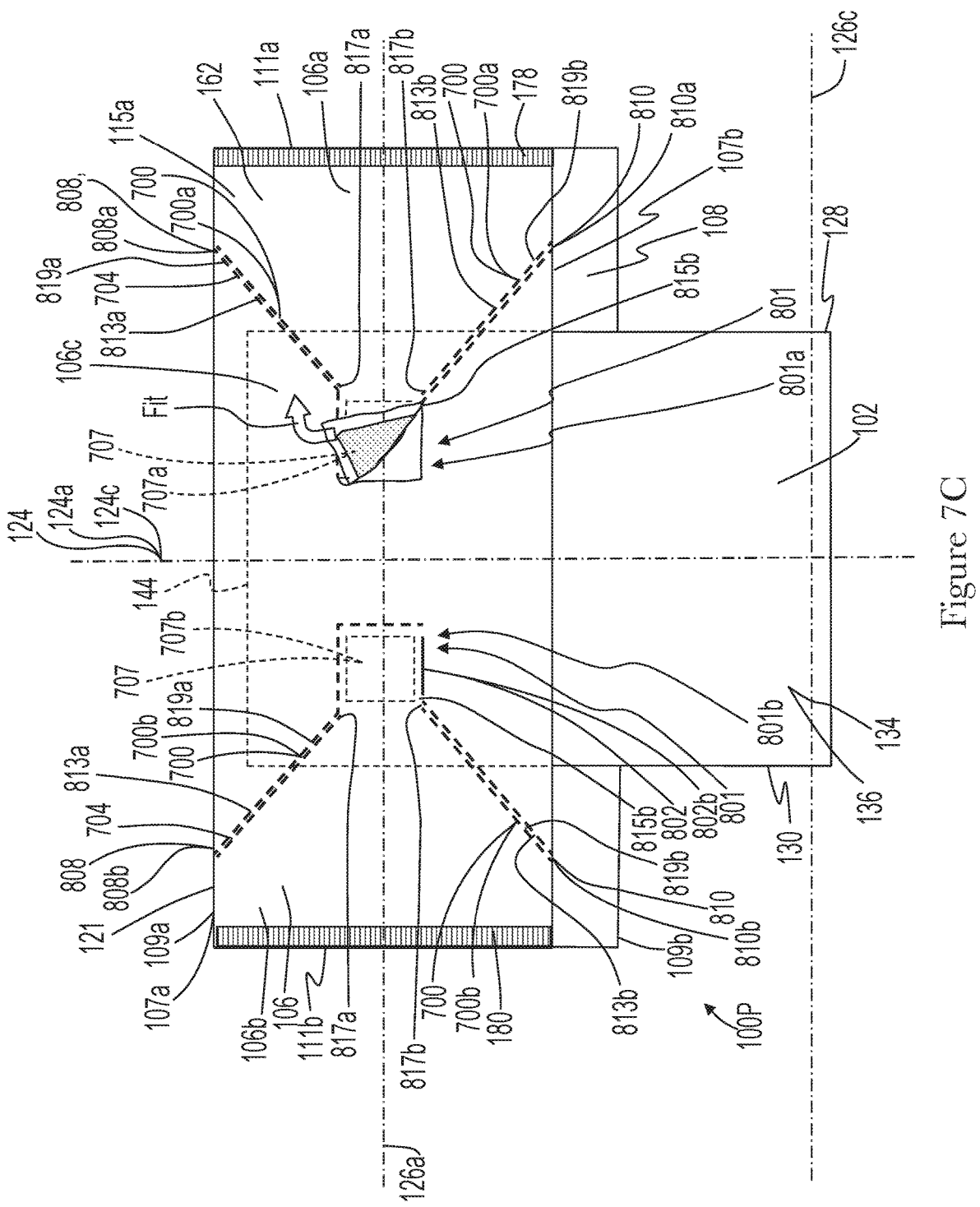
FIG. 7C shows a front plan view of the diaper pant of FIG. 7B as a first frangible pathway is being torn along first and second initial tear zones.
Figure 7D:
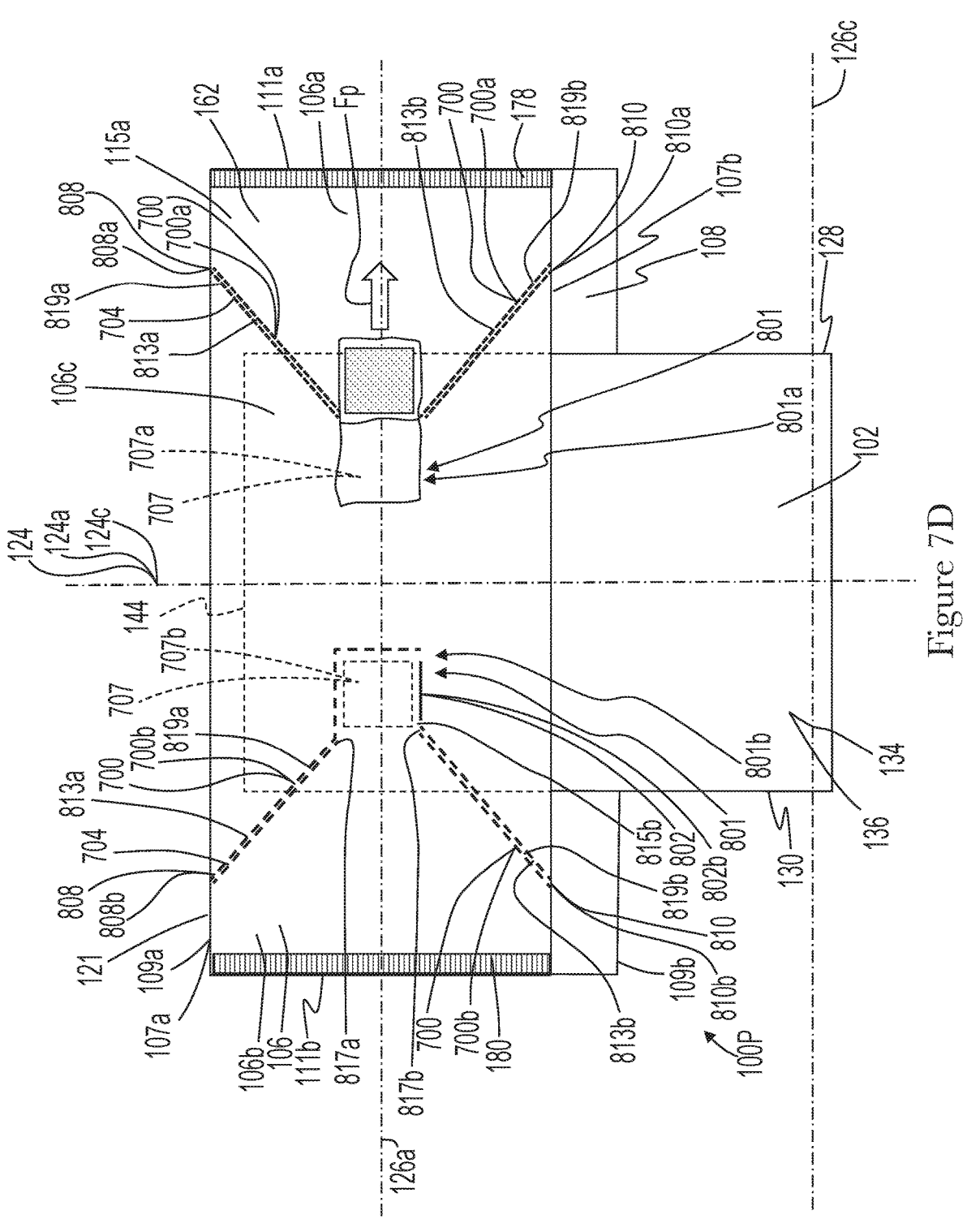
FIG. 7D shows a front plan view of the diaper pant of FIG. 7C after a first frangible pathway has been torn along first and second initial tear zones.

Referring now to FIGS. 7A and 7B, when removing a diaper pant 100P from a wearer, a user may grab the first belt 106 in the grip region 801 by inserting one or more fingers and/or a thumb through the accessibility opening 802 to grasp a portion of the first 106 and fastener component 707. For example, with reference to FIGS. 7B and 7C, a caregiver may insert a finger or thumb through the first accessibility opening 802a and grasp the first belt 106 and the first fastener component 707a with a first hand. The caregiver's opposing second hand may be used to help stabilize the wearer, as discussed above. The user's first hand may then exert an initial tear force Fit (generally represented by a curved arrow) on the first grip region 801a of the first belt 106 outward away from the wearer to initiate a tearing of the first belt 106 along the first initial tear zone 815a and the second initial tear zone 815b, such as shown in FIG. 7C. As the initial tear force Fit is applied, a first tear line 705a may propagate from the accessibility opening 802 along the first initial tear zone 815a in longitudinal and lateral directions around the first fastener component 707a and then to the first transition zone 817a, such as shown in FIGS. 7C and 7D. In addition, a second tear line 705b may propagate in a lateral direction from the accessibility opening 802 along the second initial tear zone 815b to the second transition zone 817b.

Figure 7E:
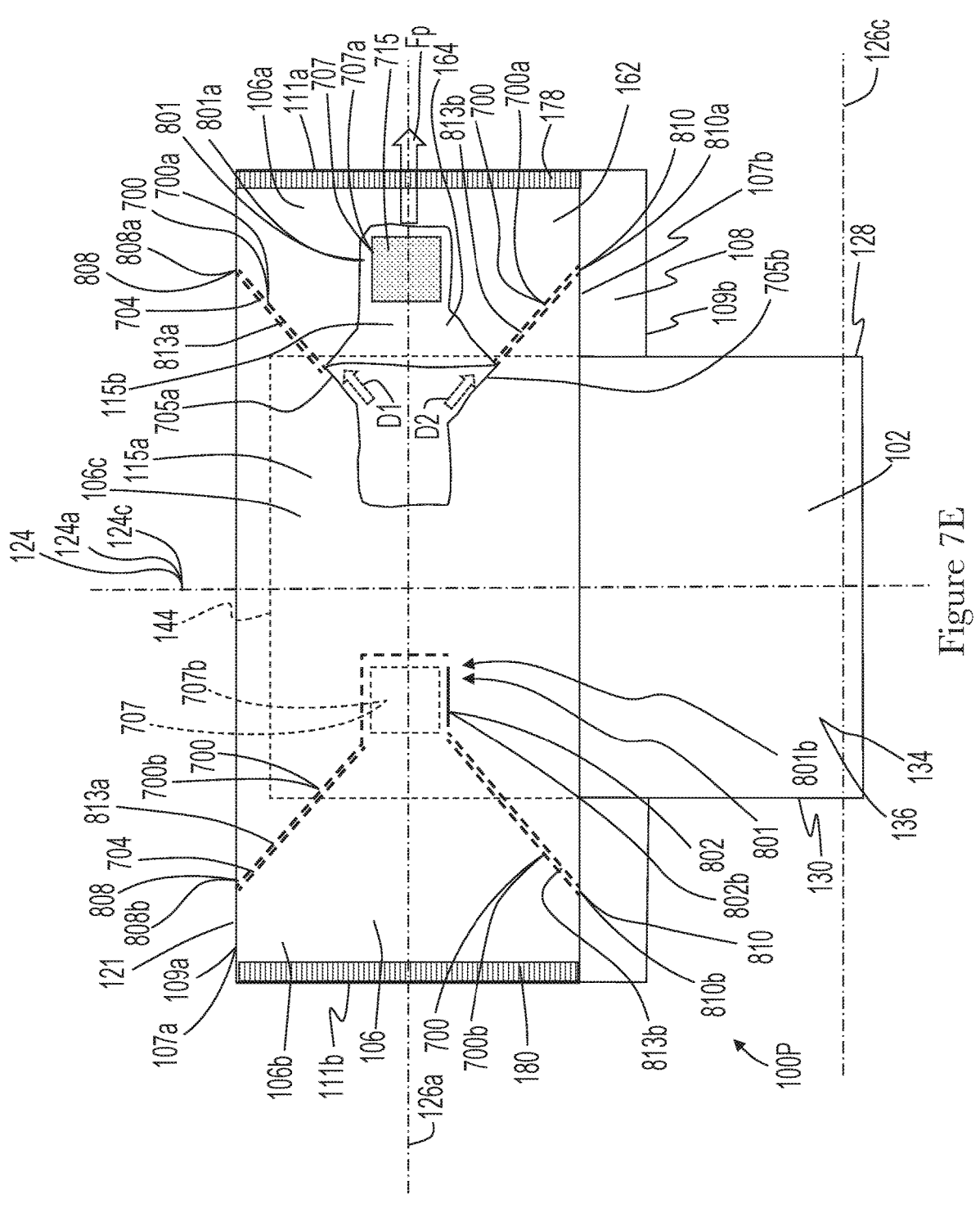
FIG. 7E shows a front plan view of the diaper pant of FIG. 7D as the first frangible pathway is being torn along first and second secondary tear zones.
Figure 7F:
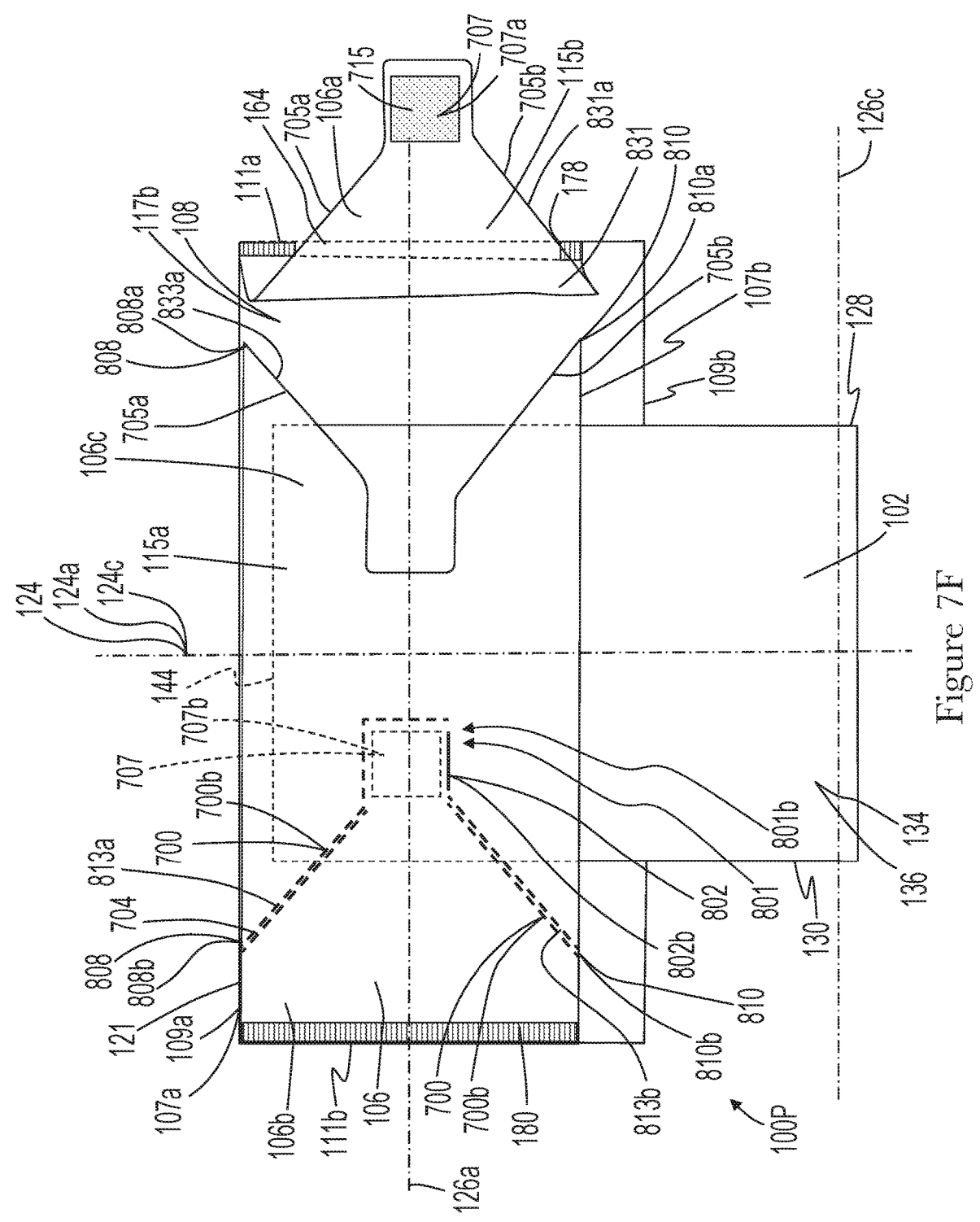
FIG. 7F shows a front plan view of the diaper pant of FIG. 7E after the first frangible pathway has been completely torn.

With reference to FIGS. 7D and 7E, once the first initial tear zone 815a and the second initial tear zone 815b are completely separated, a pulling force Fp (generally represented by an arrow) may be applied to the first grip region 801a in a direction generally toward the first end region 106a of the first belt 106 and/or outward away from the first belt 106 and the wearer. As the pulling force Fp is applied, the first tear line 705a and the second tear line 705b may simultaneously propagate along the first secondary tear zone 819a and the second secondary tear zone 819b, respectively. The first tear line 705a may propagate from the first transition zone 817a along the first secondary tear zone 819a of the first frangible pathway 700a in a direction D1 that is generally laterally and longitudinally outward from the central region 106c of the first belt 106 and toward the first distal terminus 808a in the first end region 106a of the first belt 106. Simultaneously, the second tear line 705b may propagate from the second transition zone 817b along the second secondary tear zone 819b of the first frangible pathway 700a in a direction D2 that is generally laterally outward and longitudinally inward from the central region 106c of the first belt 106 and toward the first proximal terminus 810a in the first end region 106a of the first belt 106. As shown in FIGS. 7E and 7F, the second frangible pathway 700b may be configured such that the first tear line 705a and the second tear line 705b may reach second distal terminus 808b and the second proximal terminus 810b, respectively, at the same time or about the same time.

With reference to various aspects of the Figures described above, it is to be appreciated that grip regions 801 and accessibility openings 802 may be located in various positions in the first end region 106a, the second end region 106b, and/or the central region 106c of the first belt 106. Grip regions 801 and accessibility openings 802 may be positioned between the first longitudinal side edge 111a, the second longitudinal side edge 111b, the outer edge 107a, and the inner edge 107b of the first belt 106. For example, the first accessibility opening 802a and/or the second accessibility 802b may be entirely laterally positioned between the first longitudinal edge 128 and the second longitudinal edge 130 of the chassis 102. In some configurations, the first accessibility opening 802a may be positioned laterally between the first longitudinal side edge 128 of the chassis 102 and the first longitudinal side edge 111a of the first belt 106 and/or first side seam 178. In some configurations, the second accessibility opening 802b may be positioned laterally between the second longitudinal side edge 130 of the chassis 102 and the second longitudinal side edge 111b of the first belt 106 and/or second side seam 180. In some configurations, the first accessibility opening 802a and/or the second accessibility opening 802b may be positioned longitudinally between the first lateral edge 144 of the chassis 102 and the inner edge 107b of the first belt 106 and/or may be positioned longitudinally between the first lateral edge 144 of the chassis 102 and the outer edge 107a of the first belt 106. In some configurations, the first accessibility opening 802a may extend across the first longitudinal edge 128 and/or the first lateral edge 144 of the chassis 102, and/or the second accessibility opening 802b may extend across the second longitudinal edge 130 and/or the first lateral edge 144 of the chassis 102.

It is also to be appreciated that accessibility openings 802 may be located in various positions relative to fastener components 707. For example, in some configurations, the accessibility opening 802 may be positioned longitudinally between the fastener component 707 and the outer edge 107a of the first belt 106. In some configurations, the accessibility opening 802 may be positioned longitudinally between the fastener component 707 and the inner edge 107b of the first belt 106. In some configurations, the accessibility opening 802 may be positioned laterally inboard of the fastener component 707. It is also to be appreciated that more than one accessibility opening 802 may be located adjacent a fastener component 707. As discussed in more detail below, the accessibility opening 802 also be configured to extend partially or entirely through a fastener component 707 and may divide a fastener component 707 into two or more parts.

As mentioned above, the accessibility opening 802 may comprise slits and/or openings in the first belt 106 and may be curved and/or straight. It is to be appreciated that the accessibility openings 802 may also be oriented in various ways. For example, the accessibility opening 802 may be generally oriented perpendicularly relative to the outer edge 107a and/or the inner edge 107b of the first belt 106. In some configurations, the accessibility opening 802 may be generally oriented parallel relative to the outer edge 107a and/or the inner edge 107b of the first belt 106. In some configurations, the accessibility opening 802 may comprise a slit that extends along a line in a lateral direction to define an angle from about 0 degrees to about 45 degrees with respect to the outer edge 107a and/or the inner edge 107b of the first belt 106, specifically reciting all 1 degree increments within the above-recited range and all ranges formed therein or thereby. In some configurations, the accessibility opening 802 may define a length dimension in the range of about 5 mm to about 50 mm, specifically reciting all 0.1 mm increments within the above-recited range and all ranges formed therein or thereby.

Figures 8A, 9A, 9B:
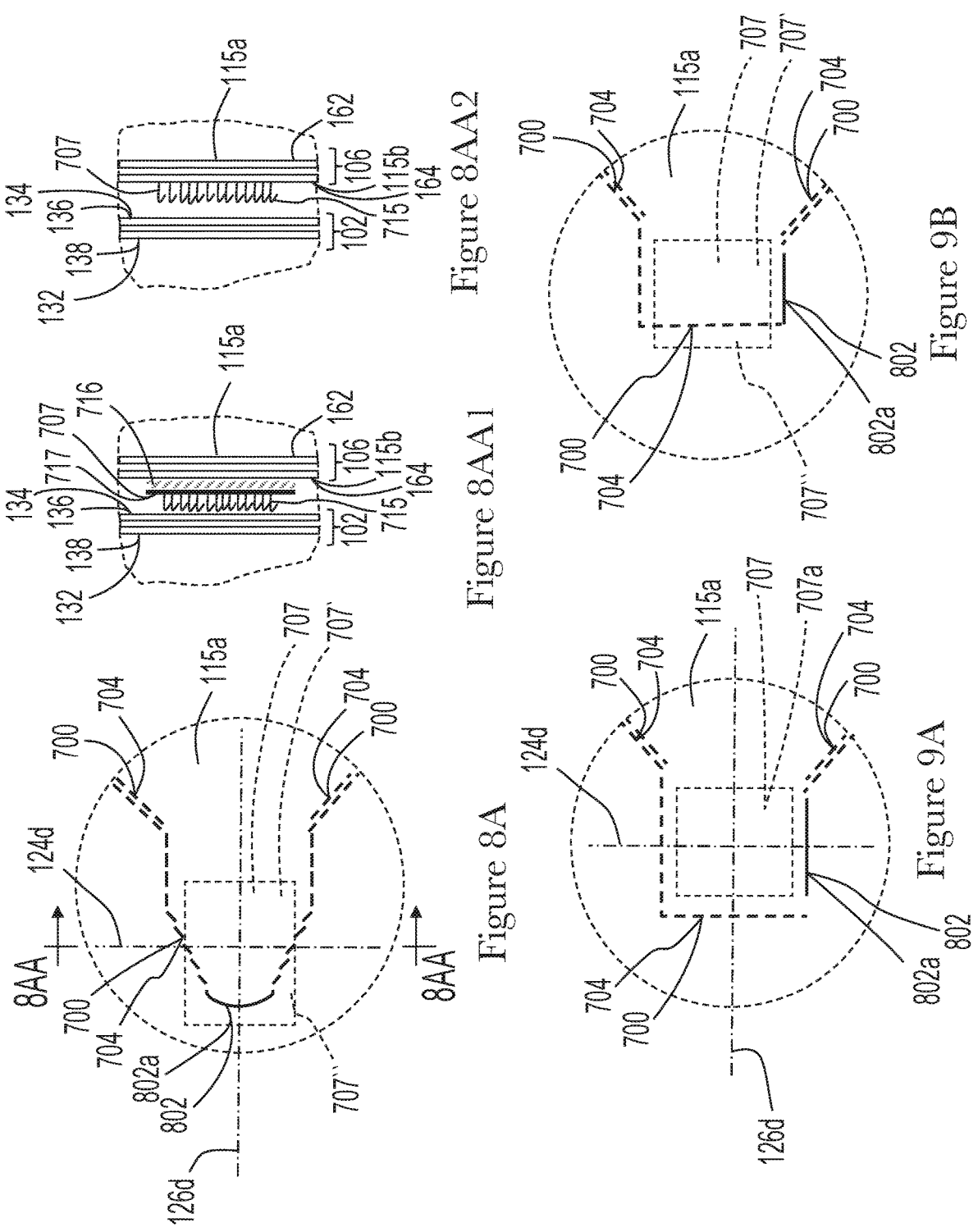
FIG. 8A is a detailed view of a fastener component configuration of FIG. 6A.
FIG. 9A is a detailed view of another fastener component configuration of FIG. 7A.
FIG. 9B is a detailed view of another fastener component configuration.

As discussed above, the diaper pant 100P may include one or more fastener components 707 adapted to refastenably connect with at least one other component of the diaper pant 100P in a disposal configuration. It is to be appreciated that the fastener components 707 may be configured in various shapes and sizes, and may be located in various positions relative to other components of the diaper pant 100P. As shown in FIGS. 8A and 9A for example, the fastener components 707 may comprise a lateral centerline 126d oriented substantially parallel to the lateral centerline 126a of the first elastic belt 106 and/or the lateral centerline 126b of the second elastic belt 108 and/or the lateral centerline 126c of the chassis 102. The fastener components 707 may comprise a longitudinal centerline 124d oriented substantially parallel to the longitudinal centerline 124a of the first elastic belt 106 and/or the longitudinal centerline 124b of the second elastic belt 108 and/or the longitudinal centerline 124c of the chassis 102.

As shown in FIG. 8AA1, in some configurations, fastener components 707 may be positioned on and connected with the wearer facing surface 115b of the first elastic belt 106 and/or the second elastic belt 108 in a region where the first elastic belt 106 and/or second elastic belt 108 overlaps the chassis 102. In some configurations, the fastener component 707 may be sandwiched between the second substrate 164 of the first elastic belt 106 or the second elastic belt 108 and the backsheet 136 of the chassis 102. In some configurations, such as shown in FIG. 8AA1, the fastener component 707 comprises hooks 715 protruding from a base 717, and the hooks 715 extend from the first belt 106 toward the backsheet 136. The fastener component 707 may be configured as a separate discrete element that may be connected with the wearer facing surface 115b of the first belt 106 in various ways. For example, as shown in FIG. 7AA1, adhesive 716 may connect the base 717 of the fastener component 707 with wearer facing surface 115b of the first belt 106. It is to be appreciated that the fastener component 707 may be connected with the first belt 106 by mechanical bonding in addition to or instead of adhesive. It is to be appreciated that the base 717 may be configured in various ways. For example, the base 717 may comprise a thermoplastic film. In some configurations, the base 717 may comprise a laminate with various layers bonded together, such as disclosed for example in US. Patent Publication No. 2021/0045931 A1. For example, the base 717 may comprise a thermoplastic film layer bonded with a nonwoven layer. It is to be appreciated that such layers may be bonded together in various ways, such as with adhesive, mechanical bonding, and/or extrusion bonding. In some configurations, the fastener component 707 may be integrally formed from materials of the first belt 106, such as shown for example in FIG. 8AA2, or may be integrally formed from materials and attached with the first belt.

As shown for example in FIG. 6B, a portion of the chassis 102 may overlap the inner wearer facing surface 115b of the first belt 106 to define a chassis overlap region 850. As such, the chassis overlap region 850 may extend laterally between the first longitudinal edge 128 and the second longitudinal edge 130 of the chassis 102 and longitudinally between the first lateral edge 144 of the chassis 102 and the inner edge 107b of the first belt 106. To help prevent contact of the fastener component 707 with a wearer's skin while wearing the diaper pant 100P, the fastener components 707 may be positioned on and connected with the wearer facing surface 115b of the first elastic belt 106 and/or the wearer facing surface 117b of the second elastic belt 108 in the chassis overlap region 850 where the first elastic belt 106 and/or second elastic belt 108 overlaps the chassis 102. For example, the fastener component 707 may be sandwiched between the wearer facing surface 115b of the first belt 106 and the chassis 102. In some configurations, the fastener component 707 may be sandwiched between the second substrate 164 of the first elastic belt 106 or the second elastic belt 108 and the backsheet 136 of the chassis 102. In some configurations, the fastener component 707 may be positioned laterally between the first longitudinal side edge 128 and the second longitudinal side edge 130 of the chassis 102. The fastener component 707 may also be positioned longitudinally between the first lateral edge 144 of the chassis 102 and the inner edge 107b of the first belt 106. As shown in FIG. 7A, the fastener component 707 may be positioned adjacent the frangible pathway 700. The accessibility opening 802, which may be considered part of the frangible pathway 700, may be positioned adjacent the fastener component 707. As such, the frangible pathway 700 may partially surround the fastener component 707. In some configurations, such as shown in FIG. 9B, the frangible pathway 700 may extend through the fastener component 700, effectively dividing the fastener component 707 into a first fastener part 707' and a second fastener part 707". As discussed above, the first fastener part 707' is separated from the second fastener part 707" as the frangible pathway is torn. When completing the tearing operation, the first belt zone 831 and the second belt zone 832 will include first fastener parts 707', and the third belt zone 833 will include second fastener parts 707" separated from respective first fastener parts 707' during the tearing of frangible pathways 700.

In the configuration shown in FIGS. 6A and 8A, both the frangible pathway 700 and the accessibility opening 802 may extend through the fastener component, effectively dividing the fastener component 707 into a first fastener part 707' and a second fastener part 707". The accessibility openings 802 shown in FIG. 8A may comprise slits that are generally oriented in a longitudinal direction. In addition, the accessibility opening 802 extends through the fastener component 707 and may be positioned entirely within a perimeter of the fastener component. It is to be appreciated that such slits may be straight and/or curved. In some configurations, a longitudinally extending accessibility opening 802 may define a length dimension in the range of about 10 mm to about 30 mm, specifically reciting all 0.1 mm increments within the above-recited range and all ranges formed therein or thereby. In addition, in some configurations, a longitudinally extending accessibility opening 802 may also be curved to extend laterally in the range of about 2 mm to about 20 mm, specifically reciting all 0.1 mm increments within the above-recited range and all ranges formed therein or thereby.

Figure 10:
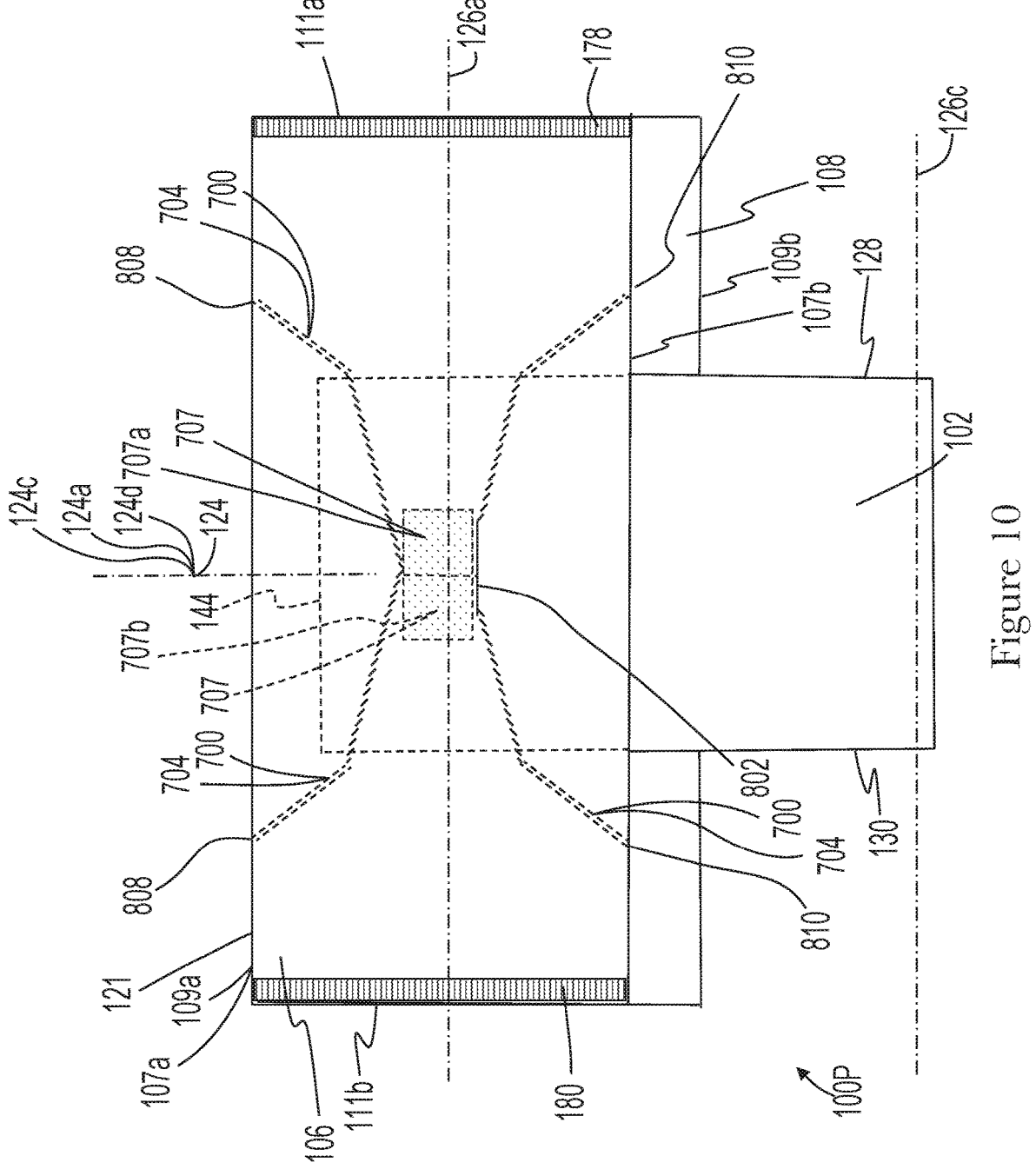
FIG. 10 shows a front plan view of a diaper pant with another configuration of frangible pathways.

In another configuration shown in FIG. 10, the diaper pant 100P may comprise one fastener component 707 joined to the wearer facing surface 115b of the first belt 106 in a location overlapping the longitudinal centerline 124c of the chassis 102. The longitudinal centerline 124d of the fastener component 707 may be coincident with, or in proximity of, the longitudinal centerline 124c of the chassis 102. The frangible pathway 700 may divide fastener component 707 into the first fastener component 707a and the second fastener component 707b of substantially similar size and geometry. An accessibility opening 802 may be disposed at, or in proximity of, a longitudinally inboard lateral edge of the fastener component 707. Longitudinally outboard the lateral edges of the fastener component 707, the frangible pathway 700 may extend in longitudinal and lateral directions to the waist edge 121 and inner edge 107b of the first belt 106. A caregiver or wearer may access and grasp the fastener component 707 through the accessibility opening 802 and subsequently separate the frangible pathway 700 into the first and second fastener components 707a, 707b.

Figure 11:
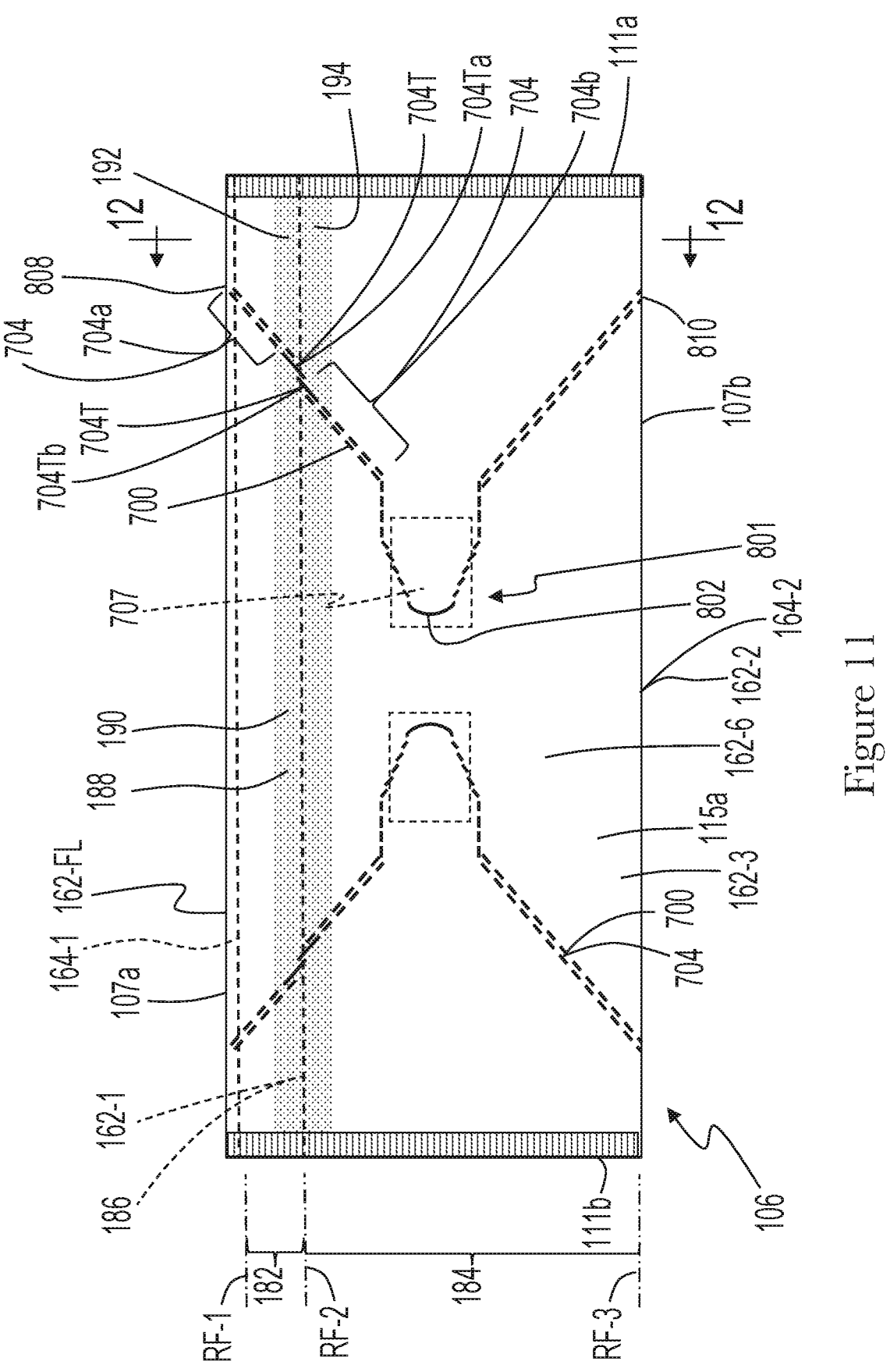
FIG. 11 shows a detailed front plan view of a first belt of a diaper pant.
Figures 12, 12A:
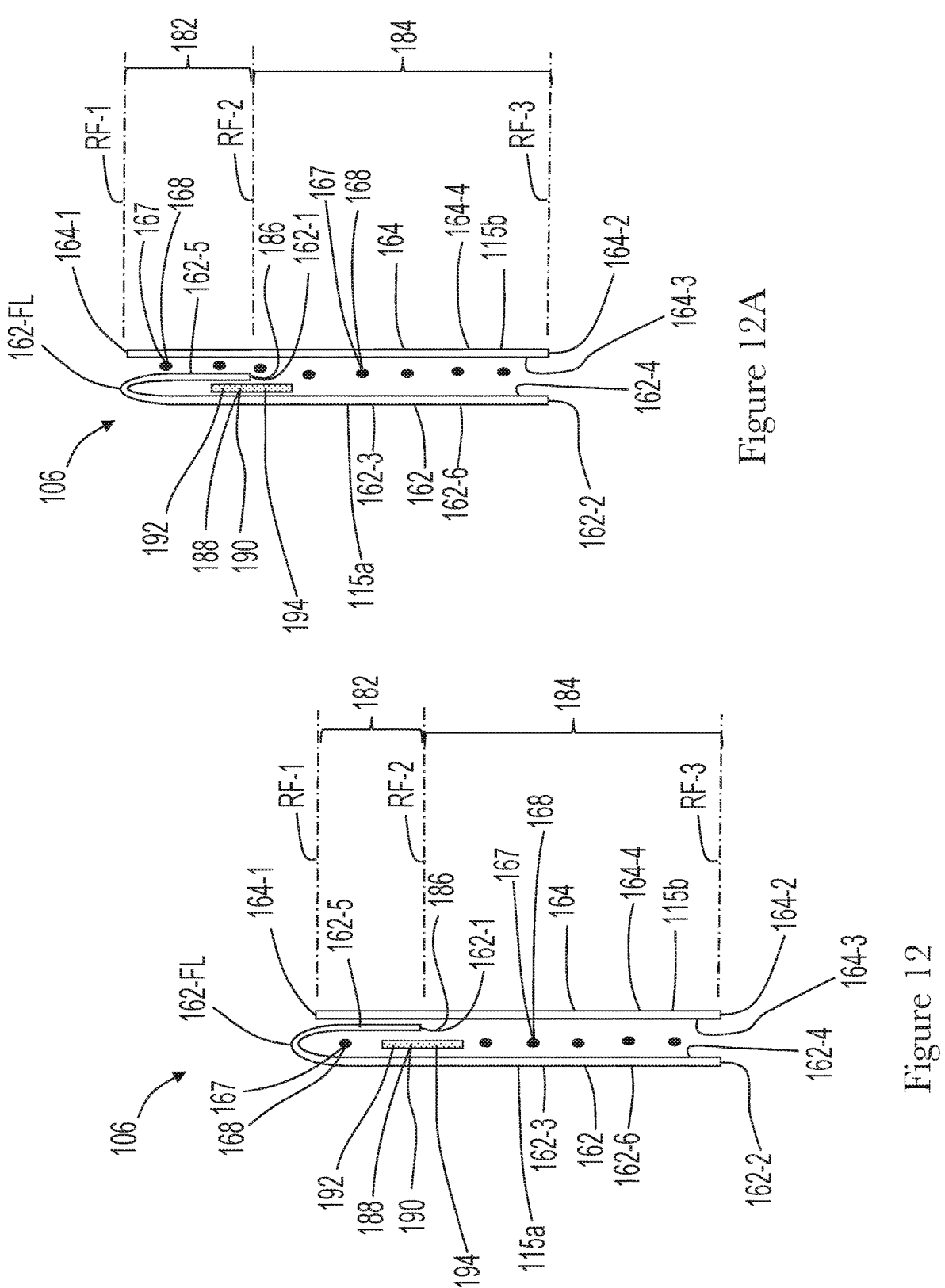
FIG. 12 is a cross-sectional view of a configuration of the first belt of FIG. 11 taken along line 12-12, wherein a first substrate comprises a folded portion sandwiched between the first substrate and a second substrate.
FIG. 12A is a cross-sectional view of another configuration of the first belt, wherein a first substrate comprises a folded portion sandwiched between the first substrate and a second substrate and wherein elastic strands are bonded between the folded portion and the second substrate.
Figure 13:
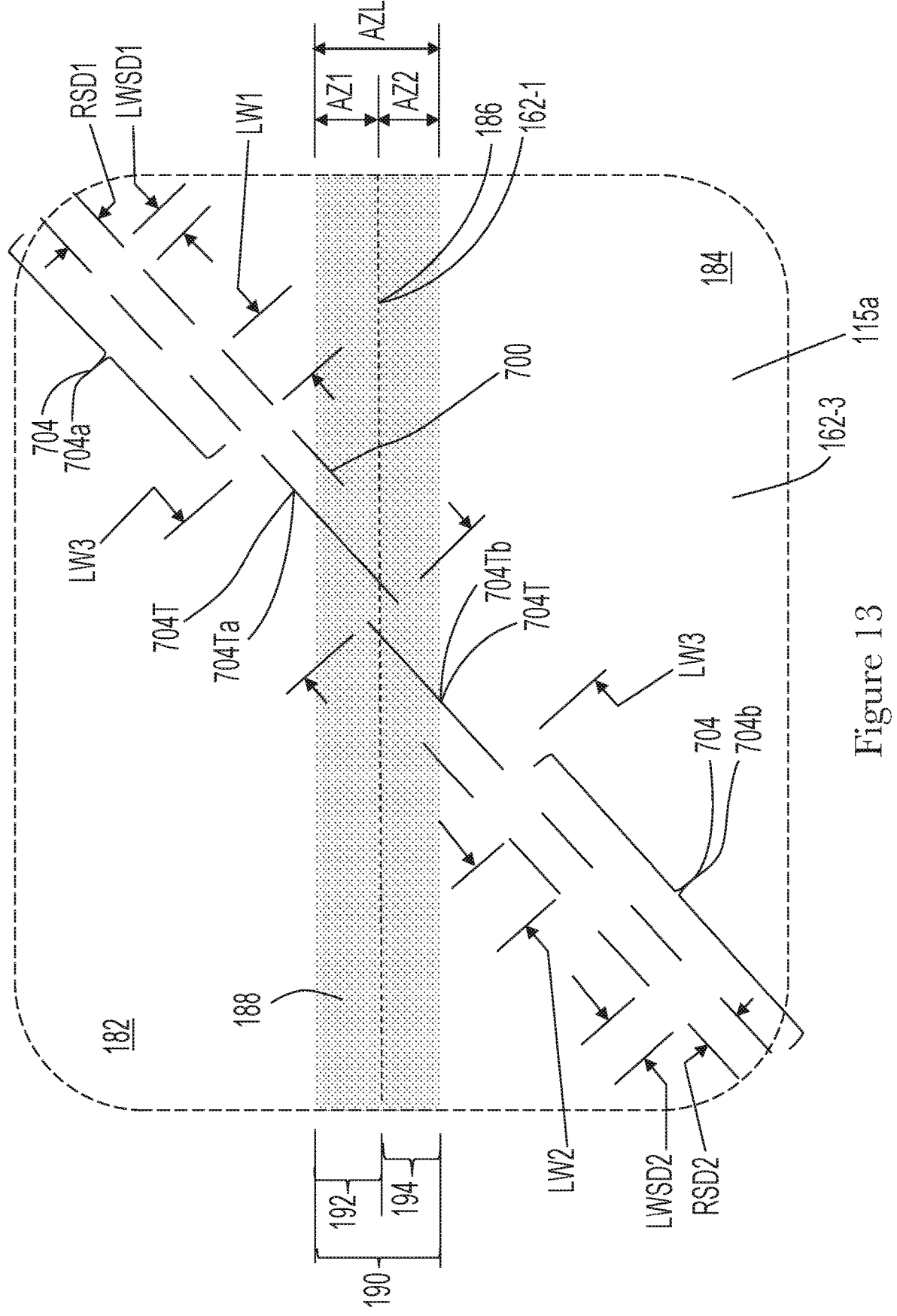
FIG. 13 is a detailed view of lines of weakness of a frangible pathway of the first belt of FIG. 11.

As discussed herein and as illustrated in the accompanying figures, it is to be appreciated that the first belt 106 and/or second belt 108 may be configured as laminates that may comprise regions having different numbers of layers of substrates. For example, such as discussed above with reference to FIGS. 3A, 3B, 3A1, and 3A2, at least one substrate of a first belt and/or a second belt may be folded to partially overlap itself and/or another substrate, which in turn may define regions of the belt having different numbers of layers of substrates. In other examples, one more discrete substrates may be connected with a particular region of a belt to define regions of the belt having different numbers of layers of substrates. As discussed in more detail below, a belt and/or frangible pathway may be configured in ways to help mitigate problems that may otherwise be associated with a tearing operation, wherein the tear propagates along a frangible pathway from a region of relatively fewer numbers of substrate layers, across an edge of a substrate layer, and into a region of relatively greater numbers of substrate layers. For example, FIGS. 11-13 show detailed views of a first belt 106 comprising a frangible pathway 700, such as discussed above with reference to diaper pant 100P in FIGS. 6A-6F. The example constructions shown in FIGS. 11-13 of the first belt 106 and frangible pathway 700 may help ensure that a tear will propagate along lines of weakness 704 of a frangible pathway 700 without unintentionally propagating in undesired directions along the first belt 106 as the tear propagates across the first belt 106 and into regions of increased numbers of layers of substrates. Although FIGS. 11-13 show configurations of the first belt 106, it is to be appreciated that such configurations may be applied with the second belt 108.

As shown in FIGS. 11 and 12, the first belt 106 comprises an outer garment facing surface 115*a* and an inner wearer facing surface 115*b*. The first belt 106 further comprises a laterally extending outer edge 107*a* and a laterally extending inner edge 107*b*, wherein the outer edge 107*a* is positioned longitudinally outward of the inner edge 107*b*. The first belt 106 may further comprise a first region 182 and a second region 184, wherein the first region 182 comprises a first number of layers of substrates and the second region 184 comprises a second number of layers of substrates, wherein the first number of layers substrates is greater than second number of layers of substrates.

For example, as shown in FIG. 12, the first belt 106 may comprise a first substrate 162 and a second substrate 164, such as discussed above with reference to various figures. As shown in FIGS. 11 and 12, the first substrate 162 comprises a laterally extending first edge 162-1, a laterally extending second edge 162-2, a first surface 162-3, and an opposing second surface 162-4. The first substrate 162 may also be folded along a fold line 162-FL such that a first portion 162-5 of the first substrate 162, which may also be referred to as a folded portion, is positioned in a facing relationship with a second portion 162-6 of the first substrate 162. As such, the first portion 162-5 extends longitudinally between the fold line 162-FL and the first edge 162-1 of the first substrate 162, and the second portion extends longitudinally between the fold line 162-FL and the second edge 162-2 of the first substrate 162.

With continued reference to FIGS. 11 and 12, the second substrate 164 comprises a laterally extending first edge 164-1, a laterally extending second edge 164-2, a first surface 164-3, and an opposing second surface 164-4. The second surface 162-4 of the first substrate 162 may be oriented in a facing relationship with the first surface 164-3 of the second substrate 164. In addition, the first portion 162-5 of the first substrate 162 may be positioned or sandwiched between the second surface 162-4 of the first substrate 162 and the first surface 164-3 of the second substrate 164. It is to be appreciated that the first portion 162-5 and the second portion 162-6 of the second substrate 162 as well as the first substrate 162 and the second substrate 164 may be bonded together in various ways, such as with adhesive and/or mechanical bonding as discussed above. In the configuration shown in FIG. 12, the first surface 162-3 of the first substrate 162 in the second portion 162-6 may at least partially define the outer garment facing surface 115*a* of the first belt 106. In addition, the second surface 164-4 of the second substrate 164 may at least partially define the inner wearer facing surface 115*b* of the first belt 106. Further, a part of the first portion 162-5 of the second belt 162 that remains uncovered by the second substrate 164 may also at least partially define the inner wearer facing surface 115*b* of the first belt 106.

For illustration purposes, FIGS. 11 and 12 include reference lines RF-1, RF-2, and RF-3 generically representing example locations of edges of the first region 182 and the second region 184, wherein the first region 182 may extend longitudinally between RF-1 and RF-2, and wherein the second region 184 may extend longitudinally between RF-2 and RF-3. The first edge 162-1 of the first substrate 162 may coincide with the reference line RF-2, and as such, may define a border 184 between the first region 182 of first belt 106 and the second region 184 of the first belt 106. In addition, the first edge 164-1 of the second substrate 164 may coincide with the reference line RF-1, and as such, the first region 182 of the first belt 106 may extend longitudinally from the first edge 164-1 of the second substrate 164 to the first edge 162-1 of the first substrate 162. Further, the second edge 162-2 of the first substrate 162 and the second edge 164-2 of the second substrate 164 may be coterminous and define the inner edge 107*b* of the first belt 106 and may coincide with reference line RF-3, and as such, the second region 184 of the first belt 106 may extend longitudinally from the first edge 162-1 of the first substrate 162 to the inner edge 107*b* of the first belt 106.

It is to be appreciated that the first substrate 162 and the second substrate 164 shown in FIG. 12 may include different arrangements, configurations, and/or relative positions so as to define various different locations of borders of the first region 182 and the second region 184 in the first belt 106. For example, in some configurations, the first edge 164-1 of the second substrate 164 may be coterminous with the fold line 162-FL of the first substrate 162, and as such, the first region 182 of the first belt 106 may extend longitudinally from the first edge 164-1 of the second substrate 164 and the fold line 162-FL to the first edge 162-1 of the first substrate 162. In yet other configurations, the first edge 164-1 of the second substrate 164 may extend longitudinally outboard of the fold line 162-FL of the first substrate 162, and as such, the first region 182 of the first belt 106 may extend longitudinally from the fold line 162-FL to the first edge 162-1 of the first substrate 162. In some configurations, the fold line 162-FL may define the outer edge 107*a* of the first belt 106, and as such, the first region 182 of the first belt 106 may extend longitudinally from the outer edge 107*a* of the first belt 106 to the first edge 162-1 of the first substrate 162. In some configurations, the second edge 162-2 of the first substrate 162 and the second edge 164-2 of the second substrate 164 may not be coterminous, and as such, the second region 184 of the first belt 106 may extend longitudinally from the first edge 162-1 of the first substrate 162 to either the second edge 162-2 of the first substrate 162 or the second edge 164-2 of the second substrate 164.

As previously mentioned, the first region 182 of the first belt 106 comprises more layers of substrates than the second region 184 of the first belt 106. In some configurations, the first region 182 of the first belt 106 may comprise at least 3 layers of substrates and the second region 184 of the first belt 106 may comprise at least 2 layers of substrates. For example, as shown in FIG. 12, the first region 182 of the first belt 106 may comprise 3 layers of substrates, for example: the first portion 162-5 of the first substrate 162, the second portion 162-6 of the first substrate 162, and the second substrate 164. And the second region 184 of the first belt 106 may comprise 2 layers of substrates: namely, the second portion 162-6 of the first substrate 162 and the second substrate 164.

As discussed above, it is to be appreciated that the first belt 106 and/or the second belt 108 may also comprise elastic material 167 sandwiched between and bonded between at least two layers of substrates. For example, as shown in FIG. 12, the first belt 106 may include elastic material 167 configured as individual elastic strands 168 bonded between the first substrate 162 and the second substrate 164. For example, the first region 182 of the first belt 106 and/or the second region 184 of the first belt 106 may include elastic strands 168. As shown in FIG. 12, elastic strands 168 may be bonded between the first portion 162-5 of the first substrate 162 and the second portion 162-6 of the first substrate 162 as well as between the second surface 162-4 of the first substrate 162 and the first surface 164-3 of the second substrate 164. As shown in FIG. 12A, elastic strands 168 may be bonded between the first portion 162-5 of the first substrate 162 and the first surface 164-3 of the second substrate 164 as well as between the second surface 162-4 of the first substrate 162 and the first surface 164-3 of the second substrate 164. It is to be appreciated that in some configurations, elastic strands 168 may be bonded between the first portion 162-5 of the first substrate 162 and the second portion 162-6 of the first substrate 162 as in FIG. 12 in addition to elastic strands 168 being bonded between the first portion 162-5 of the first substrate 162 and the first surface 164-3 of the second substrate 164 as in FIG. 12A.

As discussed above, frangible pathways 700 may be configured such that during the tearing process, the tear propagates in a desire direction along the frangible pathway 700 across the first belt 106 and/or second belt 108. For example, in the configurations discussed above with reference to FIGS. 6A-6F, the first belt 106 may be configured such that a tear is intended to be initiated by a user at a grip region 801 and/or an accessibility opening 802 in the first belt 106. The user may exert a pulling force Fp on the first grip region 801a of the first belt 106 outward away from the wearer to continue tearing the first belt 106 along the frangible pathway 700 such that tear lines 705 may propagate in directions toward the distal terminus 808 and the proximal terminus 810. It is to be appreciated that the application of such a desired tear propagation to the first belt configuration shown in FIGS. 11-13 may require tear lines to propagate from a grip region 801 and/or an accessibility opening 802 across the second region 184, across the first edge 162-1 of the second substrate 162, and then into and across the second region 184 toward the distal terminus 808. As previously mentioned, the first belt 106 and/or frangible pathway may be configured with various aspects to help increase the probability of a consistent and continuous propagation of a tear line 705 along the frangible pathway 700 from the second region 184 to the first region 182.

As shown in FIGS. 11 and 13, the frangible pathways 700 comprise individual lines of weakness 704. In particular, the frangible pathways may comprise first lines of weakness 704a positioned in the first region 182, second lines of weakness 704b positioned in the second region 184, and at least one transition line of weakness 704T extending through the border 186 between the first region 182 and the second region 184 and partially through the first region 182 and the second region 184. As discussed above, the border 186 may be defined by the first edge 162-1 of the first substrate 162, and as such, the at least one transition line of weakness 704T may extend across and the first edge 162-1 of the first substrate 162. As discussed above, the lines of weakness 704 herein may comprise discrete cut lines. As such, the at least one transition line of weakness 704T may cut the first edge 162-1 of the first substrate 162. In some configurations, the first lines of weakness 704a comprise discrete cut lines that penetrate through some or all the layers of the first region 182; the second lines of weakness 704b comprise discrete cut lines that penetrate through some or all the layers of the second region 184; and the at least one transition line of weakness 704T comprises a discrete cut line that penetrates through some or all the layers of the first region 182 and the second region 184. In some configurations, the at least one transition line of weakness 704T may be configured as a bond that fuses materials of substrates together at the first edge 162-1 of the first substrate 162.

It is to be appreciated that lines of weakness 704 of the frangible pathway 700 may be configured in various ways to help ensure that at least one transition line of weakness 704T extends across the border 186, such as the first edge 162-1 of the first substrate 162, taking into account a full range of potential manufacturing overlap tolerances. For example, it is to be appreciated that various numbers of transition lines of weakness 704T may be used. As shown in FIGS. 11 and 13 for example, the frangible pathway 700 may include a first transition line of weakness 704Ta and a second transition line of weakness 704Tb. In another example, the transition lines of weakness 704T may be relatively longer than other lines of weakness. For example, as shown in FIG. 13, the first lines of weakness 704a may extend for first lengths LW1, the second lines of weakness 704b may extend for second lengths LW2, and the transition lines of weakness 704T may extend for a third length LW3. As such, the third length LW3 may be greater than the first lengths LW1 and the second lengths LW2. In some configurations, the transition lines of weakness 704T may extend for a length LW3 from about 4 mm to about 15 mm, specifically reciting all 0.01 mm increments within the above-recited range and all ranges formed therein or thereby. In some configurations, the first lines of weakness 704a may extend for a length LW1 and/or the second lines of weakness 704b may extend for a length LW2 from about 1 mm to about 5 mm, specifically reciting all 0.01 mm increments within the above-recited range and all ranges formed therein or thereby. It is also to be appreciated that the first lengths LW1 may be equal to or different from the second lengths LW2. In some configurations, the transition lines of weakness 704T may extend from the border 186, such as the first edge 162-1 of the first substrate 162, and into the first region 182 and/or the second region 184 for a distance of at least about 10 mm. In some configurations, the transition lines of weakness 704T may comprise different features or aspect than those of the first lines of weakness 704a and/or the second lines of weakness 704b. For example, the transition lines of weakness 704T may comprise different lengths, shapes, and/or widths than the first lines of weakness 704a and/or the second lines of weakness 704b. In some configurations, the transition lines of weakness 704T may be linear and the first lines of weakness 704a and/or the second lines of weakness 704b may be non-linear. In some configurations, the transition lines of weakness 704T may be non-linear and the first lines of weakness 704a and/or the second lines of weakness 704b may be linear. In some configurations, the transition lines of weakness 704T may be in the form of pressure bonds whereas the first lines of weakness 704a and/or the second lines of weakness 704b may be in the form of cut lines. In some configurations, the transition lines of weakness 704T may be in the form of cut lines whereas the first lines of weakness 704a and/or the second lines of weakness 704b may be in the form of pressure bonds.

It is to be appreciated that having a line of weakness 704 extending across the border 186, such as the first edge 162-1 of the first substrate 162, may help ensure a continuous transition of the propagation of a tear line along a frangible pathway 700 and across an edge of a substrate when propagating from the second region 184 to the first region 182. Without a transition line of weakness 704T extending across an edge of a substrate, a force required to maintain a tear propagation from the second region 184 to the first region 182 may have to increase substantially in order to continue tearing through an unweakened substrate edge. In turn, a tear may unintentionally propagate in a direction away from the frangible pathway 700.

It is also to be appreciated the first lines of weakness 704a and the second lines of weakness 704b may be configured in various ways to help maintain a relatively constant force required to continue a tear propagation along the frangible pathway 700 through the first region 182 and the second region 184. For example, as shown in FIG. 13, the first lines of weakness 704a may be separated from each other by a first separation distance LWSD1 and the second lines of weakness 704b may be separated from each other by a second separation distance LWSD2. Because the first region 182 comprises more layers of substrates than the second region 184, a force required to maintain a tear propagation through the layers of substrates in first region 182 may be higher than a force required to maintain a tear propagation through the layers of substrates of the second region 182. As such, in some configurations, the first separation distance LWSD1 may be less than the second separation distance LWSD2 to help reduce differences between forces required to maintain a tear propagation through the first region 182 and the second region 184. In some configurations, the first separation distance LWSD1 and/or the second separation distance LWSD2 may be greater than 0 mm and less than about 3 mm, specifically reciting all 0.01 mm increments within the above-recited range and all ranges formed therein or thereby. It is also to be appreciated that the first lines of weakness 704a and/or the second lines of weakness 704b may be arranged in rows, such as shown in FIG. 13. As such, it is to be appreciated that the rows of first lines of weakness 704a may be separated from each other by a first row separation distance RSD1 and the rows of second lines of weakness 704b may be separated from each other by a second row separation distance RSD2. In some configurations, the first row separation distance RSD1 may be equal to or different from the second row separation distance RSD2. In some configurations, the first row separation distance RSD1 and/or the second row separation distance RSD2 may be from about 0.5 mm to about 3 mm, specifically reciting all 0.01 mm increments within the above-recited range and all ranges formed therein or thereby.

In addition to the aforementioned aspects of frangible pathway 700 and lines of weakness 704 configurations, the first belt 106 and/or second belt 108 may also include structural features that may help to ensure a relatively smooth transition of a tear propagating through a belt laminate from the second region 184 of relatively fewer numbers substrate layers, across an edge of a substrate, such as the first edge 162-1 of the first substrate 162, through a first region 182 of relatively greater numbers of substrate layers. For example, as shown in FIGS. 11-13, the first belt 106 may comprise adhesive 188 applied so as to define a zone of adhesive 190 positioned between the first portion 162-5 of the first substrate 162 and the second portion 162-6 of the first substrate 162. As such, the first edge 162-1 of the first substrate 162 extends laterally through the zone of adhesive 190, which in turn bonds the first edge 162-1 with the second portion 162-6 of the first substrate 162. As shown in FIG. 13, the zone of adhesive 190 may extend for a length AZL in the longitudinal direction to help ensure that the first edge 162-1 consistently bonded with the second portion 162-6 of the first substrate 162 when taking into account manufacturing process tolerances. In some configurations, the length AZL of the zone of adhesive 190 may extend from about 5 mm to about 15 mm, specifically reciting all 0.01 mm increments within the above-recited range and all ranges formed therein or thereby.

With continued reference to FIGS. 11-13, the first edge 162-1 of the first substrate 162 may extend laterally through the zone of adhesive 190 to define a first adhesion zone 192 and a second adhesion zone 194. The first adhesion zone 192 may extend longitudinally from the first edge 162-1 of the first substrate 162 toward the fold line 162-FL for a distance AZ1. The second adhesion zone 194 may extend longitudinally from the first edge 162-1 of the first substrate 162 away from the fold line 162-FL and toward the second edge 162-2 for a distance AZ2. In some configurations, the distance AZ1 may be equal to or different from the distance AZ2. In some configurations, the distance AZ1 and/or the distance AZ2 may be from about 5 mm to about 10 mm, specifically reciting all 0.01 mm increments within the above-recited range and all ranges formed therein or thereby.

As shown in FIGS. 11-13, the frangible pathway 700 extends across the zone of adhesive 190, and at least one transition line of weakness 704T extends at least partially across the zone of adhesive 190. Having the first edge 162-1 of the first substrate 162 bonded with the second portion 162-6 of the second substrate 162 in a region where the frangible pathway crosses the first edge 162-1 between the first region 182 and the second region 184 may help promote a relatively smooth transition of a tear propagation from the second region 184 to the first region 182. More particularly, the zone of adhesive 190 may help prevent the first edge 162-1 and first portion 162-5 from unintentionally separating from the second portion 162-6 of the first substrate 162, which may interrupt the intended tear propagation along the frangible pathway 700. It is to be appreciated that the zone of adhesive 190 may extend for different distances in lateral directions across the first belt 106. For example, the zone of adhesive 190 may extend from the first edge 111a to the second 111a of the first belt 106. In some configurations, the zone of adhesive 190 may extend laterally in relatively shorter distances across the frangible pathway 700. In addition, adhesive 188 in the first adhesion zone 192 may bond the first portion 162-5 of the first substrate 162 with the second portion 162-6 of the first substrate 162. Further, adhesive 188 in the second adhesion zone 194 may bond the first surface 164-3 of the second substrate 164 with the second surface 162-4 of the first substrate 162 in the second portion 162-6. As such, the second substrate 164 is positioned so as to cover the second adhesion zone 194 and may help prevent unintended contact between a wearer and adhesive 188 in the second adhesion zone 194.

Figures 12B, 12C:
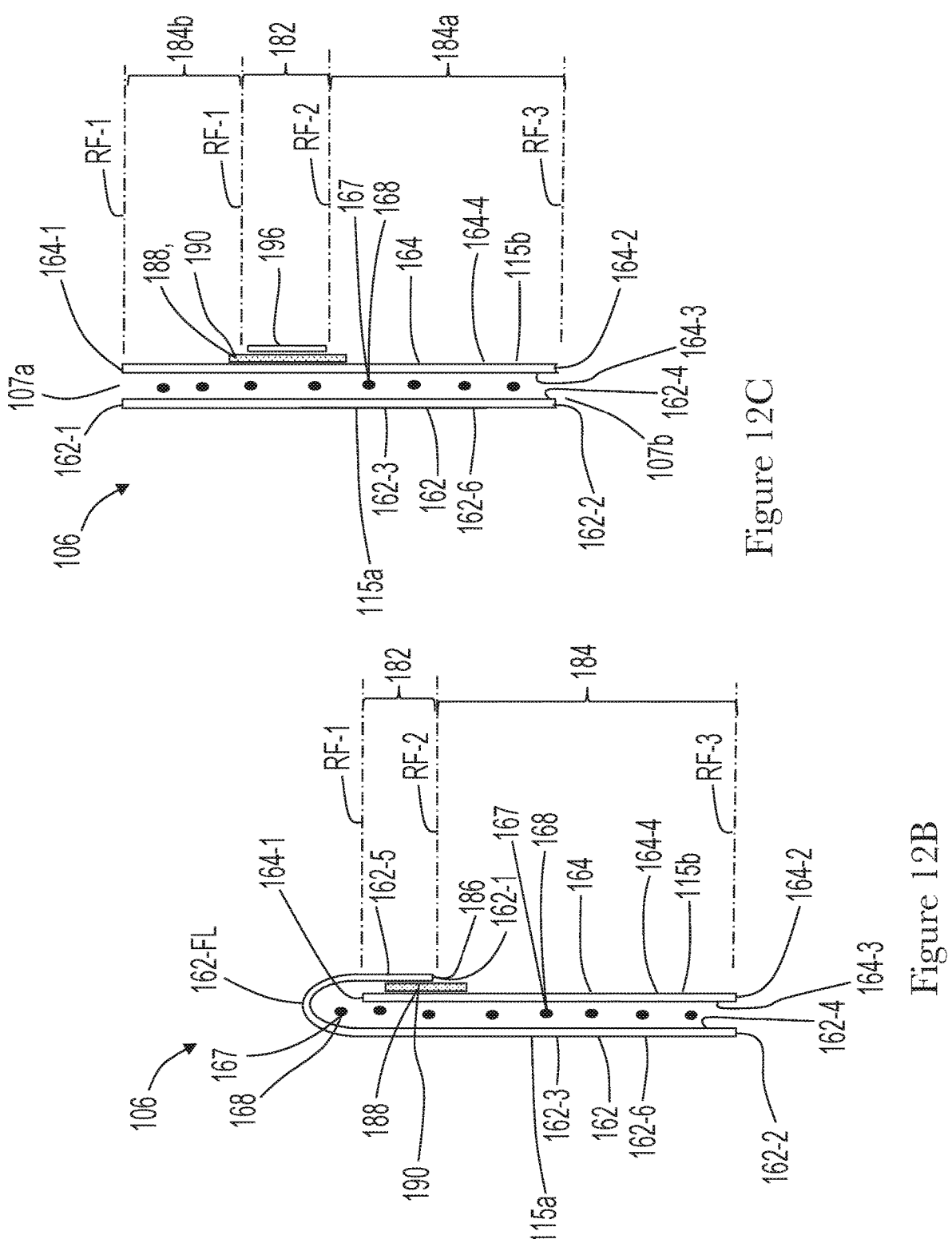
FIG. 12B is a cross-sectional view of another configuration of the first belt, wherein a first substrate comprises a folded portion configured such that the second substrate is sandwiched between the folded portion and the first substrate.
FIG. 12C is a cross-sectional view of another configuration of the first belt comprising first and second substrates, wherein a third substrate is bonded to the second substrate.

Although the above description is provided in the context of the belt configurations referenced in FIGS. 12 and 12A, it is to be appreciated that the first belt 106 may be constructed in various ways to define the first region 182 and the second region 184 of different numbers of layers of substrates. For example, as shown in FIG. 12B, the first belt 106 may be configured such that the first portion 162-5 of the first substrate 162 is positioned in a facing relationship with the second surface 164-4 of the second substrate 164. In addition, the zone of adhesive 190 is positioned between and the first portion 162-5 of the first substrate 162 and the second surface 164-4 of the second substrate 164, such that the first edge 162-1 of the first substrate 162 is bonded with the second surface 164-4 of the second substrate 164. In the configuration shown in FIG. 12C, the zone of adhesive 190 may bond a discrete third substrate 196 with the second substrate 164. As such, the first belt 106 may comprise a first region 182 positioned longitudinally between two second regions 184. As illustrated, the first region 182 may comprise the third substrate 196 and portions of the first and second substrates 162, 164. In addition, the first belt 106 may comprise a first second region 184a extending longitudinally from the inner edge 107b to the third substrate 196, and a second second region 184b extending longitudinally from the outer edge 107a to the third substrate 196. It is to be appreciated that the first belt 106 and/or the second belt 108 may comprise one or more first regions 182 and one or more second regions 184.

It is to be appreciated that the absorbent articles herein may be assembled in various ways utilizing various types of apparatuses configured to carry out various transformations in various orders of assembly. For example, FIGS. 14A-14E illustrate schematic representations of assembly transformations that may be utilized to assemble diaper pants 100P with belt and frangible pathway configurations described herein.

Figure 14A:
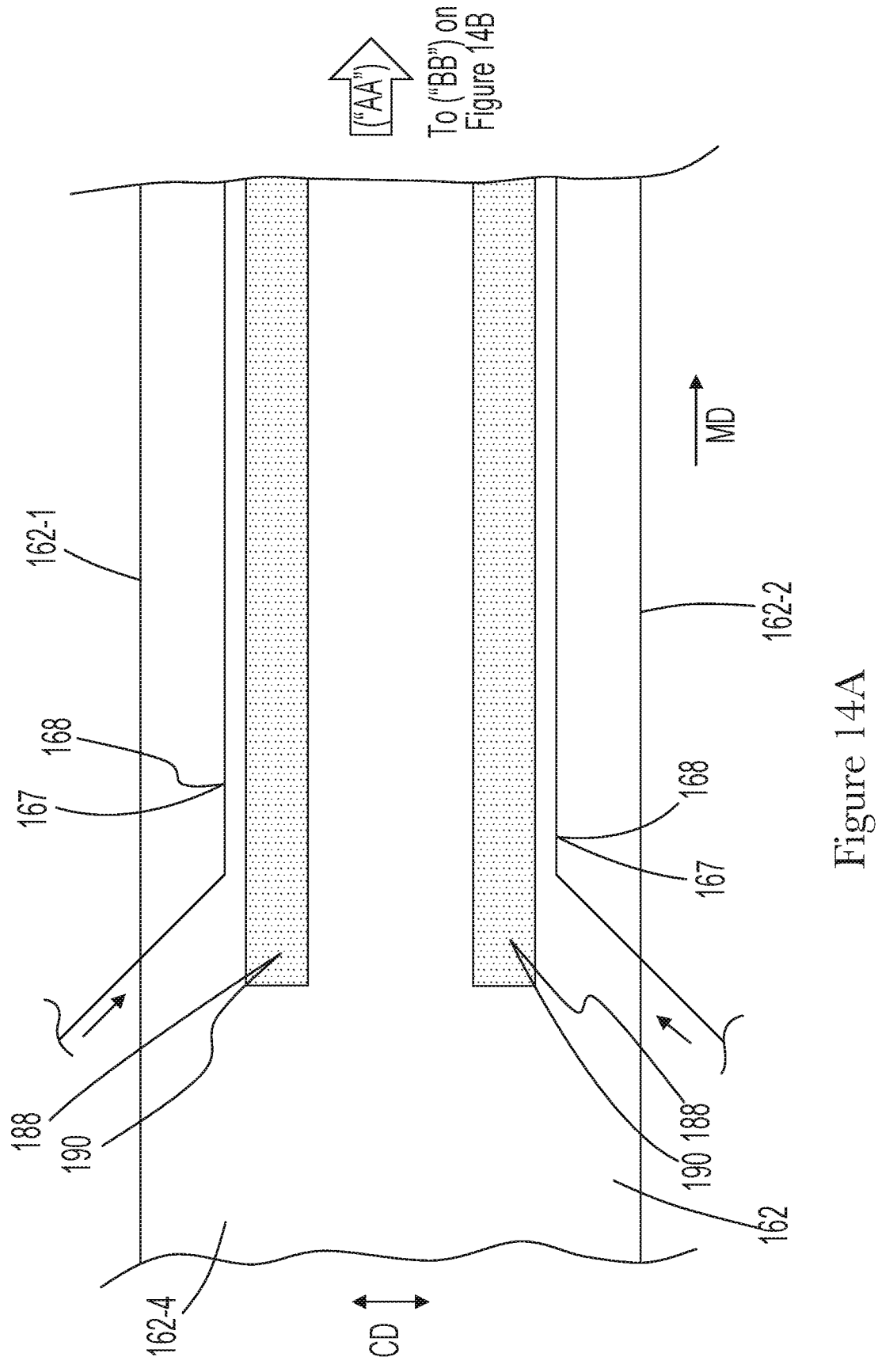
FIGS. 14A-14E illustrate schematic representations of assembly transformations that may be utilized to assemble diaper pants 100P.
Figure 14B:
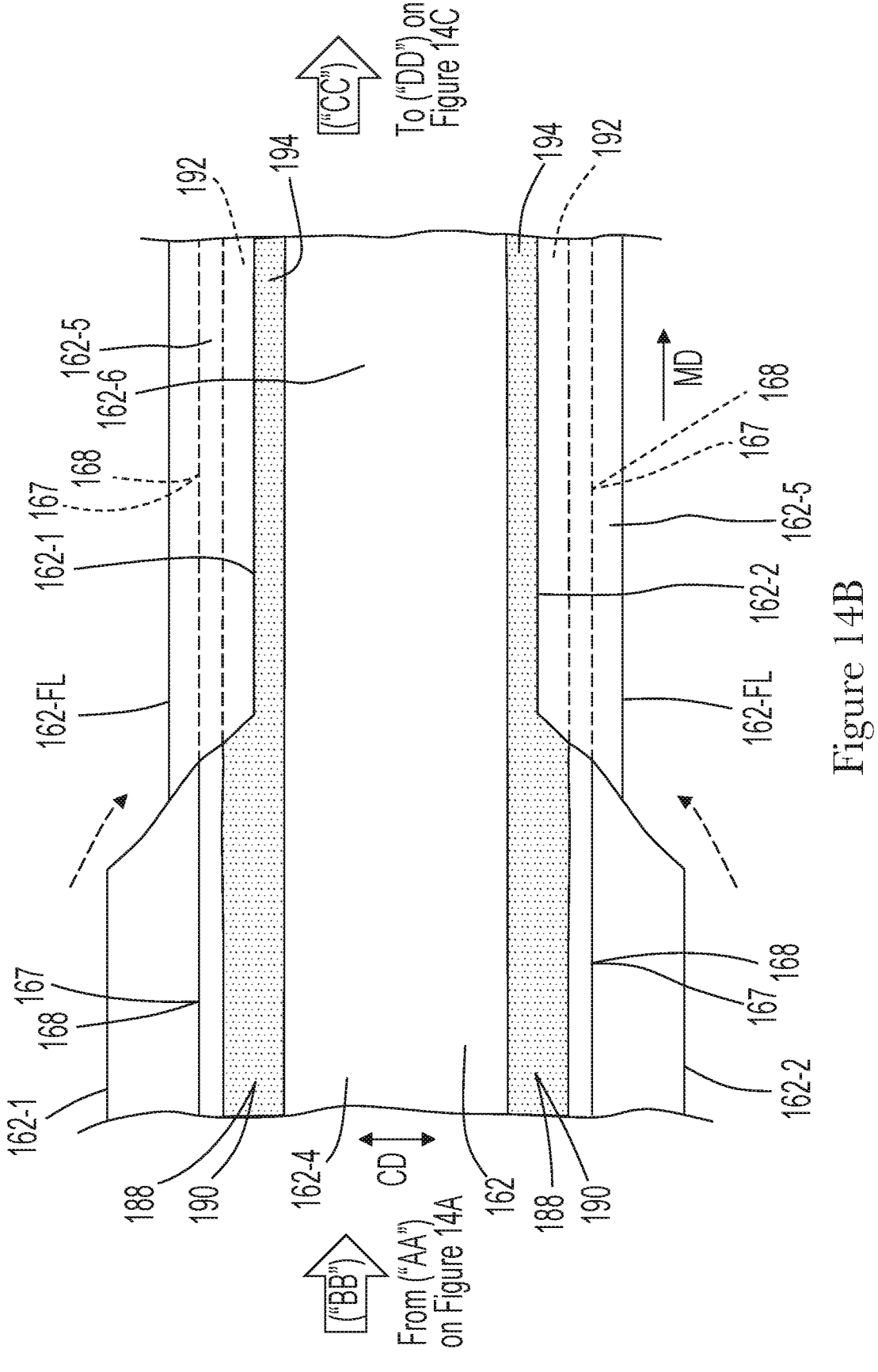

As shown in FIGS. 14A and 14B, when assembling diaper pants 100P, a first substrate 162 may be advanced in a machine direction MD. The first substrate 162 may comprise a first edge 162-1 and a second edge 162-2 separated from the first edge in a cross direction CD. The first substrate 162 may further comprise a first surface 162-3 and an opposing second surface 162-4. At least one elastic strand 168 may be bonded with second surface 162-4 of the first substrate 162. Adhesive 188 may also be applied to the second surface 162-4 of the first substrate 162 to define zones of adhesive 190 extending in the machine direction MD. With continued reference to FIG. 14B, the first substrate 162 may be folded along fold lines 162-FL such that first portions 162-5 of the first substrate 162 are placed in a facing relationship with a second portion 162-6 of the first substrate 162. The first edge 162-1 and the second edge 162-2 of the first substrate 162 may extend in the machine direction MD through the zones of adhesive 190 to define first adhesion zones 192 and second adhesion zones 194. The first edge 162-1 and the second edge 162-2 of the first substrate 162 and the first portions 162-5 of the first substrate 162 are bonded with the second portion 162-6 of the first substrate 162. The second adhesion zones extend in the cross direction CD between the first edge 162-1 and the second edge 162-2 of the first substrate 162.

Figure 14C:
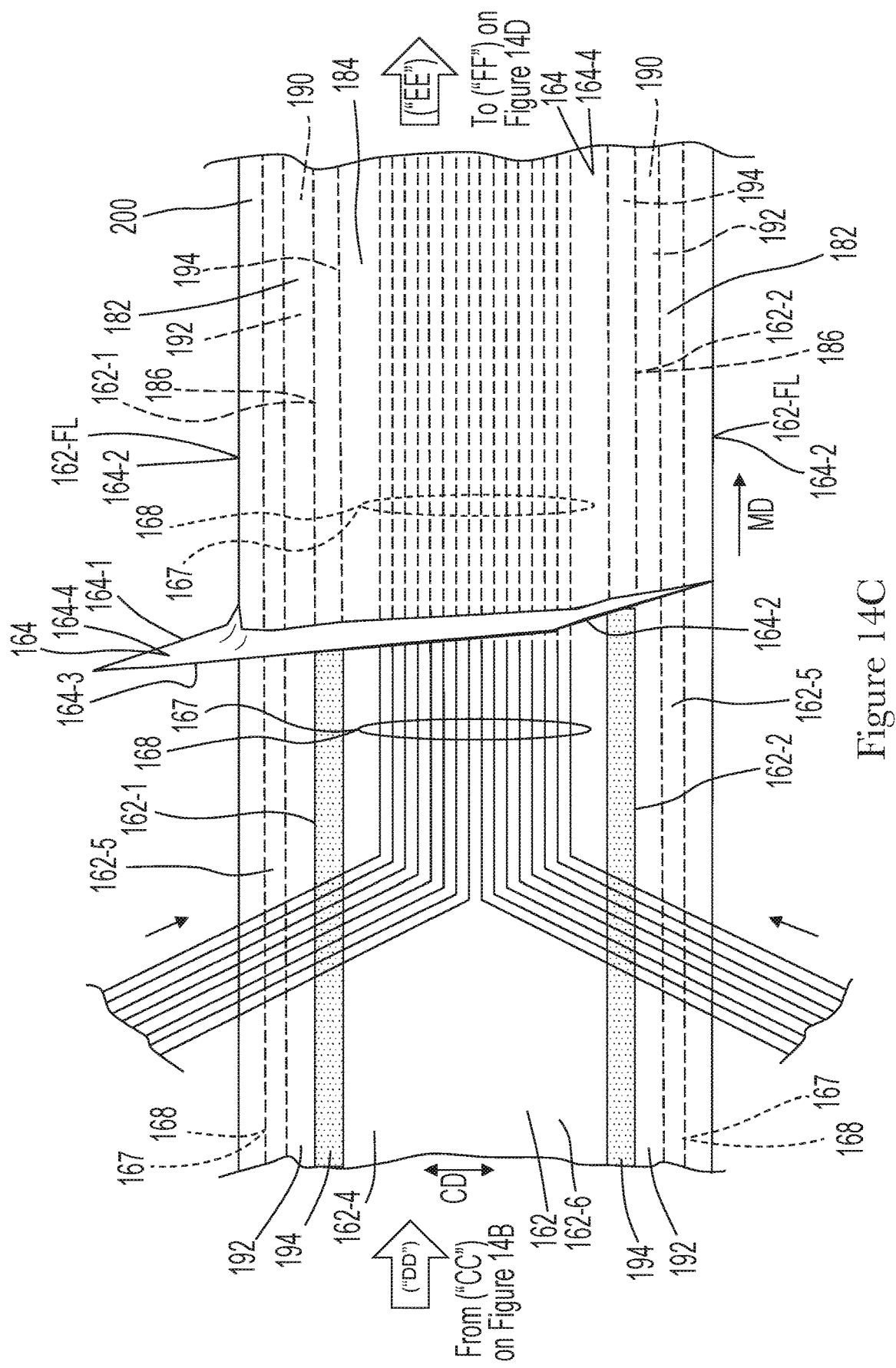

Referring now to FIG. 14C, a second substrate 164 may be provided that comprises a first edge 164-1 and a second edge 164-2 separated from the first edge 164-1 in the cross direction CD. The second substrate 164 may further comprise a first surface 164-3 and an opposing second surface 164-4. A plurality of stretched elastic strands 168 may be positioned and bonded between the first substrate 162 and the second substrate 164. With continued reference to FIG. 14C, an elastic laminate 200 may be formed by bonding the first substrate 162 together with the second substrate 164, wherein first portions 162-5 of the first substrate 162 are positioned between the second surface 162-4 of the first substrate 162 and the first surface 164-3 of the second substrate 164. The second adhesion zones 194 may bond the second surface 162-4 of the first substrate 162 with the first surface 164-3 of the second substrate 164. In turn, the elastic laminate 200 comprises a first region 182 comprising a first number of layers of substrates and a second region 184 comprising a second number of layers of substrates, wherein the first edge 162-1 and the second edge 162-2 of the first substrate 162 define borders 186 between the first regions 182 and the second region 184.

Figure 14D:
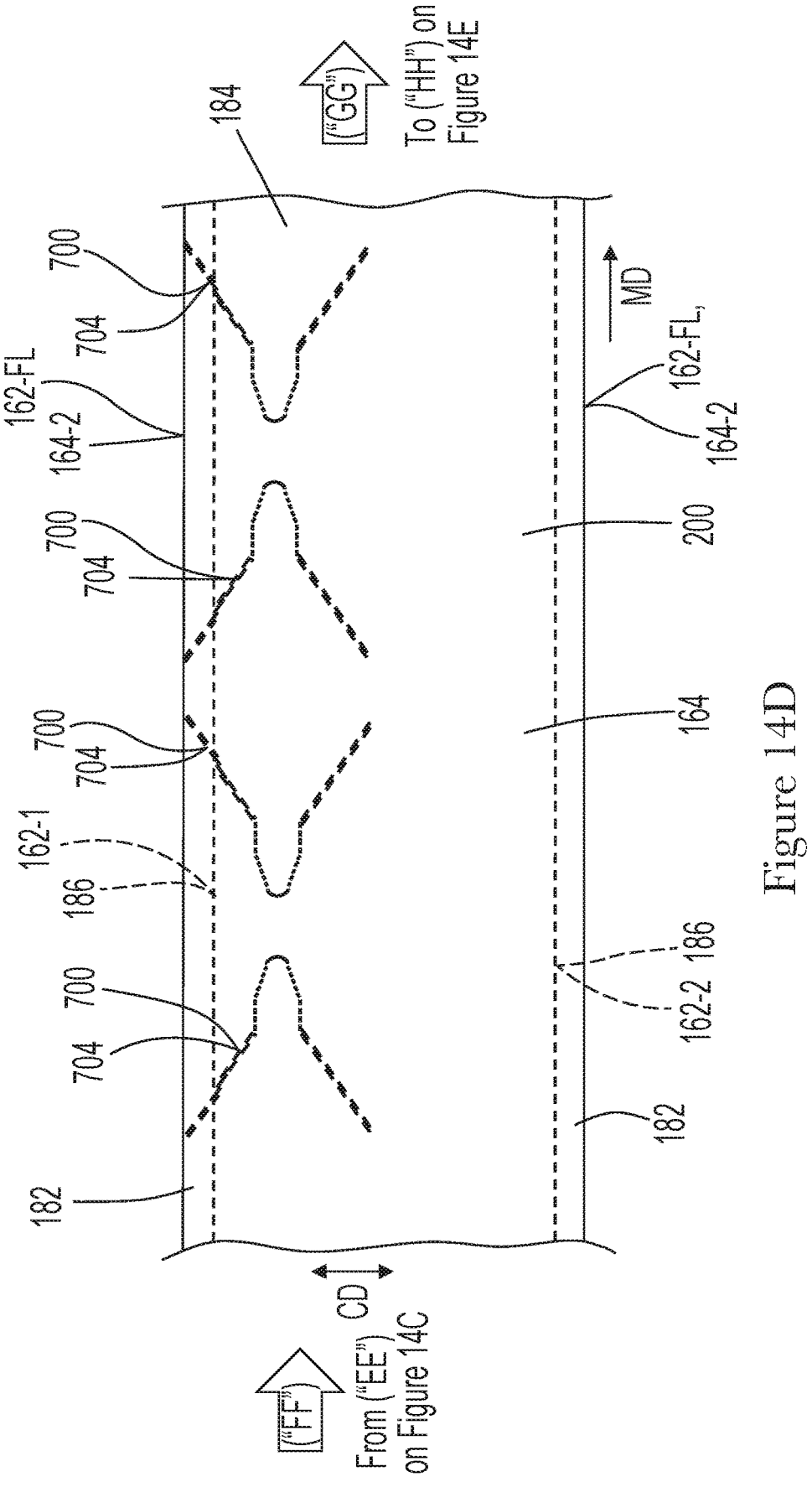

Referring now to FIG. 14D, frangible pathways 700 may be formed in the elastic laminate 200, wherein the frangible pathways 700 lines of weakness 704. In some examples, the frangible pathways 700 may be configured similar to the frangible pathways described above with reference to FIGS. 11-13, and may comprise first lines of weakness 704a in the first regions 182, second lines of weakness 704b in the second region 184, and at least one transition line of weakness 704T, wherein the at least one transition line of weakness 704T extends across the first edge 162-1 of the first substrate 162 and into both a first region 182 and the second region 186.

Figure 14E:
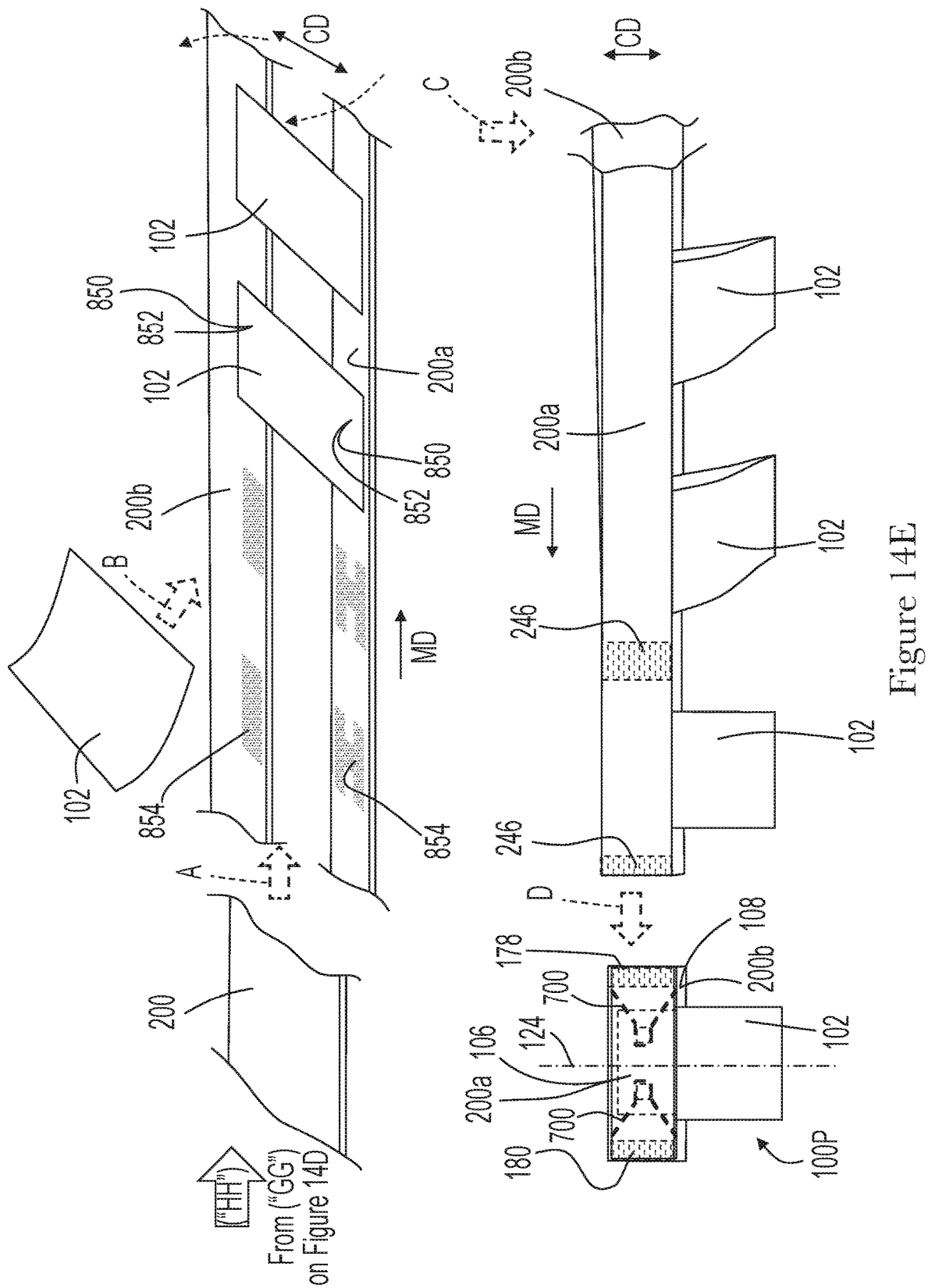

As shown in FIG. 14E, the elastic laminate 200 may be converted into a first elastic belt laminate 200a and/or a second elastic belt laminate 200b (represented by the dashed arrow "A"). The first elastic belt laminate 200a and the second elastic belt laminate 200b may be separated from each other in the cross direction CD. Adhesive 854 may be intermittently applied to first elastic belt laminate 200a and the second elastic belt laminate 200b. As shown in FIG. 8C, adhesive 854 may be applied in a pattern to define adherence regions 852. In turn, opposing end regions of chassis 102 may be permanently bonded with the adhesive 854 in overlap regions 850 on the first elastic belt laminate 200a and/or a second elastic belt laminate 200b (represented by the dashed arrow "B"). During subsequent assembly operations, the chassis 102 may be folded (represented by the dashed arrow "C") so as to position the first elastic belt laminate 200a into a facing relationship with the second elastic belt laminate 200b. Bonds 246 may be applied to the overlapping belt laminates 200a, 200b. Subsequently, discrete diaper pants 100P may be formed by separating the first and second belt laminates 200a, 200b into first and second belts 106, 108 by cutting along the cross direction CD through the first and second belt laminates 200a, 200b adjacent the bonds 246 (represented by the dashed arrow "D"). As such, the bonds 246 may be divided to define the first and second side seams 178, 180, respectively.

Average Decitex (Average-Dtex)

The Average Decitex Method is used to calculate the Average-Dtex on a length-weighted basis for elastic fibers present in an entire article, or in a specimen of interest extracted from an article. The decitex value is the mass in grams of a fiber present in 10,000 meters of that material in the relaxed state. The decitex value of elastic fibers or elastic laminates containing elastic fibers is often reported by manufacturers as part of a specification for an elastic fiber or an elastic laminate including elastic fibers. The Average-Dtex is to be calculated from these specifications if available. Alternatively, if these specified values are not known, the decitex value of an individual elastic fiber is measured by determining the cross-sectional area of a fiber in a relaxed state via a suitable microscopy technique such as scanning electron microscopy (SEM), determining the composition of the fiber via Fourier Transform Infrared (FT-IR) spectroscopy, and then using a literature value for density of the composition to calculate the mass in grams of the fiber present in 10,000 meters of the fiber. The manufacturer-provided or experimentally measured decitex values for the individual elastic fibers removed from an entire article, or specimen extracted from an article, are used in the expression below in which the length-weighted average of decitex value among elastic fibers present is determined.

The lengths of elastic fibers present in an article or specimen extracted from an article is calculated from overall dimensions of and the elastic fiber pre-strain ratio associated with components of the article with these or the specimen, respectively, if known. Alternatively, dimensions and/or elastic fiber pre-strain ratios are not known, an absorbent article or specimen extracted from an absorbent article is disassembled and all elastic fibers are removed. This disassembly can be done, for example, with gentle heating to soften adhesives, with a cryogenic spray (e.g., Quick-Freeze, Miller-Stephenson Company, Danbury, CT), or with an appropriate solvent that will remove adhesive but not swell, alter, or destroy elastic fibers. The length of each elastic fiber in its relaxed state is measured and recorded in millimeters (mm) to the nearest mm.

Calculation of Average-Dtex

For each of the individual elastic fibers $f_i$ of relaxed length $L_i$ and fiber decitex value $d_i$ (obtained either from the manufacturer's specifications or measured experimentally) present in an absorbent article, or specimen extracted from an absorbent article, the Average-Dtex for that absorbent article or specimen extracted from an absorbent article is defined as:

$$\text{Average}-Dtex = \frac{\sum_{i=1}^{n}(L_i \times d_i)}{\sum_{i=1}^{n}L_i}$$

where n is the total number of elastic fibers present in an absorbent article or specimen extracted from an absorbent article. The Average-Dtex is reported to the nearest integer value of decitex (grams per 10 000 m).

If the decitex value of any individual fiber is not known from specifications, it is experimentally determined as described below, and the resulting fiber decitex value(s) are used in the above equation to determine Average-Dtex.

Experimental Determination of Decitex Value for a Fiber

For each of the elastic fibers removed from an absorbent article or specimen extracted from an absorbent article according to the procedure described above, the length of each elastic fiber $L_k$ in its relaxed state is measured and recorded in millimeters (mm) to the nearest mm. Each elastic fiber is analyzed via FT-IR spectroscopy to determine its composition, and its density $\rho_k$ is determined from available literature values. Finally, each fiber is analyzed via SEM. The fiber is cut in three approximately equal locations perpendicularly along its length with a sharp blade to create a clean cross-section for SEM analysis. Three fiber segments with these cross sections exposed are mounted on an SEM sample holder in a relaxed state, sputter coated with gold, introduced into an SEM for analysis, and imaged at a resolution sufficient to clearly elucidate fiber cross sections. Fiber cross sections are oriented as perpendicular as possible to the detector to minimize any oblique distortion in the measured cross sections. Fiber cross sections may vary in shape, and some fibers may consist of a plurality of individual filaments. Regardless, the area of each of the three fiber cross sections is determined (for example, using diameters for round fibers, major and minor axes for elliptical fibers, and image analysis for more complicated shapes), and the average of the three areas $a_k$ for the elastic fiber, in units of micrometers squared ($\mu m^2$), is recorded to the nearest 0.1 $\mu m^2$. The decitex $d_k$ of the kth elastic fiber measured is calculated by:

$$d_k = 10\ 000\ m \times a_k \times \rho_k \times 10^{-6}$$

where $d_k$ is in units of grams (per calculated 10,000 meter length), $a_k$ is in units of $m^2$, and $\rho_k$ is in units of grams per cubic centimeter ($g/cm^3$). For any elastic fiber analyzed, the experimentally determined $L_k$ and $de_k$ values are subsequently used in the expression above for Average-Dtex.

Average-Strand-Spacing

Using a ruler calibrated against a certified NIST ruler and accurate to 0.5 mm, measure the distance between the two distal strands within a section to the nearest 0.5 mm, and then divide by the number of strands in that section−1

$$\text{Average-Strand-Spacing} = d/(n-1) \text{ where } n>1$$

report to the nearest 0.1 mm.

Average-Pre-Strain

The Average-Pre-Strain of a specimen are measured on a constant rate of extension tensile tester (a suitable instrument is the MTS Insight using Testworks 4.0 Software, as available from MTS Systems Corp., Eden Prairie, MN) using a load cell for which the forces measured are within 1% to 90% of the limit of the cell. Articles are conditioned at 23° C.±2 C° and 50%±2% relative humidity for 2 hours prior to analysis and then tested under the same environmental conditions.

Program the tensile tester to perform an elongation to break after an initial gage length adjustment. First raise the cross head at 10 mm/min up to a force of 0.05N. Set the current gage to the adjusted gage length. Raise the crosshead at a rate of 100 mm/min until the specimen breaks (force drops 20% after maximum peak force). Return the cross head to its original position. Force and extension data is acquired at a rate of 100 Hz throughout the experiment.

Set the nominal gage length to 40 mm using a calibrated caliper block and zero the crosshead. Insert the specimen into the upper grip such that the middle of the test strip is positioned 20 mm below the grip. The specimen may be folded perpendicular to the pull axis, and placed in the grip to achieve this position. After the grip is closed the excess material can be trimmed. Insert the specimen into the lower grips and close. Once again, the strip can be folded, and then trimmed after the grip is closed. Zero the load cell. The specimen should have a minimal slack but less than 0.05 N of force on the load cell. Start the test program. From the data construct a Force (N) verses Extension (mm). The Average-Pre-Strain is calculated from the bend in the curve corresponding to the extension at which the nonwovens in the elastic are engaged. Plot two lines, corresponding to the region of the curve before the bend (primarily the elastics), and the region after the bend (primarily the non-wovens). Read the extension at which these two lines intersect, and calculate the % Pre-Strain from the extension and the corrected gage length. Record as % Pre-strain 0.1%. Calculate the arithmetic mean of three replicate samples for each elastomeric laminate and Average-Pre-Strain to the nearest 0.1%.

Combinations

A1. An absorbent article comprising: a first belt comprising an inner wearer facing surface and an outer garment facing surface, the first belt further comprising a laterally extending inner edge and a laterally extending outer edge, the outer edge positioned longitudinally outward of the inner edge, the first belt further comprising a first region and a second region, wherein the first region comprises a first number of layers of substrates and the second region comprises a second number of layers of substrates, wherein the first number of layers substrates is greater than second number of layers of substrates; a second belt, wherein laterally opposing end portions of the second belt are connected with laterally opposing end portions of the first belt at a first side seam and a second side seam to form a waist opening; a chassis comprising a topsheet, a backsheet, and an absorbent core positioned between the topsheet and the backsheet, and wherein longitudinally opposing end regions of the chassis are connected with the first belt and the second belt; and a frangible pathway in the first belt comprising first lines of weakness positioned in the first region, second lines of weakness positioned in the second region, and at least one transition line of weakness extending partially through the first region and the second region.

A2. The absorbent article of paragraph A1, wherein the first lines of weakness extend for first lengths, the second lines of weakness extend for second lengths, and the at least one transition line of weakness extends for a third length, wherein the third length is greater than the first lengths and the second lengths.

A3. The absorbent article of either paragraph A1 of A2, wherein the first lines of weakness are separated from each other by a first separation distance and the second lines of weakness are separated from each other by a second separation distance, wherein the first separation distance is less than the second separation distance.

A4. The absorbent article of any of paragraphs A1 to A3, wherein the first lines of weakness comprise discrete cut lines that penetrate through some or all the layers of the first region; wherein the second lines of weakness comprise discrete cut lines that penetrate through some or all the layers of the second region; and wherein the at least one transition line of weakness comprises a discrete cut line that penetrates through some or all the layers of the first region and the second region.

A5. The absorbent article of any of paragraphs A1 to A4, wherein the first belt comprises a first substrate and a second substrate; wherein the first substrate comprises a laterally extending first edge, a laterally extending second edge, a first surface and an opposing second surface; wherein the second substrate comprises a laterally extending first edge, a laterally extending second edge, a first surface and an opposing second surface; wherein the second surface of the first substrate is in a facing relationship with the first surface of the second substrate; wherein the first substrate is folded along a fold line such that a first portion of the first substrate is in a facing relationship with a second portion of the first substrate; and wherein the first portion extends longitudinally between the fold line and the first edge of the first substrate, and wherein the second portion extends longitudinally between the fold line and the second edge of the first substrate.

A6. The absorbent article of paragraph A5, wherein the first edge of the first substrate extends laterally through a zone of adhesive to define a first adhesion zone and a second adhesion zone, the first adhesion zone extending longitudinally from the first edge of the first substrate toward the fold line and the second adhesion zone extending longitudinally from the first edge of the first substrate away from the fold line.

A7. The absorbent article of paragraph A6, wherein the at least one transition line of weakness extends across the zone of adhesive and severs the first edge of the first substrate.

A8. The absorbent article of paragraph A6, wherein adhesive in the first adhesion zone bonds the first portion of the first substrate with the second portion of the first substrate, and wherein adhesive in the second adhesion zone bonds the first surface of the second substrate with the second surface of the first substrate in the second portion.

A9. The absorbent article of any of paragraphs A5 to A8, wherein the first edge of the first substrate defines a border between the first region of the first belt and the second region of the first belt.

A10. The absorbent article of paragraph A9, wherein the first region of the first belt extends longitudinally from the first edge of the second substrate to the first edge of the first substrate.

A11. The absorbent article of any of paragraph A5 to A10, wherein the fold line defines the outer edge of the first belt.

A12. The absorbent article of paragraph A11, wherein the second region of the first belt extends longitudinally from the first edge of the first substrate to the inner edge of the first belt.

A13. The absorbent article of any of paragraphs A5 to A12, wherein the first surface of the first substrate in the second portion at least partially defines the outer garment facing surface of the first belt.

A14. The absorbent article of any of paragraphs A5 to A13, wherein the second surface of the second substrate at least partially defines the inner wearer facing surface of the first belt.

A15. The absorbent article of any of paragraphs A5 to A14, further comprising a grip region positioned between the first edge and the second edge of the first belt.

A16. The absorbent article of paragraph A15, wherein upon application of a pulling force to the grip region in a direction toward the first side seam and/or outward away from the first belt, a tear line propagates along the frangible pathway across the second region, the first edge of the first substrate, and across the first region.

A17. The absorbent article of any of paragraphs A1 to A16, wherein the frangible pathway in the first belt extends between a proximal terminus on the inner edge of the first belt and a distal terminus on the outer edge of the first belt.

A18. The absorbent article of paragraph A17, wherein the at least one transition line of weakness comprises a first transition line of weakness and a second transition line of weakness, wherein the first transition line of weakness is laterally spaced from the second transition line of weakness.

A19. The absorbent article of paragraph A18, wherein the first lines of weakness define a first region tear zone extending from the distal terminus to the first transition line of weakness.

A20. The absorbent article of paragraph A19, further comprising an accessibility opening in the first belt, and wherein the second lines of weakness define a second region tear zone extending from the accessibility opening to second transition line of weakness.

A21. The absorbent article of paragraph A21, wherein a portion of the chassis overlaps the inner wearer facing surface of the first belt to define a chassis overlap region, and wherein the accessibility opening in the first belt is positioned in the chassis overlap region.

A22. The absorbent article of paragraph A21, wherein the distal terminus is positioned laterally between the chassis overlap region and the first side seam.

A23. The absorbent article of paragraph A21, further comprising a fastener component positioned between the inner wearer facing surface of the first belt and the backsheet.

A24. The absorbent article of paragraph A21, wherein the accessibility opening comprises a slit in the first belt.

A25. The absorbent article of any of paragraphs A1 to A24, wherein the first belt further comprises first elastic material sandwiched by between at least two layers of substrates in the second region.

A26. The absorbent article of paragraph A25, wherein the first belt further comprises second elastic material sandwiched by between at least two layers of substrates in the first region.

A27. The absorbent article of paragraph A26, wherein the first elastic material and the second elastic material comprise elastic strands.

B1. A method for assembling absorbent articles, the method comprising steps of: advancing a first substrate in a machine direction, first substrate comprising a first surface and an opposing second surface, the first substrate further comprising a first edge and a second edge separated from the first edge in a cross direction; applying adhesive to the second surface of the first substrate to define a zone of adhesive extending in the machine direction; folding the first substrate along a fold line such that a first portion of the first substrate is placed in a facing relationship with a second portion of the first substrate, and wherein the first edge of the first substrate extends in the machine direction through the zone of adhesive to define a first adhesion zone and a second adhesion zone, wherein the first edge of the first substrate and the first portion of the first substrate are bonded with the second portion of the first substrate, and wherein the second adhesion zone extends in the cross direction from the first edge of the first substrate toward the second edge of the first substrate; providing a second substrate comprising a first surface and an opposing second surface, the second substrate further comprising a first edge and a second edge separated from the first edge in a cross direction; positioning stretched elastic strands between the first substrate and the second substrate; forming an elastic laminate by bonding the first substrate together with the second substrate, wherein first portion of the first substrate is positioned between the second surface of the first substrate and the first surface of the second substrate, and wherein the second adhesion zone bonds the second surface of the first substrate with the first surface of the second substrate, wherein the elastic laminate comprises a first region comprising a first number of layers of substrates and a second region comprising a second number of layers of substrates, wherein the first edge of the first substrate defines a border between the first region and the second region; forming a frangible pathway in the elastic laminate, the frangible pathway comprising first lines of weakness in the first region, second lines of weakness in the second region, and at least one transition line of weakness, wherein the at least one transition line of weakness extends across the first edge of the first substrate into both the first region and the second region; providing a chassis that comprises a body facing surface and a garment facing surface, and an absorbent core positioned between the body facing surface and the garment facing surface; and bonding the chassis with the elastic laminate.

B2. The method of paragraph B1, further comprising a step of bonding at least one elastic strand with the second surface of first substrate, and wherein the step of folding further comprises placing the first portion of the first substrate in a facing relationship with the second portion of the first substrate such that the at least one elastic strand is positioned between the first portion and the second portion.

C1. An absorbent article comprising: a first belt comprising an inner wearer facing surface and an outer garment facing surface, the first belt further comprising a laterally extending inner edge and a laterally extending outer edge, the outer edge positioned longitudinally outward of the inner edge, the first belt further comprising a first region and a second region, wherein the first region comprises a first number of layers of substrates and the second region comprises a second number of layers of substrates, wherein the first number of layers substrates is greater than second number of layers of substrates; wherein the first substrate comprises a laterally extending first edge, a laterally extending second edge, a first surface and an opposing second surface, wherein the second substrate comprises a laterally extending first edge, a laterally extending second edge, a first surface and an opposing second surface, wherein the second surface of the first substrate is in a facing relationship with the first surface of the second substrate, wherein the first substrate is folded along a fold line such that a first portion of the first substrate is in a facing relationship with a second portion of the first substrate, and wherein the first portion extends longitudinally between the fold line and the first edge of the first substrate, and wherein the second portion extends longitudinally between the fold line and the second edge of the first substrate; wherein the first edge of the first substrate extends laterally through a zone of adhesive to define a first adhesion zone and a second adhesion zone, the first adhesion zone extending longitudinally from the first edge of the first substrate toward the fold line and the second adhesion zone extending longitudinally from the first edge of the first substrate away from the fold line; a second belt, wherein laterally opposing end portions of the second belt are connected with laterally opposing end portions of the first belt at a first side seam and a second side seam to form a waist opening; a chassis comprising a topsheet, a backsheet, and an absorbent core positioned between the topsheet and the backsheet, and wherein longitudinally opposing end regions of the chassis are connected with the first belt and the second belt; and a frangible pathway in the first belt comprising lines of weakness positioned in the first region and the second region.

C2. The absorbent article of paragraph C1, wherein adhesive in the first adhesion zone bonds the first portion of the first substrate with the second portion of the first substrate, and wherein adhesive in the second adhesion zone bonds the first surface of the second substrate with the second surface of the first substrate in the second portion.

Bio-Based Content for Components

Components of the absorbent articles described herein may at least partially be comprised of bio-based content as described in U.S. Pat. Appl. No. 2007/0219521 A1. For example, the superabsorbent polymer component may be bio-based via their derivation from bio-based acrylic acid. Bio-based acrylic acid and methods of production are further described in U.S. Pat. Appl. Pub. No. 2007/0219521 and U.S. Pat. Nos. 8,703,450; 9,630,901 and 9,822,197. Other components, for example nonwoven and film components, may comprise bio-based polyolefin materials. Bio-based polyolefins are further discussed in U.S. Pat. Appl. Pub. Nos. 2011/0139657, 2011/0139658, 2011/0152812, and 2016/0206774, and U.S. Pat. No. 9,169,366. Example bio-based polyolefins for use in the present disclosure comprise polymers available under the designations SHA7260™, SHE150™, or SGM9450F™ (all available from Braskem S.A.).

An absorbent article component may comprise a bio-based content value from about 10% to about 100%, from about 25% to about 100%, from about 40% to about 100%, from about 50% to about 100%, from about 75% to about 100%, or from about 90% to about 100%, for example, using ASTM D6866-10, method B.

Recycle Friendly and Bio-Based Absorbent Articles

Components of the absorbent articles described herein may be recycled for other uses, whether they are formed, at least in part, from recyclable materials. Examples of absorbent article materials that may be recycled are nonwovens, films, fluff pulp, and superabsorbent polymers. The recycling process may use an autoclave for sterilizing the absorbent articles, after which the absorbent articles may be shredded and separated into different byproduct streams. Example byproduct streams may comprise plastic, superabsorbent polymer, and cellulose fiber, such as pulp. These byproduct streams may be used in the production of fertilizers, plastic articles of manufacture, paper products, viscose, construction materials, absorbent pads for pets or on hospital beds, and/or for other uses. Further details regarding absorbent articles that aid in recycling, designs of recycle friendly diapers, and designs of recycle friendly and bio-based component diapers, are disclosed in U.S. Pat. Appl. Publ. No. 2019/0192723, published on Jun. 27, 2019.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a first belt comprising an inner wearer facing surface and an outer garment facing surface, the first belt further comprising a laterally extending inner edge and a laterally extending outer edge, the outer edge positioned longitudinally outward of the inner edge, the first belt further comprising a first region and a second region, wherein the first region comprises a first number of layers of substrates and the second region comprises a second number of layers of substrates, wherein the first number of layers substrates is greater than second number of layers of substrates;
a second belt, wherein laterally opposing end portions of the second belt are connected with laterally opposing end portions of the first belt at a first side seam and a second side seam to form a waist opening;
a chassis comprising a topsheet, a backsheet, and an absorbent core positioned between the topsheet and the backsheet, and wherein longitudinally opposing end regions of the chassis are connected with the first belt and the second belt; and
a frangible pathway in the first belt comprising first lines of weakness positioned in the first region, second lines of weakness positioned in the second region, and at least one transition line of weakness extending partially through the first region and the second region; and
wherein the first belt further comprises a first substrate and a second substrate, wherein the first substrate comprises a laterally extending first edge, a laterally extending second edge, a first surface and an opposing second surface, wherein the second substrate comprises a laterally extending first edge, a laterally extending second edge, a first surface and an opposing second surface, wherein the second surface of the first substrate is in a facing relationship with the first surface of the second substrate, wherein the first substrate is folded along a fold line such that a first portion of the first substrate is in a facing relationship with a second portion of the first substrate, and wherein the first portion extends longitudinally between the fold line and the first edge of the first substrate, and wherein the second portion extends longitudinally between the fold line and the second edge of the first substrate.

2. The absorbent article of claim 1, wherein the first lines of weakness extend for first lengths, the second lines of weakness extend for second lengths, and the at least one transition line of weakness extends for a third length, wherein the third length is greater than the first lengths and the second lengths.

3. The absorbent article of claim 1, wherein the first lines of weakness are separated from each other by a first separation distance and the second lines of weakness are separated from each other by a second separation distance, wherein the first separation distance is less than the second separation distance.

4. The absorbent article of claim 1, wherein the first lines of weakness comprise discrete cut lines that penetrate through some or all the layers of the first region; wherein the second lines of weakness comprise discrete cut lines that penetrate through some or all the layers of the second region; and wherein the at least one transition line of weakness comprises a discrete cut line that penetrates through some or all the layers of the first region and the second region.

5. The absorbent article of claim 1, wherein the first edge of the first substrate extends laterally through a zone of adhesive to define a first adhesion zone and a second adhesion zone, the first adhesion zone extending longitudinally from the first edge of the first substrate toward the fold line and the second adhesion zone extending longitudinally from the first edge of the first substrate away from the fold line.

6. The absorbent article of claim 5, wherein the at least one transition line of weakness extends across the zone of adhesive and severs the first edge of the first substrate.

7. The absorbent article of claim 5, wherein adhesive in the first adhesion zone bonds the first portion of the first substrate with the second portion of the first substrate, and wherein adhesive in the second adhesion zone bonds the first surface of the second substrate with the second surface of the first substrate in the second portion.

8. The absorbent article of claim 1, wherein the first edge of the first substrate defines a border between the first region of the first belt and the second region of the first belt.

9. The absorbent article of claim 8, wherein the first region of the first belt extends longitudinally from the first edge of the second substrate to the first edge of the first substrate.

10. The absorbent article of claim 9, wherein the fold line defines the outer edge of the first belt.

11. The absorbent article of claim 10, wherein the second region of the first belt extends longitudinally from the first edge of the first substrate to the inner edge of the first belt.

12. The absorbent article of claim 1, wherein the first surface of the first substrate in the second portion at least partially defines the outer garment facing surface of the first belt.

13. The absorbent article of claim 1, wherein the second surface of the second substrate at least partially defines the inner wearer facing surface of the first belt.

14. The absorbent article of claim 1, further comprising a grip region positioned between the first edge and the second edge of the first belt.

15. The absorbent article of claim 14, wherein upon application of a pulling force to the grip region in a direction toward the first side seam and/or outward away from the first belt, a tear line propagates along the frangible pathway across the second region, the first edge of the first substrate, and across the first region.

16. The absorbent article of claim 1, wherein the frangible pathway in the first belt extends between a proximal terminus on the inner edge of the first belt and a distal terminus on the outer edge of the first belt.

17. The absorbent article of claim 16, wherein the at least one transition line of weakness comprises a first transition line of weakness and a second transition line of weakness, wherein the first transition line of weakness is laterally spaced from the second transition line of weakness.

18. The absorbent article of claim 17, wherein the first lines of weakness define a first region tear zone extending from the distal terminus to the first transition line of weakness.

19. The absorbent article of claim 18, further comprising an accessibility opening in the first belt, and wherein the second lines of weakness define a second region tear zone extending from the accessibility opening to second transition line of weakness.

20. The absorbent article of claim 19, wherein a portion of the chassis overlaps the inner wearer facing surface of the first belt to define a chassis overlap region, and wherein the accessibility opening in the first belt is positioned in the chassis overlap region.

21. The absorbent article of claim 20, wherein the distal terminus is positioned laterally between the chassis overlap region and the first side seam.

22. The absorbent article of claim 20, further comprising a fastener component positioned between the inner wearer facing surface of the first belt and the backsheet.

23. The absorbent article of claim 20, wherein the accessibility opening comprises a slit in the first belt.

24. The absorbent article of claim 1, wherein the first belt further comprises first elastic material sandwiched by between at least two layers of substrates in the second region.

25. The absorbent article of claim 24, wherein the first belt further comprises second elastic material sandwiched by between at least two layers of substrates in the first region.

26. The absorbent article of claim 25, wherein the first elastic material and the second elastic material comprise elastic strands.

*  *  *  *  *